United States Patent
DiNinno et al.

[11] Patent Number: 5,214,139
[45] Date of Patent: * May 25, 1993

[54] 2-PHENANTHRIDONYL-CARBAPENEMS

[75] Inventors: Frank DiNinno, Old Bridge; Thomas A. Rano, Somerville; Mark L. Greenlee, Rahway, all of N.J.

[73] Assignee: Merck & Co., Inc., Rahway, N.J.

[*] Notice: The portion of the term of this patent subsequent to Oct. 20, 2009 has been disclaimed.

[21] Appl. No.: 686,109

[22] Filed: Apr. 16, 1991

[51] Int. Cl.$^5$ .......................................... C07D 487/04
[52] U.S. Cl. ................................................. 540/302
[58] Field of Search ...................................... 540/302

[56] References Cited

U.S. PATENT DOCUMENTS

| | | | |
|---|---|---|---|
| 4,260,627 | 4/1981 | Christensen et al. | 424/274 |
| 4,465,632 | 8/1984 | Christensen et al. | 260/245.2 |
| 4,543,257 | 9/1985 | Cama et al. | 514/210 |
| 4,775,669 | 10/1988 | Cama et al. | 514/210 |
| 4,962,101 | 10/1990 | DiNinno et al. | 514/210 |
| 4,978,659 | 8/1989 | DiNinno et al. | 514/210 |
| 5,004,739 | 4/1991 | Salzmann et al. | 514/210 |
| 5,004,740 | 4/1991 | Salzmann et al. | 514/210 |
| 5,006,519 | 4/1991 | DiNinno et al. | 514/210 |
| 5,011,832 | 4/1991 | Salzmann et al. | 514/210 |
| 5,025,006 | 6/1991 | Salzmann et al. | 514/210 |
| 5,025,007 | 6/1991 | Greenlee et al. | 514/210 |
| 5,025,008 | 6/1991 | DiNinno et al. | 514/210 |
| 5,032,587 | 7/1991 | DiNinno et al. | 514/210 |
| 5,034,384 | 7/1991 | Greenlee et al. | 514/210 |
| 5,034,385 | 7/1991 | DiNinno et al. | 514/210 |
| 5,037,820 | 8/1991 | DiNinno et al. | 514/210 |

OTHER PUBLICATIONS

L. D. Cama et al., Total Synthesis of Thienamycin Analogs-III Tetrahedron 39, 2531 (1983).
R. N. Guthikonda et al., Structure Activity Relationship in the 2-Arylcarbapenem Series, J. Med. Chem., 30, 871 (1987).
Ser. No. 741,183, Jul. 1991, DiNinno et al.
Ser. No. 593,849, Oct. 1990, Guthikonda et al.

Primary Examiner—Robert Gerstl
Attorney, Agent, or Firm—Richard C. Billups; Raymond M. Speer

[57] ABSTRACT

Carbapenems of the formula

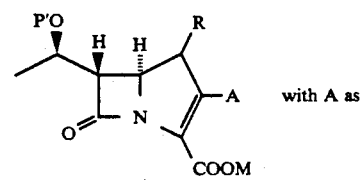

with A as

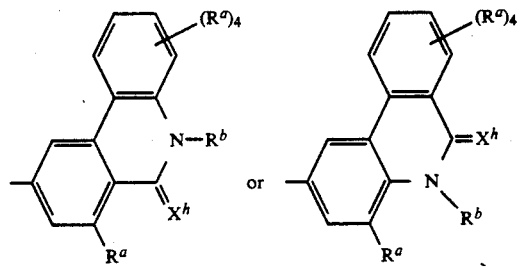

wherein:
P' is a removable protecting group for hydroxy; and
M is a removable protecting group for carboxy;
are useful intermediates for carbapenem antibiotics.

11 Claims, No Drawings

2-PHENANTHRIDONYL-CARBAPENEMS

BACKGROUND OF THE INVENTION

The present invention relates to antibacterial agents of the carbapenem class, in which the 2-position side-chain is characterized by a phenanthridone moiety, substituted by various cationic and neutral substituents, as described in more detail further below.

Thienamycin was an early carbapenem antibacterial agent having a broad spectrum; it has the following formula:

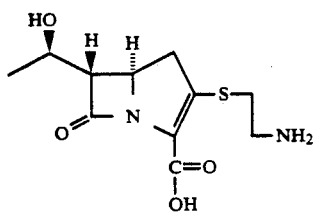

Later, N-formimidoyl thienamycin was discovered; it has the formula:

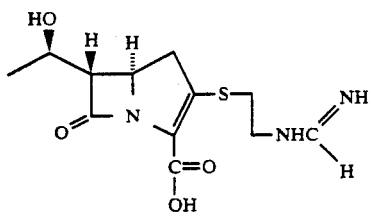

The 2-phenanthridonyl-carbapenems of the present invention are not characterized by a broad antibacterial spectrum such as that of thienamycin or N-formimidoyl thienamycin. Rather, their spectrum of activity is largely limited to gram positive microorganisms, especially methicillin resistant *Staphylococcus aureus* (MRSA), methicillin resistant *Staphylococcus epidermidis* (MRSE), and methicillin resistant coagulase negative Staphylococci (MRCNS). The antibacterial compounds of the present invention thus comprise an important contribution to therapy of these difficult to control pathogens. Moreover, there is an increasing need for agents effective against such pathogens (MRSA/MRCNS) which are at the same time safe, i.e., free from undesirable toxic side effects. No β-lactam antibacterial has yet been found which meets these requirements. And, the current agent of choice, vancomycin, a glycopeptide antibacterial, is experiencing an ever increasing amount of resistance in the MRSA/MRCNS pathogens.

More recently, carbapenem antibacterial agents have been described which have a 2-substituent which is an aryl moiety optionally substituted by, e.g., aminomethyl and substituted aminomethyl. These agents are described in U.S. Pat. Nos. 4,543,257 and 4,260,627 and have the formula:

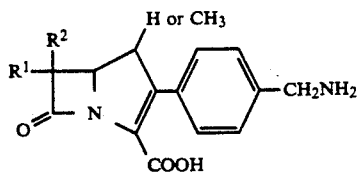

However, there is no description or suggestion of a phenanthrenyl 2-substituent such as characterizes the compounds of the present invention, nor is there any suggestion of the surprisingly better anti-MRSA/MRCNS activity of the compounds of the present invention.

U.S. Pat. No. 4,978,659 describes a particular class of compounds of the formula:

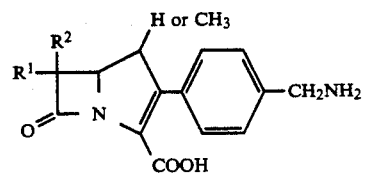

but this limited teaching in no way suggests the totally different compounds of the present invention, nor their surprisingly better anti-MRSA/MRCNS activity.

SUMMARY OF INVENTION

The present invention provides novel carbapenem compounds of the formula:

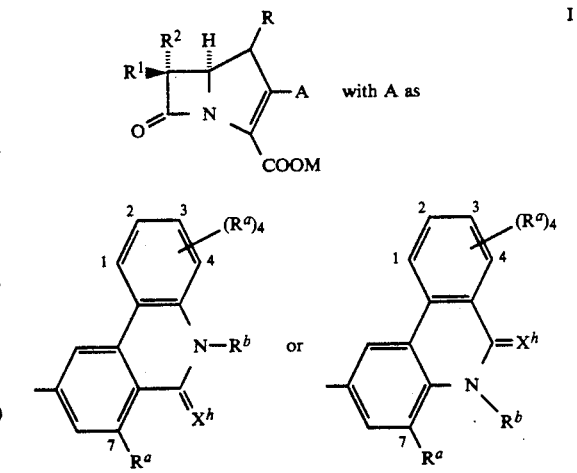

wherein:

R is H or CH$_3$;

R$^1$ and R$^2$ are independently H, CH$_3$—, CH$_3$CH$_2$—, (CH$_3$)$_2$CH—, HOCH$_2$—, CH$_3$CH(OH)—, (CH$_3$)$_2$C(OH)—, FCH$_2$CH(OH)—, F$_2$CHCH(OH)—, F$_3$CCH(OH)—, CH$_3$CH(F)—, CH$_3$CF$_2$—, or (CH$_3$)$_2$C(F)—;

X$^h$ is O or S;

R$^a$ are independently selected from the group consisting of hydrogen and the radicals set out below, provided that one but not more than one R$^a$ or R$^b$ is or contains a Type I substituent, the remaining non-hydrogen substituents being selected from Type II, and in total not more than four R$^a$ and R$^b$ radicals are other than hydrogen:

I.
a)

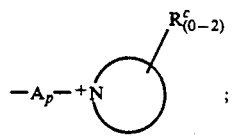

where

A is $(CH_2)_m$—Q—$(CH_2)_n$, where m is 0 to 6 and n is 1 to 6 and Q is a covalent bond, O, S, SO, $SO_2$, NH, —$SO_2$NH—, —$NHSO_2$—, —CONH—, —NHCO—, —$SO_2$N($C_1$-$C_4$alkyl)—, —N($C_1$-$C_4$alkyl)$SO_2$—, —CON($C_1$-$C_4$alkyl)—, —N($C_1$-$C_4$alkyl)CO—, —CH=CH—, —CO—, —OC(O)—, —C(O)O— or N($C_1$-$C_4$alkyl) and $(CH_2)_m$ is attached to the phenanthridonyl moiety;

is a 5- or 6-membered monocyclic heterocycle or an 8-, 9- or 10-membered bicyclic heterocycle, the heterocycle containing a first nitrogen in an aromatic 5- or 6-membered first ring, with attachment of the heterocycle to A by way of said first nitrogen and said first nitrogen is quaternary by virtue of the attachment and ring bonds, with the first ring containing 0 or 1 of either O or S, with the first ring containing 0 to 3 additional nitrogen atoms, with the first ring optionally fused to a 3- or 4-membered moiety to form the optional second ring, with the moiety containing at least one carbon atom, with the moiety containing 0 or 1 of either O or S, with the moiety containing 0 to 2 nitrogen atoms, and with the moiety being saturated or unsaturated and the second ring aromatic or non-aromatic;

$R^c$ is $R^a$ as defined under II below, hydrogen, or —$NR^yR^z$ (where $R^y$ and $R^z$ are defined in II below), but independently selected from $R^a$ and from each other if more than one $R^c$ is present, and is attached to a carbon ring atom or a nitrogen heteroatom the valency of which is not satisfied by the ring bonds;

p is 0 or 1;

b)

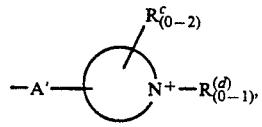

where

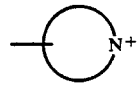

is a 5- or 6-membered monocyclic heterocycle or an 8-, 9- or 10-membered bicyclic heterocycle, the heterocycle containing a first nitrogen in an aromatic 5- or 6-membered first ring, with said first nitrogen quaternary by virtue of a substituent $R^d$ in addition to the ring bonds thereto, with said first nitrogen neutral in the absence of a substituent $R^d$, with attachment of the heterocycle to A' by way of a carbon atom of a ring, with the first ring containing 0 or 1 of either O or S, with the first ring containing 0 to 2 additional nitrogen atoms, with the first ring optionally fused to a 3- or 4-membered moiety to form the optional second ring, with the moiety containing at least one carbon atom, with the moiety containing 0 or 1 of either O or S, with the moiety containing 0 to 2 nitrogen atoms, and with the moiety being saturated or unsaturated and the second ring aromatic or non-aromatic;

$R^c$ is defined above;

$R^d$ is hydrogen, $NH_2$, $O^-$ or $C_1$-$C_4$alkyl (where the alkyl group is optionally mono-substituted with $R^q$ as defined under IIc below);

A' is $(CH_2)_m$—Q—$(CH_2)_n$, where m is 0 to 6 and n is 0 to 6, Q is given above, and when m and n are 0 then Q is not a covalent bond;

c) —$A_p$—$N^+R^y(R^w)_{0-1}(R^z)$ where $R^y$ and $R^z$ are as defined under II below, $R^y$ and $R^z$ may further be together a $C_2$-$C_4$ alkylidene radical to form a ring (optionally mono-substituted with $R^q$ as defined below) interrupted by N(O)$R^e$ or $N^+(R^e)_2$ (where $R^e$ is hydrogen, $C_1$-$C_4$ alkyl, or $C_1$-$C_4$ alkyl mono-substituted with $R^q$ as defined below), $R^w$ is hydrogen, $C_{1-4}$ alkyl, $O^-$, $NH_2$, or absent in which case the nitrogen is neutral, $R^w$, $R^y$ and $R^z$ may further together form a $C_5$-$C_{10}$ tertiary alkylidene radical which with $N^+$ forms a bicyclic ring, where the tertiary alkylidene radical is optionally mono-substituted with $R^q$ as defined below and where the tertiary carbon of the tertiary alkylidene radical is optionally replaced with nitrogen $N^+R^e$ (where $R^e$ is defined above), or $N^+$—$O^-$, p is 0 or 1, and A is as defined above;

d)

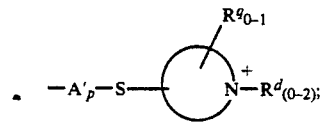

where

is a 5- or 6-membered monocyclic heterocycle or an 8-, 9- or 10-membered bicyclic heterocycle, the heterocycle containing a first nitrogen in a first ring, with the first ring saturated or unsaturated and non-aromatic, with the first nitrogen quaternary by virtue of one or two substituents $R^d$ in addition to the ring bonds thereto, with the first nitrogen alternatively neutral by virtue of zero or one substituents $R^d$ in addition to the ring bonds thereto with attachment of the heterocycle to A' by way of a carbon atom or non-quaternary nitrogen atom of a ring, with the first ring containing in addition to carbon and the first nitrogen 0 to 1 of a member selected from the group consisting of the non-quaternary nitrogen of attachment, O, S, S(O), $S(O)_2$ and NR$^e$ where R$^e$ is defined above, with the first ring optionally fused to a 2-, 3- or 4-membered moiety to form the optional second ring, with the moiety optionally containing in addition to carbon the non-quaternary nitrogen of attachment, and with the moiety saturated or unsaturated and the second ring non-aromatic;

R$^d$ is defined above and where more than one R$^d$ is present on a nitrogen, at least one R$^d$ is hydrogen or C$_1$–C$_4$alkyl;

A' is defined above; and p is defined above;

R$^q$ is defined below;

II.

a) a trifluoromethyl group: —CF$_3$;

b) a halogen atom: —Br, —Cl, —F, or —I;

c) C$_1$–C$_4$ alkoxy radical: —OC$_{1-4}$ alkyl, wherein the alkyl is optionally mono-substituted by R$^q$, where R$^q$ is a member selected from the group consisting of —OH, —OCH$_3$, —CN, —C(O)NH$_2$, —OC(O)NH$_2$, CHO, —OC(O)N(CH$_3$)$_2$, —SO$_2$NH$_2$, —SO$_2$N(CH$_3$)$_2$, —SOCH$_3$, —SO$_2$CH$_3$, —F, —CF$_3$, —COOM$^a$ (where M$^a$ is hydrogen alkali metal, methyl or phenyl), tetrazolyl (where the point of attachment is the carbon atom of the tetrazole ring and one of the nitrogen atoms is mono-substituted by M$^a$ as defined above) and —SO$_3$M$^b$ (where M$^b$ is hydrogen or an alkali metal);

d) a hydroxy group: —OH;

e) a carbonyloxy radical: —O(C=O)R$^s$, where

R$^s$ is C$_{1-4}$ alkyl or phenyl, each of which is optionally mono-substituted by R$^q$ is defined above;

f) a carbamoyloxy radical: —O(C=O)N(R$^y$)R$^z$ where

R$^y$ and R$^z$ are independently H, C$_{1-4}$ alkyl (optionally mono-substituted by R$^q$ as defined above), together a 3- to 5-membered alkylidene radical to form a ring (optionally substituted with R$^q$ as defined above) or together a 2- to 4-membered alkylidene radical, interrupted by —O—, —S—, —S(O)— or —S(O)$_2$— to form a ring where the ring is optionally mono-substituted with R$_q$ as defined above);

g) a sulfur radical: —S(O)$_n$—R$^s$ where n=0–2, and R$^s$ is defined above;

h) a sulfamoyl group: —SO$_2$N(R$^y$)R$^z$ where R$^y$ and R$^z$ are as defined above;

i) azido: N$_3$ j) a formamido group: —N(R$^t$)(C=O)H, where

R$^t$ is H or C$_{1-4}$ alkyl, and the alkyl thereof is optionally mono-substituted by R$^q$ as defined above;

k) a (C$_1$–C$_4$ alkyl)carbonylamino radical: —N(R$^t$)(C=O)C$_{1-4}$ alkyl, where R$^t$ is as defined above, and the alkyl group is also optionally mono-substituted by R$^q$ as defined above;

l) a (C$_1$–C$_4$ alkoxy) carbonylamino radical: —N(R$^t$)(C=O)OC$_{1-4}$ alkyl, where R$^t$ is as defined above, and the alkyl group is also optionally mono-substituted by R$^q$ as defined above;

m) a ureido group: —N(R$^t$)(C=O)N(R$^y$)R$^z$ where R$^t$, R$^y$ and R$^z$ are as defined above;

n) a sulfonamido group: —N(R$^t$)SO$_2$R$^s$, where R$^s$ and R$^t$ are as defined above;

o) a cyano group: —CN;

p) a formyl or acetalized formyl radical: —(C=O)H or —CH(OCH$_3$)$_2$;

q) (C$_1$–C$_4$ alkyl)carbonyl radical wherein the carbonyl is acetalized: —C(OCH$_3$)$_2$C$_{1-4}$ alkyl, where the alkyl is optionally mono-substituted by R$^q$ as defined above;

r) carbonyl radical: —(C=O)R$^s$, where R$^s$ is as defined above;

s) a hydroximinomethyl radical in which the oxygen or carbon atom is optionally substituted by a C$_1$–C$_4$ alkyl group: —(C=NOR$^z$)R$^y$ where R$^y$ and R$^z$ are as defined above, except they may not be joined together to form a ring;

t) a (C$_1$–C$_4$ alkoxy)carbonyl radical: —(C=O)OC$_{1-4}$ alkyl, where the alkyl is optionally mono-substituted by R$^q$ as defined above;

u) a carbamoyl radical: —(C=O)N(R$^y$)R$^z$ where R$^y$ and R$^z$ are as defined above;

v) an N-hydroxycarbamoyl or N(C$_1$–C$_4$ alkoxy)carbamoyl radical in which the nitrogen atom may be additionally substituted by a C$_1$–C$_4$ alkyl group: —(C=O)—N(OR$^y$)R$^z$ where R$^y$ and R$^z$ are as defined above, except they may not be joined together to form a ring;

w) a thiocarbamoyl group: —(C=S)N(R$^y$)(R$^z$) where R$^y$ and R$^z$ are as defined above;

x) carboxyl: —COOM$^b$, where M$^b$ is as defined above;

y) thiocyanate: —SCN;

z) trifluoromethylthio: —SCF$_3$;

aa) tetrazolyl, where the point of attachment is the carbon atom of the tetrazole ring and one of the nitrogen atoms is mono-substituted by hydrogen, an alkali metal or a C$_1$–C$_4$ alkyl optionally substituted by R$^q$ as defined above;

ab) an anionic function selected from the group consisting of: phosphono [P=O(OM$^b$)$_2$]; alkylphosphono {P=O(OM$^b$)—[O(C$_1$–C$_4$ alkyl)]}; alkylphosphinyl [P=O(OM$^b$)—(C$_1$–C$_4$alkyl)]; phosphoramido [P=O(OM$^b$)N(R$^y$)R$^z$ and P=O(OM$^b$)NHR$^x$]; sulfino (SO$_2$M$^b$); sulfo (SO$_3$M$^b$); acylsulfonamides selected from the structures CONM$^b$SO$_2$R$^x$, CONM$^b$SO$_2$N(R$^y$)R$^z$, SO$_2$NM$^b$CON(R$^y$) R$^z$; and SO$_2$NM$^b$CN, where R$^x$ is phenyl or heteroaryl, where heteroaryl is a monocyclic aromatic hydrocarbon group having 5 or 6 ring atoms, in which a carbon atom is the point of attachment, in which one of the carbon atoms has been replaced by a nitrogen atom, in which one additional carbon atom is optionally replaced by a heteroatom selected from O or S, and in which from 1 to 2 additional carbon atoms are optionally replaced by a nitrogen heteroatom, and where the phenyl and heteroaryl are optionally mono-substituted by R$^q$, as defined above; M$^b$ is as defined above; and R$^y$ and R$^z$ are as defined above;

ac) C$_5$–C$_7$ cycloalkyl group in which one of the carbon atoms in the ring is replaced by a heteroatom selected from O, S, NH or N(C$_1$–C$_4$ alkyl) and in which one additional carbon atom may be replaced by NH or N(C$_1$–C$_4$ alkyl), and in which at least one carbon atom adjacent to each nitrogen heteroatom has both of its attached hydrogen atoms replaced by one oxygen thus forming a carbonyl moiety and there are one or two carbonyl moieties present in the ring;

ad) C$_2$–C$_4$ alkenyl radical, optionally mono-substituted by one of the substituents a) to ac) above and phenyl which is optionally substituted by R$^q$ as defined above;

ae) C$_2$–C$_4$ alkynyl radical, optionally mono-substituted by one of the substituents a) to ac) above;

af) C$_1$–C$_4$ alkyl radical;

ag) C$_1$–C$_4$ alkyl mono-substituted by one of the substituents a)-ac) above;

ah) a 2-oxazolidinonyl moiety in which the point of attachment is the nitrogen atom of the oxazolidinone ring, the ring oxygen atom is optionally replaced by a heteroatom selected from —S— and NR$^t$ (where R$^t$ is as defined above) and one of the saturated carbon atoms of the oxazolidinone ring is optionally mono-substituted by one of the substituents a) to ag) above;

R$^b$ is —H, —OH, —CF$_3$, —(C=O)R$^s$, —S(O)$_n$R$^s$ where n=0–2, —SO$_2$NR$^y$R$^z$, —(C=O)OC$_{1-4}$alkyl, —(C=O)N(R$^y$)R$^z$, —(C=O)N(OR$^y$)R$^z$, —(C=S)N-(R$^y$)R$^z$, —NH$_2$, C$_{1-4}$alkoxy optionally mono-substituted with R$^q$, R$^x$ as defined above, a Type I. b) or d) substituent as defined above, C$_{1-4}$ alkyl optionally mono-substituted on an alpha carbon or higher by one of the substituents Type I. a) or c) or Type II. a)–ae) as defined for R$^a$ above; and M is selected from:

i) hydrogen;

ii) a pharmaceutically acceptable esterifying group or removable carboxyl protecting group;

iii) an alkali metal or other pharmaceutically acceptable cation; or iv) a negative charge which is balanced by a positively charged group.

The present invention also provides novel carbapenem intermediates of the formula:

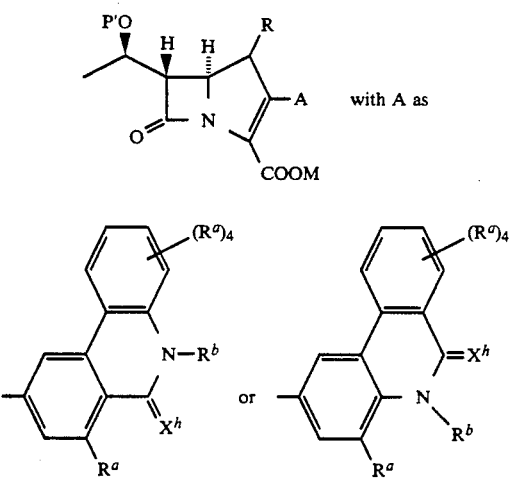

wherein:

R is H or CH$_3$;

X$^h$ is O or S;

R$^a$ and R$^b$ are defined above, with the proviso that R$^q$ additionally includes OP' where P' is defined below, that M$^a$ and M$^b$ of R$^q$ both include M and that the Type d) hydroxy substituent and R$^b$ additionally may be protected hydroxy, OP';

P' is a removable protecting group for hydroxy; and

M is a removable protecting group for carboxy; and the Type I, R$^a$ or R$^b$ substituent is balanced with the anionic form of Z where Z is methanesulfonyloxy, trifluoromethanesulfonyloxy, fluorosulfonyloxy, p-toluenesulfonyloxy, 2,4,6-triisopropylbenzenesulfonyloxy, p-bromobenzenesulfonyloxy, p-nitrobenzenesulfonyloxy, bromo and iodo.

Preferred intermediates have the formula:

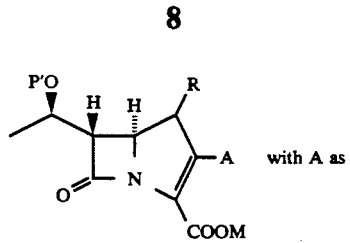

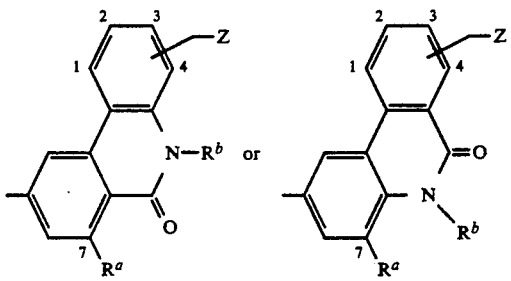

wherein

R is —H or —CH$_3$;

R$^a$ is selected from the group consisting of H, OP', Cl, Br, I, SCH$_3$, CN, CHO, SOCH$_3$, SO$_2$CH$_3$, CO$_2$M, CH$_2$OP' or CONH$_2$;

R$^b$ is H, OP', CH$_2$SCH$_3$, CH$_2$CN, CH$_2$CHO, CH$_2$SOCH$_3$, CH$_2$SO$_2$CH$_3$, CH$_2$CO$_2$M, CH$_2$OP', CH$_2$CH$_2$OP' or CH$_2$CONH$_2$;

P' is a removable protecting group for hydroxy;

M is a removable protecting group for carboxy; and

Z is selected from the group consisting of alkylsulfonyloxy, substituted alkylsulfonyloxy, arylsulfonyloxy, substituted arylsulfonyloxy, fluorosulfonyloxy, and halogen and with the proviso that the —CH$_2$—Z moiety is in the 3- or 4-position of the phenanthridone as numbered above.

DETAILED DESCRIPTION OF THE INVENTION

The manufacture of compounds of Formula I may be carried out in a three-stage synthesis scheme followed by a final step which allows for the removal of any protecting groups. The objective of the first synthetic stage is to produce a base phenanthridone compound which may be converted to the two-position substituent of the carbapenem of Formula I. The objective of the second synthetic stage is to attach the base phenanthridone to the carbapenem. Finally, the objective of the third synthetic stage is to substitute the phenanthridone with the desired R$^a$ and R$^b$. This third synthetic stage may be performed after the first synthetic stage or during or after the second synthetic stage according to the nature of the various R$^a$ and R$^b$.

Flow Sheets A1 and A2 demonstrate a suggested first stage synthesis. Flow Sheets B and C demonstrate two alternative second stage syntheses. The third synthesis varies according to the selected R$^a$ and R$^b$.

The suggested first synthesis herein, Flow Sheets A1 and A2, can be generally described as a directed ortho metalation reaction to prepare starting materials required for a Suzuki cross-coupling reaction and finally ring closure to produce the desired phenanthridone platform. This suggested first synthesis is utilized to produce similar phenanthridone compounds by Snieckus, V., Chem. Rev. 1990, 90, 879–933; Fu. J. M. and Snieckus, V., Tet. Lett. 1990, 31, p. 1665; Siddiqui, M. A., et al., Tetrahedron Letters, Vol. 29, No. 43, 5463–5466 (1988); Mills, R. J., et al., J. Org. Chem., 1989, 54, 4372–4385; Mills, R. J., J. Org. Chem., 1989, 54, 4386–4390; Fu, J. M., et al., Tetrahedron Letters, Vol. 31, No. 12, pp 1665–1668 (1990); and Suzuki, A., et al., Synthetic Communications, 11(7), 513–519 (1981).

Referring to Flow Sheet A1 compound A1-1 is substituted with a directed metalation group (DMG) by methods according to Snieckus, et al., above. The function of the directed metalation group (DMG) is to orchestrate adornment of the aromatic ring. It is highly desirable of the DMG that it also provide a precursor substituent for the necessary carboxy function or amino function forming the amide linkage of the object phenanthridone. Suitable DMG to serve as a carboxyl precursor are secondary and tertiary amides and oxazolino groups. Specifically these precursors may be, for example, —CONEt$_2$, —CONHMe, 4,4-dimethyl-2-oxazolinyl, and the like. In the instance of compound A1-1, DMG is of the carboxyl precursor type. Suitable DMG to serve as an amino precursor are protected primary and secondary amines. Specifically, these precursors may be —NH-t-Boc, —NH-pivaloyl, phenylsulfonamido, and the like. Compound A2-1 as described below is by way of example, of the amino precursor type.

As the first step of flow Sheet A1, the bromine of compound A1-1 is protected through silylation via halogen metal exchange in the presence of TMS chloride at between about $-100°$ to $-50°$ C. to produce aryl silane A1-2. Incorporation of an ortho substituent $R^a$ or its appropriate precursor may be made on compound A1-2 in accordance with standard directed metalation procedures described by Snieckus, et al., above. The resultant substituted aryl silane A1-3 is iteratively ortho metalated and treated with an appropriate boron containing electrophile to obtain the requisite aryl boronic acid A1-4. Suitable boron containing electrophiles include lower alkyl borates, such as trimethyl borate and tri-i-propyl borate. Alternatively, and not shown in the Flow Sheets, the ortho metalated compound may be treated with electrophiles such as trialkyltin halides providing the corresponding aryl stannanes which in turn are also useful intermediates in the production of biphenyls as reported by Stille, et al., J. Am. Chem. Soc., 1987, Vol. 109, page 5478-5486. Preparation of biphenyl intermediate A1-6 is accomplished in the Flow Sheets utilizing the Suzuki cross-coupling procedure and the appropriately adorned aryl compounds A1-4 and A1-5. The Suzuki coupling can be generally described as the reaction of an aryl boronic acid with an aryl halide or halide equivalent employing tetrakis(triphenylphosphine) palladium(0) catalyst in the presence of an aqueous solution of sodium carbonate in the solvents toluene/ethanol. The resulting biphenyl compound is isolated by standard methods. Compound A1-5 may itself be produced by standard methods to obtain the halogen substitution, X, the amino moiety —NR'$_2$ and the desired substituents $R^a$ or their precursors. The preferred halogen X is bromine, iodine or the halogen equivalent trifluoromethanesulfonyloxy. The preferred amino moiety, —NR'$_2$, may be any of —NO$_2$, —N$_3$, protected amine or amine, substituted with $R^b$ or its precursor. Biphenyl compound A1-6 is subsequently transformed into the halogenated biphenyl A1-7 via ipso substitution of the trimethylsilyl moiety in methylene chloride or other appropriate solvent employing iodine monochloride. Any number of halogenating reagents are suitable, such as IBr, NBS, I$_2$, Br$_2$, etc., which must be compatible with the already existing functionalities. Finally, the object compound, B1-1, is obtained via transamidization of the amino moiety with the latent carboxy precursor in the form of DMG.

Referring to Flow Sheet A2, the regioisomeric phenanthridone B1-2, may be produced in a manner analogous to that of phenanthridone B1-1. Compound A2-1 is dissimilar to compound A1-4 in that DMG of compound A2-1 is of the amino precursor type. Compound A2-1 is reacted with the appropriately adorned compound A2-2 to prepare biphenyl intermediate A2-3 utilizing the Suzuki cross-coupling procedure. As above biphenyl compound A2-3 is transformed into halogenated biphenyl via ipso substitution A2-4 and finally into object phenanthridone B1-2 via transamidization.

Presented with Flow Sheet A1 and A2, the skilled artisan will appreciate certain modification as possibly beneficial. In one modification, the ipso substitution of silicon to halogen might be performed after cyclization to form the object phenanthridone. In another modification, compounds A1-5 and A2-2 may be adorned utilizing a DMG substitutent replacing —NR'$_2$ and —CO$_2$Me respectively. As above, the DMG substituent directs adornment of $R^a$ or precursors thereof in manufacture. As above, the DMG should be of the carboxyl precursor type or amino precursor type as appropriate. In yet another modification, the oxocarbonyl of intermediate B1-1 or B1-2 can be converted to a thiocarbonyl to produce $X^h$ as S using Lawesson type reagents or by treating with phosphorus pentasulfide in an appropriate solvent. Another modification to produce $X^h$ as S is to employ a carbon based DMG wherein the oxocarbonyl moiety is replaced by thiocarbonyl. A suitable carbon based DMG containing thiocarbonyl is —(C=S)NH-phenyl. Although compounds in which $X^h$ is S are suitable, compounds in which $X^h$ is O are preferred.

Although the foregoing method to produce phenanthridones B1-1 or B1-2 is preferred herein, there are of course other appropriate methods. In one method, phenanthridone, produced by art known procedures, is brominated at the 2-position as taught by Mosby, W. L., J. Chem. Soc., Vol. 76, pp 936 (1954). The 2-bromophenanthridone may also be obtained by the procedure of Walls, L. P., J. Chem. Soc., pp. 1406 (1935). Preparation of N-substituted, 2-bromo-phenanthridones may be prepared as taught by Cookson, R. F., et al., J. Heterocycl. Chem., (1979) 9, 475. Substituted phenanthridones are prepared by Beckmann rearrangement of substituted 9-oxofluorene oximes by the method of Pan, H. -L., and Fletcher, T. L., J. Med. Chem., Vol. 12, pp. 822 (1969). Substituted phenanthridones are prepared by a Schmidt rearrangement of substituted 9-oxofluorene by the method of Pan, H. -L., and Fletcher, T. L., J. Heterocycl. Chem., Vol. 7, pp 313 (1970). Substituted phenanthridones are discussed generally by Keene, B.R.T. and Tissington, P., Adv. Hetercyclic Chem., Vol. 13, pp 315 (1971).

FLOW SHEET A1

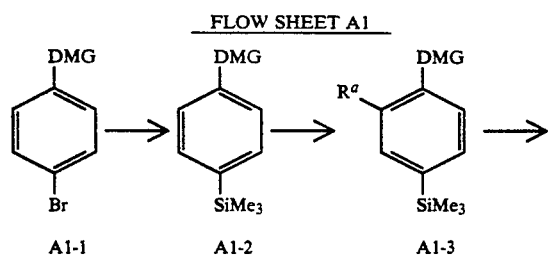

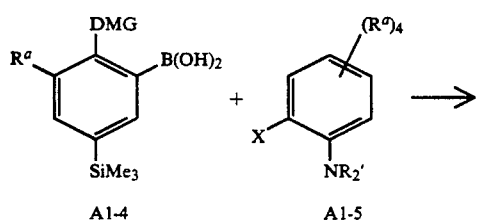

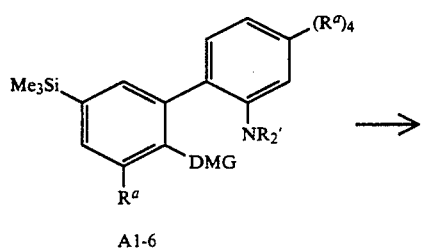

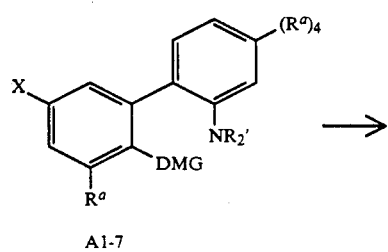

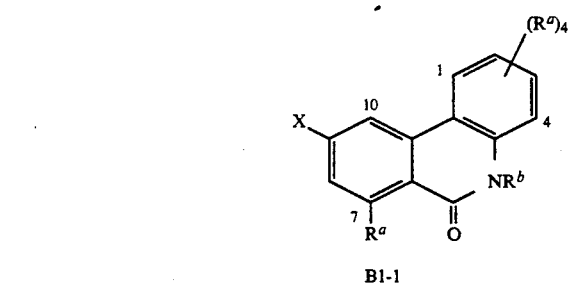

FLOW SHEET A2

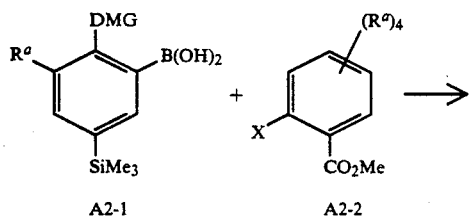

-continued
FLOW SHEET A2

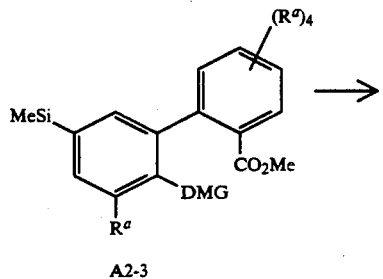

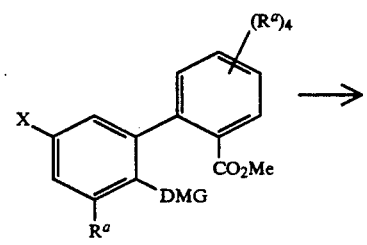

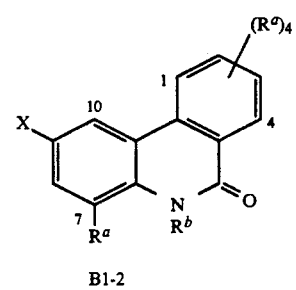

The object compound of Flows Sheet A1 and A2, phenanthridone B1-1 and B1-2, forms the nucleus of the 2-position substitution of the carbapenem compounds taught herein. As such it is shown to be $R^a$ and $R^b$ substituted. However, it is immediately clear to those skilled in the art that certain $R^a$ and $R^b$ listed above, if substituted on compounds A1-1, A1-5, A2-1 or A2-2 would not survive or permit the synthesis to compounds B1-1 or B1-2. Thus, where a certain $R^a$ or $R^b$ is desired on compound B1-1 or B1-2 and this $R^a$ or $R^b$ is not compatible with the synthesis scheme to produce, B1-1 or B1-2 then a compatible precursor substituent may be employed through the synthesis.

The identity of the precursor substituent employed is not crucial so long as it does not interfere with the synthesis to B1-1 or B1-2 and so long as it may be thereafter converted to more desireable substituent. Preferred precursor substituents for $R^a$ are methyl, hydroxymethyl and protected hydroxymethyl. Preferred precursor substituents for $R^b$ are 2-hydroxyethyl or protected 2-hydroxyethyl.

Thus, as to the $R^a$ substituent on compound B1-1 or B1-2, it may be an $R^a$ with or without protecting groups stable to the conditions of producing compound B1-1 or B1-2, and stable to the conditions of subsequently adding B1-1 or B1-2, to the carbapenem. Alternatively, it may be a stable precursor substituent which is stable to the conditions of making B1-1 or B1-2, which is optionally stable to the conditions of adding B1-1 or B1-2, to the carbapenem and which is convertible to a desired $R^a$ or to another precursor substituent.

As stated above, the second stage synthesis is to attach the base phenanthridone B1-1 or B1-2 to the 2-position of the carbapenem. With stable $R^a$ and $R^b$ or suitable precursor substituents therefor, phenanthridone B1-1 or B1-2 may be added to azetidin-2-one B2 in a Grignard reaction as shown in Flow Sheet B. The Grignard reaction requires that B1-1, for example, be converted to a Grignard reagent by reaction with magnesium and 1,2-dibromoethane in THF from 20° C. to 60° C. and subsequently contacting B1-1 as a Grignard reagent with B2 in THF at from −70° C. to about 20° C. to produce azetidin-2-one B3. Alternatively, B1-1 may be reacted with t-butyllithium, n-butyllithium, or the like in THF at from −78° to −50° C. followed by the addition of magnesium bromide to produce the same Grignard reagent. $R^1$ of B3 is in practice pyrid-2-yl but may clearly be a variety of substituents including aromatic and heteroaromatic substituents. Further $R^i$ might be for example phenyl, 2-pyrimidinyl or 2-thiazolyl.

Azetidin-2-one B3 is an intermediate that may be ring closed to a carbapenem. It is on this intermediate that $R^a$, $R^b$ or precursor substituents may be modified where such modification is incompatible with the carbapenem nucleus.

Compound B3 may be ring closed to carbapenem B4 by refluxing in xylene with a trace of p-hydroquinone for about 1 to 2 hours in an inert atmosphere. It is on this intermediate that final elaboration of $R^a$ from a precursor substituent, e.g. hydroxymethyl, may be accomplished. Removal of the carboxyl and hydroxyl protecting groups then provides the final compound of Formula I. Such final elaboration and deprotection is described in further detail below.

FLOW SHEET B

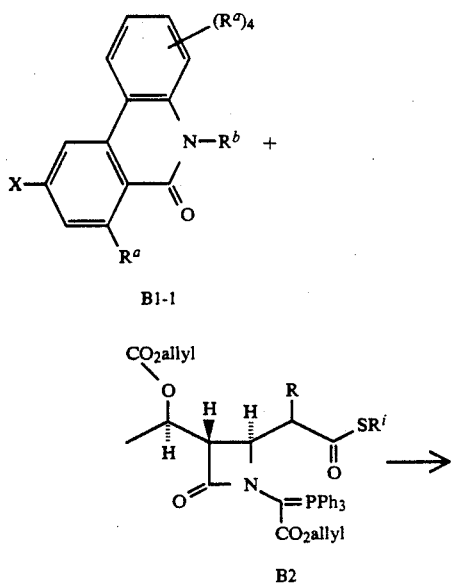

-continued
FLOW SHEET B

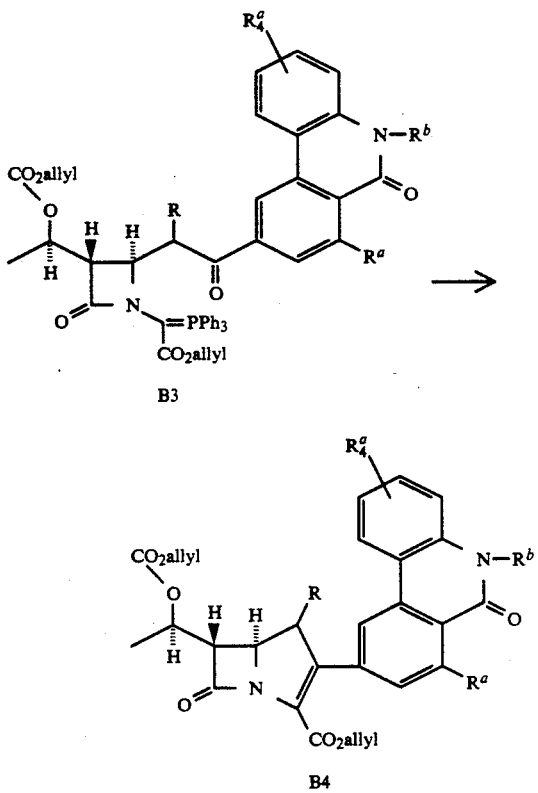

Flow Sheet C shows an alternative preferred second stage synthesis, i.e. attachment of the base phenanthridone such as B1-1 to the 2-position of the carbapenem. This synthesis involves a palladium catalyzed cross-coupling reaction between a carbapenem triflate and a suitably substituted arylstannane, a process which is described in U.S. patent application Ser. No. 485,096 filed Feb. 26, 1990, hereby incorporated by reference. In order to apply this synthesis, it is first necessary to modify phenanthridone B1-1 to the trimethylstannyl-phenanthridone C3. This is accomplished by reacting B1-1 with t-butyllithium in THF at from −78° to −50° C. followed by the addition of trimethyltin chloride. Preferably, phenanthridone B1-1 may be reacted with hexamethylditin in the presence of a palladium(O) catalyst such as tetrakis(triphenylphosphine)palladium(O) in an inert solvent such as toluene at from 25° to 110° C. for from 0.25-24 hours to provide the same stannane C3. Referring to Flow Sheet C, the 2-oxocarbapenam C1 is reacted with a suitable trifluoromethanesulfonyl source, such as trifluoromethanesulfonic anhydride, trifluoromethanesulfonyl chloride and the like, in the presence of an organic nitrogen base, such as triethylamine, diisopropylamine and the like, in polar aprotic solvent, such as tetrahydrofuran or methylene chloride. Optionally, an organic nitrogen base, such as triethylamine and the like, is then added to the reaction solution followed immediately by a silylating agent, such as trimethylsilyl trifluoromethanesulfonate to provide intermediate C2. An aprotic polar coordinating solvent, such as DMF, 1-methyl-2-pyrrolidinone and the like, is added. This is followed by the addition of a palladium compound, such as tris(dibenzylideneacetone)dipalladium-chloroform, palladium acetate and the like, optionally, a suitably substituted phenylphosphine, such as tris(4-methoxyphenyl)phosphine, tris(2,4,6-trimethoxythe final compound of Formula I. Such final elaboration and deprotection is described in further detail below.

FLOW SHEET C

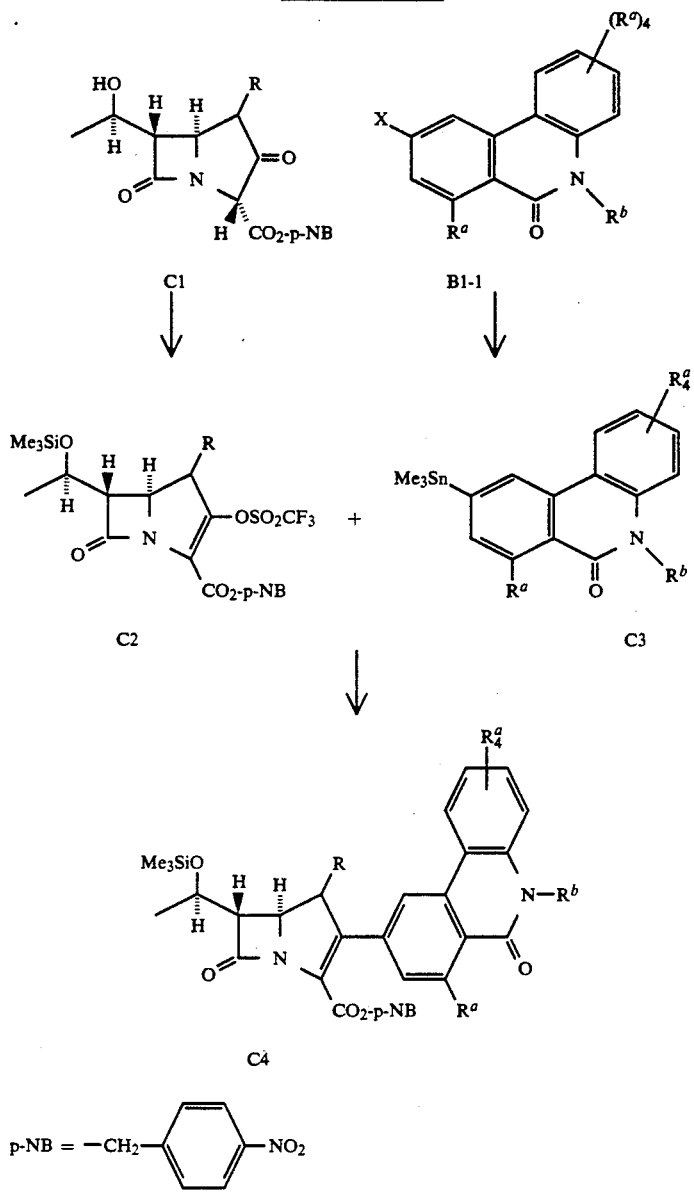

p-NB = —CH$_2$—<phenyl>—NO$_2$ phenyl)phosphine and the like, and the stannane C3. A halide source, such as lithium chloride, zinc chloride or ammonium chlorides and the like, is added and the reaction solution is allowed to warm and is stirred at a suitable temperature, such as 0° to 50° C. for from a few minutes to 48 hours. The carbapenem C4 is obtained by conventional isolation/purification methodology known in the art.

Generally speaking, the milder conditions of the synthesis shown in Flow Sheet C allow for a wider range of functional groups $R^a$ or $R^b$ to be present than the synthesis illustrated in Flow Sheet B. However, in certain cases it is advantageous for the $R^a$ or $R^b$ substituent(s) of the stannane C3 to be introduced in a protected or precursory form. Final elaboration of $R^a$ or $R^b$ from a precursor substituent, e.g. hydroxymethyl, may be accomplished on carbapenem intermediate C4. Removal of hydroxyl and carboxyl protecting groups then provides Azetidin-2-one B2, a pyridyl-thioester, is a well known compound in the production of carbapenems. Diverse synthetic schemes useful to make B2 may be imagined by the skilled artisan. Particularly useful to the instant invention is a synthetic scheme set out further in Flow Sheet D below in which the symbol R is as defined above. The steps for preparing intermediate B2 are analogous to the procedures described, for example, in U.S. Pat. Nos. 4,260,627 and 4,543,257; L. D. Cama et al. *Tetrahedron* 39, 2531 (1983); R. N. Guthikonda et al. *J. Med. Chem.*, 30, 871 (1987) hereby incorporated by reference.

FLOW SHEET D

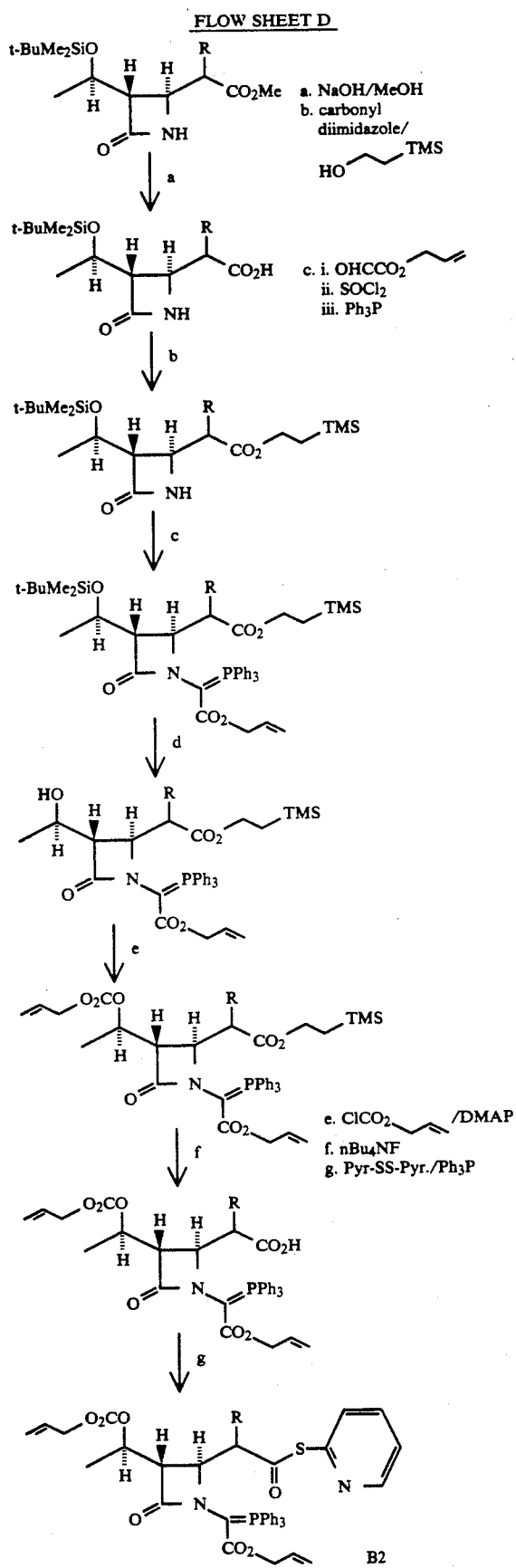

The steps for preparing the 2-oxocarbapenam intermediate C1 are well known in the art and are explained in ample detail by D. G. Melillo et al., *Tetrahedron Letters*, 21, 2783 (1980), T. Salzmann et al., *J. Am. Chem. Soc.*, 102, 6161 (1980), and L. M. Fuentes, I. Shinkai, and T. N. Salzmann, *J. Am. Chem. Soc.*, 108, 4675 (1986). The syntheses are also disclosed in U.S. Pat. Nos. 4,269,772, 4,350,631, 4,383,946 and 4,414,155 all assigned to Merck and Company, Inc. and hereby incorporated by reference.

The general synthesis description depicted above in the Flow Sheets shows a protected 1-hydroxyethyl substitution on the 6-position of the carbapenem. After final deprotection, a 1-hydroxyethyl substituent is obtained, which is preferred in most cases. However, it has been found that with certain 2-side-chain selections, the ultimate balance of favorable properties in the overall molecule may be enhanced by selection of the 6-(1-fluoroethyl) moiety instead. Preparation of 6-fluoroalkyl compounds within the scope of the present invention is carried out in a straightforward manner using techniques well known in the art of preparing carbapenem antibacterial compounds. See, e.g., J. G. deVries et al., *Heterocycles*, 23 (8), 1915 (1985); BE 900 718 A (Sandoz) and Japanese Patent Pub. No. 6-0163-882-A (Sanraku Ocean).

In the compounds of the present invention, one of the $R^a$ or $R^b$ substituents must be of Type I. As a general matter, it is conjectured that anti-MRSA/MRCNS activity results from the configuration of the overall molecule uniquely conferred by the phenanthridone nucleus. The Type I substituent provides still greater anti-MRSA/MRCNS activity to the molecule.

The Type II $R^a$ substituents are distinguishable from Type I substituents chemically and with respect to the biological properties which they confer. In related compounds, it has been found that the Type II substituted compounds afford greater water solubility and reduced potential for CNS side effects. Substituents which tend to confer improved water solubility on the overall compound have been found useful, since they are contemplated to thereby improve the transport of the compound involved. Although a substantial number and range of Type II substituents have been described herein, all of these are contemplated to be a part of the present invention based on the biological performance of substituents related in terms of their medicinal chemistry.

Since it is possible to combine, in the compounds of the present invention, the required Type I substituents with the optional Type II substituents, there can be obtained a combination of desired attributes in the final overall molecule not attainable with a single substituent, i.e., improved anti-MRSA/MRCNS activity together with enhanced water solubility.

Type I substituents employed in the compounds of the present invention may have quaternary nitrogen groups, and these include both cyclic and acyclic types, as is described under Type I. As already pointed out above, it is required that one, but no more than one, of the substituents $R^a$ and $R^b$ must be a member selected from the group consisting of the definitions under Type I. It is optional that one, or at most three, of the remaining substituents may be a member selected from the group consisting of definitions under Type II. For example, $R^a$ at the 3-position may be Type I and $R^a$ at the 7-position may be of Type II, while the remaining substituents are hydrogen.

In preferred compounds of Formula I, $R^1$ is hydrogen. More preferably, $R^1$ is hydrogen and $R^2$ is (R)—CH₃CH(OH)— or (R)—CH₃CH(F)—. In the most preferred case, $R^1$ is hydrogen and $R^2$ is (R)—CH₃CH(OH)—. While R=H is usually preferred, there are instances in which R=CH₃ may provide improved chemical stability, water solubility, or pharmacokinetic behavior. The substituent R=CH₃ may be of either configuration, i.e., the α or β-stereoisomer. Additionally, in preferred compounds, at least $R^a$ in the 3- or 7-position of the phenanthridone is other than hydrogen. In the most preferred compounds, in total, two $R^a$ and $R^b$ substituents are other than hydrogen.

Preferred Type I. a) substituents include:

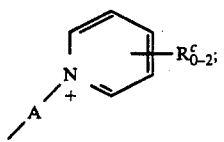 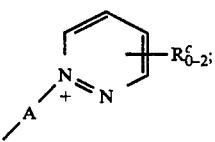

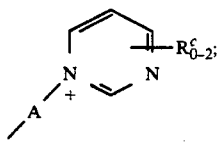 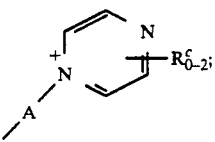

where the ring contains three carbon atoms ;

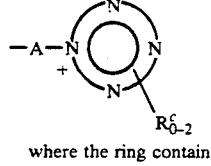
where the ring contains two carbon atoms ;

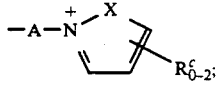 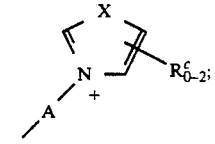

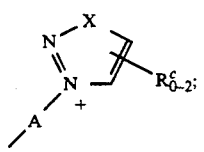 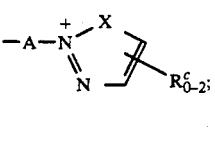

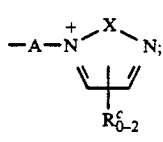 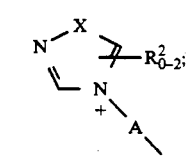

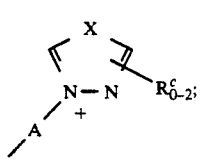 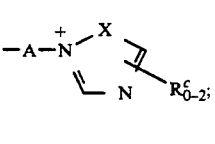

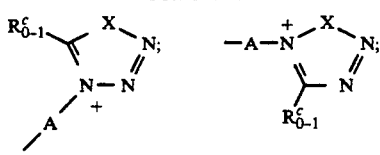

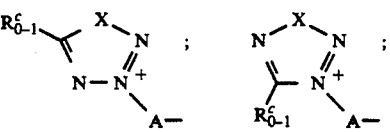

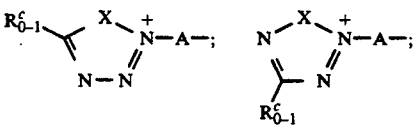

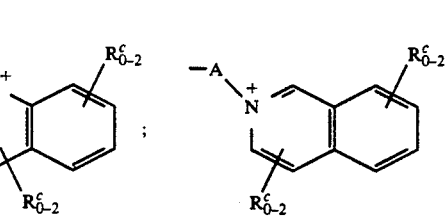

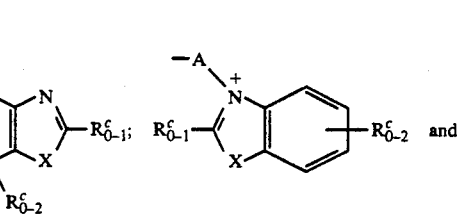

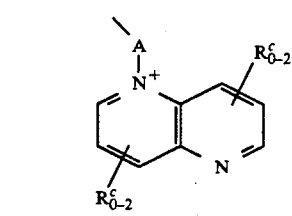

where X=O, S, or $NR^c$. For structures of Type I. a), where $R^c$ is shown to have an indefinite position, it may be attached to any carbon of the ring.

Preferred Type I.b) substituents include:

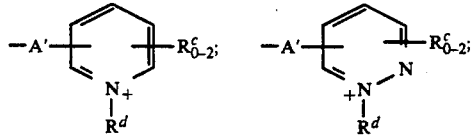

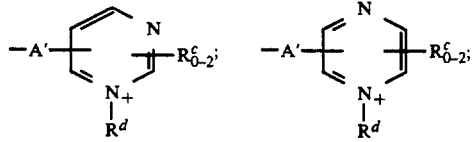

-continued

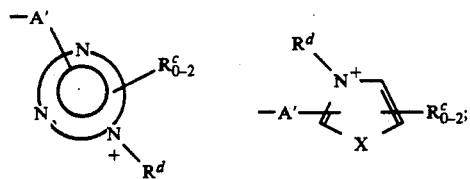

where the ring contains three carbon atoms ;

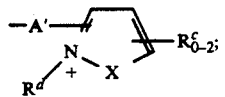

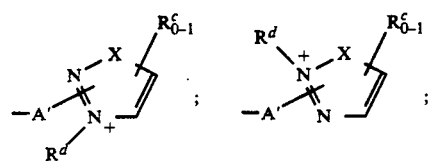

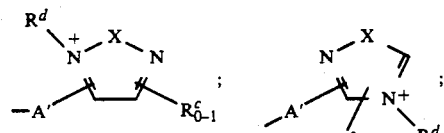

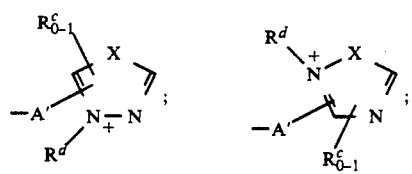

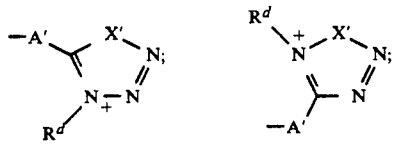

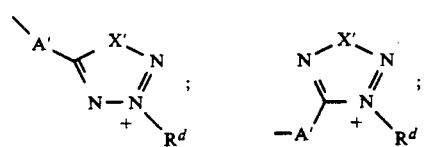

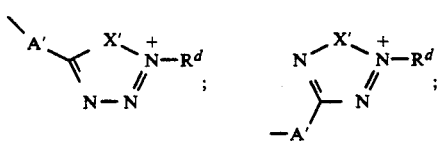

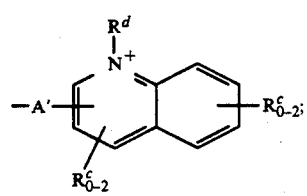

-continued

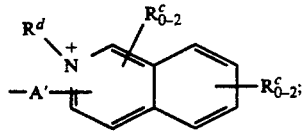

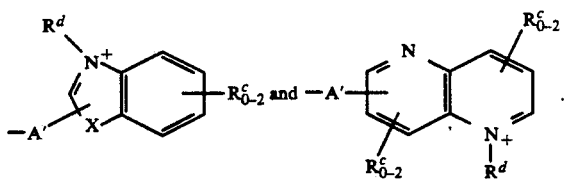

where X=O, S, or NR$^c$ and X'=O or S. For structures of Type I. b), where R$^c$ and/or A' are shown to have indefinite positions, they are independently attached to any carbon atom of the ring.

Preferred Type I. c) substituents include:

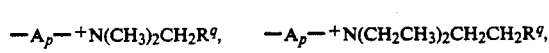

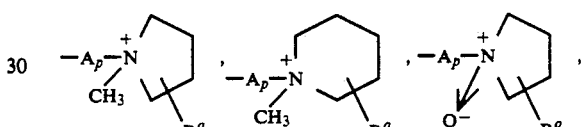

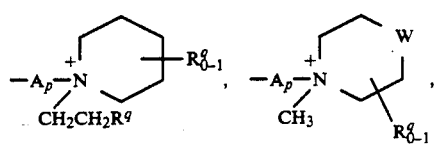

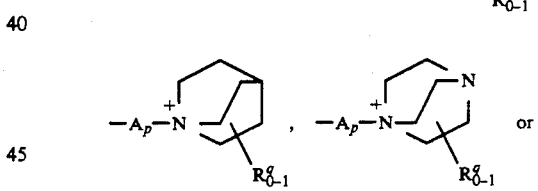

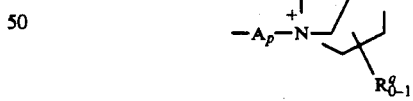

where W is O, S, NR$^e$, N(O)R$^e$, SO, SO$_2$ or N$^+$(R$^e$)$_2$ and W' is N$^+$R$^e$ or NO. For structures of Type I.c), where R$^q$ is shown to have an indefinite position, it may be attached to any carbon atom of the ring.

Preferred Type I. d) substituents include:

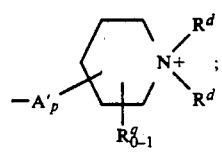

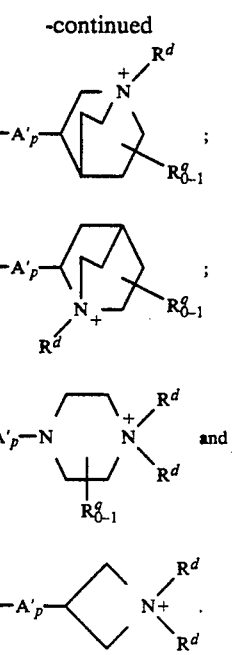

For structures of Type I.d), where $R^q$ and/or $A'_p$ is shown to have an indefinite position, it may be attached to any carbon atom of the ring.

The $R^c$ substituents herein are intended to represent suitable further substituents on the Type I. a) or b) substituents for the phenanthridonyl ring. As seen above, these Type I. a) or b) substituents are monocyclic or bicyclic aromatic groups containing heteroatoms. Given this class of primary substituent, further suitable substituents may be readily discovered in the penem and carbapenem art. For example, suitable substituents for Type I. a) or b) substituents are generally taught in U.S. Pat. No. 4,729,993 assigned to Merck and Co. or in U.S. Pat. No. 4,746,736 assigned to Bristol-Myers Co. These patents are hereby incorporated by reference.

Broadly, $R^c$ may be the same or different and may be selected on an independent basis from the group as defined above. While a single such substitution is preferred, there is occasion to use up to two such substituents on an $R^a$, e.g., where it is desired to enhance the effect of a particular substituent group by employing multiple substituents. The particular choice of $R^c$ will depend upon the situation. For instance, a specific $R^c$ may lend particular stability to a nitrogen cation. At other times it may be desired to employ a substituent known to enhance antibacterial activity of the overall molecule against a particular bacterium, for example, while also employing a substituent known to improve some other property such as water solubility or the duration of action of the overall molecule.

The scope of $R^c$ herein includes two specific Types of further substituent attached to the Type I. a) or b) substituent. A first Type of $R^c$ are those attached to a ring carbon and a second Type of $R^c$ are those attached to a neutral ring nitrogen. Persons skilled in the art will readily recognize that a wide range of organic substituents are suitably used as $R^c$. Persons skilled in the art will also recognize that some substituents including the $-NR^yR^z$ substituents, useful for one purpose of $R^c$, i.e. carbon substitution, are not equally useful in the other, i.e. nitrogen substitution.

Preferred $R^c$ attached to ring carbon atoms are $-NH_2$, $-SCH_3$, $-SOCH_3$, $-CH_2OH$, $-(CH_2)_2OH$, $-OCH_3$, $-COOM^b$, $-CH_2COOM^b$, $-CH_2CH_2COOM^b$, $-CH_2SOCH_3$, $-CH_2SCH_3$, $-SO_3M^b$, $-CH_2SO_3M^b$, $-CH_2CH_2SO_3M^b$, $-Br$, $-Cl$, $-F$, $-I$, $-CH_3$, $CH_2CH_3$, $CH_2CONH_2$ and $CH_2CON(C_1-C_4$ alkyl) where $M^b$ is defined above. Preferred $R^c$ attached to neutral ring nitrogen atoms are $-CH_2OH$, $-(CH_2)_2OH$, $-CH_2COOM^b$, $-CH_2CH_2COOM^b$, $-CH_2SOCH_3$, $-CH_2SCH_3$, $-CH_2SO_3M^b$, $-CH_2CH_2SO_3M^b$, $-CH_3$, $CH_2CH_3$, $CH_2CPNH_2$ and $CH_2CON(C_1-C_4$alkyl) where $M^b$ is defined above.

It is preferred that each Type I. a) or b) substituent have no more than two $R^c$ substituents which are other than hydrogen. Thus, the formula shown above for Type I. a) substituents has up to two $R^c$ substituents with the remainder of course being hydrogen. Further, the formula for the Type I. b) substituent also allows up to two $R^c$. In accordance with these formulae, the previously listed more specific structures should be interpreted to have no more than two $R^c$ for each monocyclic or bicyclic group. Similarly for Type I. c) or d) substituents it is preferred that any monocylic or bicyclic group have no more than a single $R^q$ substituent.

The scope of $R^d$ includes a single type of further substituent attached a Type I. b) or d) substituent. The $R^d$ substituents are attached to a cationic nitrogen which may or may not be aromatic. Preferred $R^d$ attached to cationic nitrogen atoms are hydrogen, $-CH_3$, $CH_2CH_3$, $-CH_2CH_2CH_3$, $-CH_2COOM^b$, $-CH_2SO_3M^b$, $-NH_2$ and $O^{(-)}$, where $M^b$ is defined above.

The formulas depicting Type Ib, Ic, and Id substituents show positively charged states for those substituents. It is understood that certain of those substituents, which are cationic by virtue of having a protonating hydrogen atom attached to the nitrogen, may also exist or be produced under certain conditions as a neutral substituent by virtue of the absence of such a hydrogen atom (i.e. in Type Ib, when there is no $R^d$; in Type Ic, when there is no $R^w$; and in Type Id, when there is zero to one $R^d$, depending on Type of heterocycle). Whether such a Type Ib, Ic, or Id substituent will be predominately cationic or neutral in a given physical state will be governed by principles of acid-base chemistry, which are well known to those skilled in the art. For example, the particular ratio of neutral form to cationic form will depend upon the basicity of the amine and acidity of a solution. When such a substituent is in a protonated quaternized state, the compound exists as a zwitterion which is internally balanced as to charge or as an ammonium salt which is externally balanced. In illustration, if there is no $R^d$ on a Type Ib substituent, it is understood that such a substituent is neutral (there is no positive charge on the nitrogen). A compound containing such a substituent is typically produced in this form as a salt, wherein M is an alkali metal, and may exist in solution in its neutral form. However, depending upon conditions, a compound containing a neutral Type Ib substituent may be in equilibrium with, and may also be represented by a formula showing, the corresponding compound containing the quaternized protonated substituent where $R^d$ is present and is a hydrogen atom. Furthermore the same compound may exist with the Type Ib substituent in a completely protonated quaternized form, for instance in an aqueous solution in the presence of a stoichiometric amount of a strong mineral acid. It is intended herein that both the protonated (cationic) and the unprotonated (neutral)

forms of Type Ib, Ic and Id substituents of the type just described are within the scope of the present invention.

Suitable A spacer moieties include —$CH_2$—, —$CH_2CH_2$—, —$CH_2CH_2CH_2$—, —$CH_2CH_2CH_2CH_2$—, —$OCH_2CH_2$—, —$SOCH_2$—, —$SO_2CH_2$—, —$SCH_2CH_2$—, —$SOCH_2CH_2$—, —$SO_2CH_2CH_2$—, —$NHCH_2CH_2$—, —$N(CH_3)CH_2CH_2$—, —$CH_2N(CH_3)CH_2CH_2$—, —$CONHCH_2CH_2$—, —$SO_2NHCH_2CH_2$—, —$COCH_2$—, —$CH=CHCH_2$— and —$CH_2OCH_2CH_2$—. Preferably, where Q is O, S, NH or N($C_{1-4}$alkyl), then n is 2–6.

Suitable A' are listed for A above. Further A' may suitably be —O—, —S—, —NH—, —$SO_2$—, —$SO_2NH$—, —CONH—, —CH=CH—, —$CH_2S$—, —$CH_2NH$—, —$CONHCH_2$— or —$SO_2NHCH_2$—.

The Type I. cationic substituents are generally added to the phenanthridone following attachment of the phenanthridone to the carbapenem. Conveniently, the phenanthridone side-chain should be synthesized with a precursor substituent which may be elaborated into the desired cationic substituent. The identity of the precursor substituent will vary according to the particular $R^a$ or $R^b$ desired. For example, one such precursor substituent is —A—OH, such as hydroxymethyl.

The hydroxymethyl precursor substituent may be elaborated into cationic substituents of Type I.a) by converting the hydroxyl into an active leaving group such as an iodide (giving —A—I) followed by reaction with a desired nitrogen containing aromatic compound. More particularly, two alternative procedures may be utilized to produce a leaving group on the moiety —A— and subsequently to replace such a leaving group with cationic substituents of the type just described.

For a first procedure, the hydroxyl group of —A—OH may be converted to a methanesulfonate group by treating with methanesulfonyl chloride in the presence of triethylamine. A suitable solvent, e.g., dichloromethane, is employed and the reaction is carried out at reduced temperatures. In turn, the methanesulfonate intermediate which itself is a good leaving group may be converted to the reactive iodide derivative by treatment with sodium iodide in a suitable solvent, e.g., acetone, at reduced or ambient temperatures. Alternatively, the hydroxyl group may be directly converted into the iodide group by common methods known to the art. For example, treatment of the hydroxyl group with methyl triphenoxyphosphonium iodide in a suitable solvent, such as dimethylformamide, at reduced or ambient temperatures, directly provides the desired iodide. Once the iodide has been formed, the introduction of the cationic substituent is accomplished simply by treating the iodide with the desired nitrogen containing compound, e.g. a heteroaromatic compound such as pyridine. The reaction will proceed in a suitable solvent, such as acetonitrile, at or about room temperature. This displacement reaction may also be facilitated by the addition of excess silver trifluoromethanesulfonate to the reaction mixture, in which case reduced temperatures are often desireable.

For a second procedure, the hydroxyl group of —A—OH may be converted into the reactive trifluoromethanesulfonate (triflate) group. However, such an activating group cannot be isolated by conventional techniques but may be formed and used in situ. Thus, treatment of the hydroxyl group with trifluoromethanesulfonic (triflic) anhydride in the presence of a hindered, non-nucleophilic base such as 2,6-lutidine, 2,4,6-collidine, or 2,6-di-tert-butyl-4-methylpyridine in a suitable solvent, such as dichloromethane, at reduced temperatures provides for the generation of the triflate activating group. Introduction of the cationic group is then accomplished by reacting the above triflate in situ with the desired nitrogen containing compound at reduced temperature. In certain cases it is possible and desireable to use the reacting nitrogen containing compound as the base for the formation of the triflate activating group. In this case treatment of the hydroxyl group with triflic anhydride in the presence of at least two equivalents of the reacting nitrogen compound under the conditions described above provides the cationic substituent.

The above are representative of suitable leaving groups: alkylsulfonyloxy, substituted alkylsulfonyloxy, arylsulfonyloxy, substituted arylsulfonyloxy, fluorosulfonyloxy and halogen. The common sulfonate leaving groups are: methanesulfonyloxy, trifluoromethanesulfonyloxy, fluorosulfonyloxy, p-toluenesulfonyloxy, 2,4,6-tri-isopropylbenzenesulfonyloxy, p-bromobenzenesulfonyloxy and p-nitrobenzenesulfonyloxy. The preferred halo leaving groups are bromo and iodo. These alkyl and arylsulfonate leaving groups may be prepared using an analogous route to the one described above using the sulfonyl chloride or the sulfonic anhydride.

Where the cationic substitution has a substituent $R^c$, the most facile method of providing such a substituent is to employ as the reactant in the preparation methods described above a nitrogen containing compound which already has the desired substituent. Such substituted compounds are readily available starting materials or may be prepared in a straight-forward manner using known literature methods.

The Type I.b) cationic substituents are prepared by quaternization of an aromatic ring nitrogen of a neutral precursor substituent on the phenanthridone ring. Examples of neutral precursor substituents are —$CONHCH_2$—(2-pyridyl), —$CONHCH_2$—(4-pyridyl) or —$SO_2CH_2$—(4-pyridyl). Quaternization is accomplished by reacting the nitrogen compound in an inert organic solvent (e.g.$CH_2Cl_2$) at about 0° C. to room temperature with an alkylating agent $R^d$—Y where $R^d$ is given above and Y is a leaving group such as iodide, bromide, mesylate (methanesulfonate), tosylate (p-toluenesulfonate) or triflate. Alternatively, the aromatic ring nitrogen may be quaternized by reaction with an oxidizing agent such as 3-chloroperbenzoic acid (giving the N-oxide) or an amidinating reagent such as o-(2,4,6-triisopropylbenzenesulfonyl)hydroxylamine (giving the N-amino derivative) in a suitable solvent (e.g. dichloromethane or $CH_3CN$) at about room temperature. In addition, the neutral precursor substituent may be rendered cationic through protonation of the basic aromatic ring nitrogen. This may be accomplished by treatment of the neutral precursor with a suitable inorganic or organic acid, e.g. hydrochloric acid, phosphoric acid, hydrobromic acid, acetic acid or benzoic acid. Protonation may further be accomplished by a carboxylic acid function elsewhere in the molecule, including the C-3 carboxyl on the carbapenem. The neutral precursor substituent may be already attached to the phenanthridone ring at the time of its connection to the carbapenem, or it may be elaborated from a simpler precursor after connection to the carbapenem. An example of a precursor substituent for elaboration is —A'—OH such as hydroxymethyl. In one suggested synthesis, the hydroxyl may be converted to a reactive leaving group such as iodo as described above. The iodide is then reacted in a nucleophilic displacement reaction with a nitrogen containing aromatic compound which has a nucleophilic side-chain substituent such as $CH_2SH$ or $CH_2NH_2$. In this displacement reaction, it is the side-chain substituent that is the reacting nucleophile and not the aromatic ring nitrogen. Suitable substrates for this reaction include 2-(mercaptomethyl)-pyridine, 2-aminopyridine, 2-(aminomethyl)pyridine or 4-(mercaptomethyl)pyridine. The reaction is carried-out in an inert organic solvent, e.g. methylene chloride, at from about 0° C. to room temperature in the presence of a non-nucleophilic base such as triethylamine or diisopropylethylamine. Quaternization or protonation of the aromatic ring nitrogen as described above then gives the Type I.b) cationic substituent. A second suggested synthesis of a Type I.b) cationic substituent starting from a precursor —A'—OH (e.g. hydroxymethyl) consists of oxidation of the alcohol functionallity to an aldehyde followed by Wittig-type olefination with an appropriate nitrogen-containing aromatic substituted reagent, and finally quaternization. The oxidation may be conveniently accomplished by a Swern oxidation employing oxalyl chloride-dimethylsulfoxide followed by triethylamine. The reaction is conducted in methylene chloride as a solvent at from −70° C. to 0° C. The Wittig reaction is carried-out by reacting the aldehyde with the desired Wittig reagent in a polar solvent such as acetonitrile or dimethylsulfoxide at about room temperature. Suitable Wittig reagents include: pyridylmethylenetriphenylphosphorane, quinolylmethylenetriphenylphosphorane, and thiazolylmethylenetriphenylphosphorane. Quaternization or protonation as described above then completes the synthesis of the Type I.b) cationic substituent. Depending on the particular $R^a$ of Type I.b) that is desired, many other synthesis schemes may be employed, as would be apparent to an organic chemist skilled in the art.

The Type I.c) cationic substituents may be prepared in an analogous manner to that described for I.a) substituents except that the nitrogen containing compound employed in the displacement reaction is an aliphatic amine (i.e. $NR^yR^zR^w$). However, in cases where the amino group is directly bonded to the phenanthridone nucleus (i.e. $—A_pN^+R^yR^zR^w$ where p=0) the amine is most conveniently attached to the phenanthridone prior to its incorporation into the carbapenem system. If such an amine is primary or secondary, it may require protection with a suitable amine protecting group during the steps employed to attach the phenanthridone to the carbapenem. Tertiary amines require no protection and may be quaternized or protonated as described for the Type I.b) cationic substituents.

The Type I.d) cationic substituents are prepared by quaternization or protonation of a non-aromatic ring nitrogen of an appropriate neutral precursor substituent on the phenanthridone ring. Quaternization or protonation is accomplished as described above for the Type I.b) substituents. As with the Type I.b) substituents, the neutral precursor may already be attached to the phenanthridone ring at the time of its connection to the carbapenem, or the neutral precursor may be elaborated from a simpler precursor substituent on the phenanthridone ring after its connection to the carbapenem. Examples of neutral precursor substituents are: —CONH(3-quinuclidinyl), —CONH[4-(N-methylpiperidinyl)], —SO$_2$CH$_2$CH$_2$[2-(N-methylpyrrolidinyl)], —SO$_2$NH[1-(4-methylpiperazinyl)] and —CH$_2$[1-(4-methylpiperazinyl)]. Elaboration of the neutral precursor substituent from a simpler substituent such as hydroxymethyl may be accomplished in an analogous manner to that described previously for the Type I.b) substituents by employing appropriate reagents to introduce the Type I.d) non-aromatic ring nitrogen moiety which is subsequently to be quaternized or protonated.

It should be clear that for any of the Type I.a) to I.d) substituents, that the substituent may be suitably formed on the phenanthridone prior to addition to the carbapenem. Thus, the substituent may be formed on C3 and reacted with C2 to form the protected carbapenem C4. For example, 3-hydroxymethyl-9-trimethylstannyl-phenanthridone, i.e. C3, may be substituted by reaction with triflic anhydride and N-methylimidazole in a suitable solvent, such as, dichloromethane under nitrogen at −78° C. to room temperature to form a Type I.a) substituted phenanthridone, i.e. C3. This substituted phenanthridone may be reacted with C2 employing conditions otherwise described herein and specifically using an ammonium chloride source.

Suitable $R^a$ and $R^b$ are described above in the text associated with Formula I. Among preferred $R^a$ of Type II are $C_{1-4}$ alkyl mono-substituted with hydroxy, such as, hydroxymethyl; formyl; alkoxycarbonyl, such as, —COOCH$_3$; carbamoyl, such as, —CONH$_2$; hydroximinomethyl, such as, —CH=NOH or cyano. Among preferred $R^b$ are hydroxymethyl, hydroxyethyl, —CH$_2$CHO, —CH$_2$COOCH$_3$, —CH$_2$CONH$_2$, —CH$_2$CH=NOH and —CH$_2$CN.

In regard to this preferred substitution, a hydroxyethyl group may be obtained for $R^b$ of the phenanthridone as shown in Flow Sheets A1 and A2. In Flow Sheet A1, for instance, compound A1-5 may be substituted with —NH(CH$_2$CH$_2$OH) or its appropriately protected equivalent where an appropriate protecting group is for example t-butyldiphenylsilyl. Alternatively, for instance, in Flow Sheet A2, the DMG group might be —NH('BOC) which is removed under acidic conditions from compound A2-4 which subsequently cyclizes to compound B1-2 where $R^b$ is hydrogen. The nitrogen moiety of compound B1-2 may be alkylated using sodium hydride in appropriate solvent with 2-bromo-t-butyldiphenylsilylethanol to obtain $R^b$ as protected hydroxyethyl. A hydroxymethyl may be obtained in any of positions 7, 1, 2, 3 or 4 for $R^a$ as follows. As one method, hydroxymethyl may be substituted on any of rings A1-4 and A1-5 or A2-1 and A2-2 by standard procedures and appropriately protected. Alternatively, methyl, as a precursor substituent, is substituted on starting materials A1-4 and A1-5 or A2-1 and A2-2 in the appropriate positions by well know means and the starting materials reacted to a corresponding methyl-substituted B1-1 or B1-2 according the Flow Sheet A. Subsequently, the methyl substituent(s) of methyl-substituted B1-1 or B1-2 may be oxidized to bromomethyl with N-bromosuccinimide. This oxidation of the precursor substituent, methyl, is advantageously performed prior to substituting the phenanthridone on the azetidin-2-one as the oxidizing conditions are incompatible with either the azetidin-2-one or the subsequent carbapenem. In the case of the bromomethyl substituent, conversion to an hydroxymethyl substituted B1-1 or B1-2 may be accomplished by a three-step sequence. Reaction of the bromomethyl compound with potassium acetate in DMF at 80° C. gives the corresponding acetoxymethyl compound. Removal of the acetate group, e.g. by hydrolysis with methanolic sodium hydroxide or by reduction with diisobutylaluminium hydride in THF, gives the hydroxymethyl substituted compound B1-1 or B1-2. Further elaboration of of hydroxymethyl substituted B1-1 or B1-2 according to Flow Sheet B produces a corresponding B3 and B4.

The preferred formyl substitution on the phenanthridone may be obtained on B4 from the hydroxymethyl substitution, in the case of $R^a$, or hydroxyethyl substitution in the case of $R^b$, by a Swern oxidation. For example, B4 is oxidized in methylene chloride at from $-70°$ C. to room temperature employing oxalyl chloride-dimethyl sulfoxide followed by triethylamine as the active agent. Obviously, the position of the resultant formyl substitution will depend upon the position of the hydroxymethyl or hydroxyethyl substitution B4.

The preferred —CH=NOH substitution on the phenanthridone may be conveniently obtained from the formyl substitution just described. This is accomplished simply by exposing the formyl substituted compound to hydroxylamine in an appropriate solvent at room temperature.

The preferred cyano substitution on the phenanthridone may be obtained from the —CH=NOH substitution just described. The —CH=NOH substituted compound is dehydrated with triflic anhydride and triethylamine in a solvent at $-70°$ C.

The —COOCH₃ substitution on the phenanthridone may be obtained from the hydroxymethyl or hydroxyethyl substituted B3 described above. For example, compound B3 is oxidized with Jones reagent to convert the hydroxymethyl substituent to the carboxylic acid group. The oxidation with Jones reagent may be incompatible with the carbapenem and thus is optimally performed before ring closure. Prior to ring closure, the carboxylic acid group is esterified by sequentially contacting with 1-ethyl-3-(3-dimethyl-aminopropyl)carbodiimide hydrochloride, 1-hydroxybenzotriazole, and methanol in an organic solvent at room temperature. Substituted esters may of course be obtained by replacing methanol with the corresponding substituted alcohol. Alternatively, a methyl substituted B1-1 or B1-2, as described above, may be oxidized with chromium trioxide or $^nBu_4NMnO_4$ to form carboxy.

The preferred carbamoyl substitution on the phenanthridone, may be obtained from B3 by oxidizing the hydroxymethyl or hydroxyethyl group with Jones reagent to the corresponding carboxylic acid group as described above. This carboxylic acid substituent is converted to the carboxamide group, —CONH₂, by sequentially contacting with 1-ethyl-3-(3-dimethylaminopropyl)carbodiimide hydrochloride, 1-hydroxybenzotriazole, and ammonia in an organic solvent at room temperature. Substituted amides may of course be obtained by replacing ammonia with the corresponding substituted amine. In contrast to the carboxyl substitution, this carbamoyl group requires no protection for the conditions of carbapenem cyclization.

Compounds substituted with the preferred $R^a$ and $R^b$ of Type II just described may also be obtained by employing the synthesis shown in Flow Sheet C. In this case, the synthetic transformation just described may be carried-out on intermediate C3 prior to attachment of the phenanthridone side chain to the carbapenem or on C4 after such attachment.

In addition to or including the above, suitable $R^a$ of Type II include:

| | |
|---|---|
| —OCH₃ | —OCH₂CO₂CH₃ |
| —OCH₂CH₂OH | —CF₃ |
| —F | —Cl |
| —Br | —I |
| —OH | —OCOCH₃ |
| —OCONH₂ | —SCH₃ |
| —SOCH₃ | —SO₂CH₃ |
| —SCH₂CH₂OH | —SOCH₂CH₂OH |
| —SO₂NH₂ | —SO₂N(CH₃)₂ |
| —NHCHO | —NHCOCH₃ |
| —NHCO₂CH₃ | —NHSO₂CH₃ |
| —CN | —CHO |
| —COCH₃ | —COCH₂OH |
| —CH=NOH | —CH=NOCH₃ |
| —CH=NOCH₂CO₂CH₃ | —CH=NOCMe₂CO₂CH₃ |
| —CH=NOCMe₂CONH₂ | —CO₂CH₂CH₂OH |
| —CONH₂ | —CONHCH₃ |
| —CON(CH₃)₂ | —CONHCH₂CN |
| —CONHCH₂CONH₂ | —CONHCH₂CO₂CH₃ |
| —CONHOH | —CONHOCH₃ |
| -tetrazolyl | —CO₂CH₃ |
| —SCF₃ | —PO₂NH₂ |
| —CONHSO₂Ph | —CONHSO₂NH₂ |
| —SO₂CF₃ | —SO₂NHCN |
| —SO₂NHCONH₂ | —CH=CHCN |
| —CH=CHCONH₂ | —CH=CHCO₂CH₃ |
| —C≡C—CONH₂ | —C≡C—CN |
| —CH₂OH | —CH₂N₃ |
| —CH₂CO₂CH₃ | —SO₂CH₂CH₂OH |
| —SCH₂CONH₂ and | —CH₂I. |

In addition to or including the above, suitable $R^b$ of Type II include:

| | |
|---|---|
| —CH₂OCH₃ | —CH₂OCH₂CO₂CH₃ |
| —CH₂OCH₂CH₂OH | —CH₂CF₃ |
| —CH₂CH₂F | —CH₂CH₂Cl |
| —CH₂CH₂Br | —CH₂CH₂I |
| —CH₂OH | —CH₂OCOCH₃ |
| —CH₂OCONH₂ | —CH₂SCH₃ |
| —CH₂SOCH₃ | —CH₂SO₂CH₃ |
| —CH₂SCH₂CH₂OH | —CH₂SOCH₂CH₂OH |
| —CH₂SO₂NH₂ | —SO₂N(CH₃)₂ |
| —CH₂CH₂NHCHO | —CH₂CH₂NHCOCH₃ |
| —CH₂CH₂NHCO₂CH₃ | —CH₂CH₂NHSO₂CH₃ |
| —CH₂CN | —CH₂CHO |
| —CH₂COCH₃ | —CH₂COCH₂OH |
| —CH₂CH=NOH | —CH₂CH=NOCH₃ |
| —CH₂CH=NOCH₂CO₂CH₃ | —CH₂CH=NOCMe₂CO₂CH₃ |
| —CH₂CH=NOCMe₂CONH₂ | —CH₂CO₂CH₂CH₂OH |
| —CH₂CONH₂ | —CH₂CONHCH₃ |
| —CH₂CON(CH₃)₂ | —CH₂CONHCH₂CN |
| —CH₂CONHCH₂CONH₂ | —CH₂CONHCH₂CO₂CH₃ |
| —CH₂CONHOH | —CH₂CONHOCH₃ |
| —CH₂tetrazolyl | —CH₂CO₂CH₃ |
| —CH₂SCF₃ | —CH₂PO₂NH₂ |
| —CH₂CONHSO₂Ph | —CH₂CONHSO₂NH₂ |
| —CH₂SO₂CF₃ | —CH₂SO₂NHCN |
| —CH₂SO₂NHCONH₂ | —CH₂CH=CHCN |
| —CH₂CH=CHCONH₂ | —CH₂CH=CHCO₂CH₃ |
| —CH₂C≡C—CONH₂ | —CH₂C≡C—CN |
| —CH₂CH₂OH | —CH₂CH₂N₃ |
| —CH₂CH₂CO₂CH₃ | —CH₂SO₂CH₂CH₂OH |
| —CH₂SCH₂CONH₂ | —OH |
| —OCH₃ | —CF₃ |
| —SO₂CH₃ | —SO₂NH₂, and |
| —NH₂. | |

In the preparation methods described above, the carboxyl group at the 3-position and the hydroxyl group at the 8-position of the carbapenem remain blocked by protecting groups until the penultimate product is prepared. Suitable hydroxyl protecting groups, P', are silyl groups such as trialkylsilyl, aryl(alkyl)alkoxysilyl, alkloxydiarylsilyl and diarylalkylsilyl and carbonate groups such as alkyloxy and substituted alkyloxycarbonyl, benzyloxycarbonyl, substituted benzyloxycarbonyl, allyloxycarbonyl and substituted allyloxycarbonyl. The preferred protecting groups, in addition to or including those shown in the schemes, are t-butylmethoxyphenylsilyl, t-butoxydiphenylsilyl, trimethylsilyl, triethylsilyl, t-butyldimethylsilyl, o-nitrobenzyloxycarbonyl, p-nitrobenzyloxycarbonyl, benzyloxycarbonyl, t-butyloxycarbonyl, 2,2,2-trichloroethyloxycarbonyl and allyloxycarbonyl. Suitable carboxyl protecting groups M, in addition to or including those shown in the schemes are described herein below.

Deblocking may be carried out in a conventional manner. For compounds prepared according to Flow Sheet B, deprotection may be carried out in a palladium catalyzed reaction in a solution containing potassium 2-ethylhexanoate and 2-ethylhexanoic acid or, alternatively, another suitable nucleophile such as pyrrolidine. Alternatively, for those prepared via Flow Sheet C, deprotection is conducted sequentially. Thus, compound C4 is exposed initially to aqueous acidic conditions, acetic acid or dilute HCl or the like, in an organic solvent such as tetrahydrofuran containing some $H_2O$ at 0° C. to ambient temperature for from a few minutes to several hours. The resulting desilylated carbapenem may be isolated by conventional techniques, but is more conveniently taken into the final deprotection process. Thus, addition of an inorganic base such as $NaHCO_3$ or $KHCO_3$ and 10% Pd/C followed by hydrogenation provides for the removal of the p-nitrobenzyl protecting group and the formation of the final compound of Formula I.

The overall molecule must be electronically balanced. Since a quaternary nitrogen is present in the compounds of the present invention, a balancing anion must also, in that case, be present. This is usually accomplished by allowing COOM to be $COO^-$. However, where M is, e.g., a pharmaceutically acceptable ester, a counterion (anion) $Z^-$ must be provided, or alternatively, an anionic substituent might be utilized. A counterion must also be provided or additional anionic substituent utilized where there is more than one quaternary nitrogen. Further, it is within the scope of this invention to utilize an anionic substituent where the quaternary nitrogen is already balanced by COOM=$COO^{31}$. In that case, it will be understood that it is necessary to provide a counterion (cation) for the anionic substituent. However, it is well within the skill of a medicinal chemist, to whom there is available many suitable anionic and cationic counterions, to make such choices.

With reference to the above definitions, "alkyl" means a straight or branched chain aliphatic hydrocarbon radical.

The term "quaternary nitrogen" as used herein refers to a tetravalent cationic nitrogen atom including the cationic nitrogen atom in a tetra-alkylammonium group (e.g. tetramethylammonium, N-methylpyridinium), the cationic nitrogen atom in a protonated ammonium species (e.g. trimethyl-hydroammonium, N-hydropyridinium), the cationic nitrogen atom in an amine N-oxide (e.g. N-methylmorpholine-N-oxide, pyridine-N-oxide), and the cationic nitrogen atom in an N-amino-ammonium group (e.g. N-aminopyridinium).

The term "heteroatom" means N, S, or O, selected on an independent basis.

The term "heteroaryl" has been defined herein, in relation to the $R^x$ group, to have a specific and limited meaning, being only monocyclic. While the cationic groups I. a) and b) also clearly include heteroaryl groups, being both monocyclic and bicyclic, the term "heteroaryl" has not been used in association with the definitions of those cationic groups above. It is required that the monocyclic heteroaryl have at least one nitrogen atom, and optionally at most only one additional oxygen or sulfur heteroatom may be present. Heteroaryls of this type are pyrrole and pyridine (1N); and oxazole, thiazole or oxazine (1N+1 O or 1 S). While additional nitrogen atoms may be present together with the first nitrogen and oxygen or sulfur, giving, e.g., a thiadiazole (2N's+1S), the preferred heteroaryls are those where only nitrogen heteroatoms are present when there is more than one. Typical of these are pyrazole, imidazole, pyrimidine and pyrazine (2N's) and triazine (3N's).

The heteroaryl group of $R^x$ is always optionally mono-substituted by $R^q$, defined above, and substitution can be on one of the carbon atoms or one of the heteroatoms, although in the latter case certain substitutent choices may not be appropriate.

Listed in Table I are specific compounds of the instant invention:

TABLE I

[Structure diagram: carbapenem core with R', R substituents, COOM group, and A substituent] where R' is F or OH, R is H or Me and A is:

[Two biphenyl-type structures with positions 1-4, 7, 10 labeled, $(R^a)_4$ substituents, one with $N-R^b$ and carbonyl, the other with =O and $N-R^b$]

| M | $R^a$ or $R^b$ | Position |
|---|---|---|
| (−) | $-CH_2N^+$-pyridinyl-$NH_2$ | 7-$R^a$ |
| (−) | $-CH_2N^+$-pyridinyl-$NH_2$ | 3-$R^a$ |
| (−) | $-CH_2N^+$-pyridinyl-$NH_2$ | 4-$R^a$ |

TABLE I-continued

Structure: β-lactam fused bicyclic core with R' (isopropyl-bearing substituent), H, H, R substituents, A group, and COOM, where R' is F or OH, R is H or Me and A is:

Biaryl/tricyclic A groups with positions 1,2,3,4 on one ring, 7,10 on the other, bearing $(R^a)_4$ substituents and either N—$R^b$ with C=O, or C=O with N—$R^b$.

| (—) | $-CH_2CH_2\overset{+}{N}{=}\!\langle\text{pyridine}\rangle\!-NH_2$ | $R^b$ |
| (—) | $-CH_2\overset{+}{N}{=}\!\langle\text{pyridine-3-NH}_2\rangle$ | 3-$R^a$ |
| (—) | $-CH_2\overset{+}{N}{=}\!\langle\text{pyridine-4-NH}_2\rangle$ | 7-$R^a$ |
| (—) | $-CH_2\overset{+}{N}{=}\!\langle\text{pyridine-4-NH}_2\rangle$ | 3-$R^a$ |
| (—) | $-CH_2\overset{+}{N}{=}\!\langle\text{pyridine-4-NH}_2\rangle$ | 4-$R^a$ |
| (—) | $-CH_2CH_2\overset{+}{N}{=}\!\langle\text{pyridine-4-NH}_2\rangle$ | $R^b$ |
| (—) | $-CH_2\overset{+}{N}{=}\!\langle\text{pyridine-3-NH}_2\rangle$ | 7-$R^a$ |
| (—) | $-CH_2\overset{+}{N}{=}\!\langle\text{imidazole}\rangle\!-N-CH_3$ | 7-$R^a$ |
| (—) | $-CH_2\overset{+}{N}{=}\!\langle\text{imidazole}\rangle\!-N-CH_3$ | 3-$R^a$ |
| (—) | $-CH_2\overset{+}{N}{=}\!\langle\text{imidazole}\rangle\!-N-CH_3$ | 4-$R^a$ |
| (—) | $-CH_2CH_2\overset{+}{N}{=}\!\langle\text{imidazole}\rangle\!-N-CH_3$ | $R^b$ |
| (—) | $-CH_2\overset{+}{N}{=}\!\langle\text{triazole}\rangle\!-N-CH_3$ | 3-$R^a$ |
| (—) | $-CH_2CH_2\overset{+}{N}{=}\!\langle\text{triazole}\rangle\!-N-CH_3$ | $R^b$ |
| (—) | $-CH_2CH_2\overset{+}{N}{=}\!\langle\text{triazole}\rangle\!-N-CH_3$ | $R^b$ |
| (—) | $-CH_2\overset{+}{N}{=}\!\langle\text{imidazole}\rangle\!-NCH_2CONH_2$ | 7-$R^a$ |
| (—) | $-CH_2\overset{+}{N}{=}\!\langle\text{pyrazole-N-CH}_3\rangle$ | 3-$R^a$ |
| (—) | $-CH_2\overset{+}{N}{=}\!\langle\text{imidazole}\rangle\!-N-CH_2SOCH_3$ | 4-$R^a$ |
| K | $-CH_2\overset{+}{N}{=}\!\langle\text{imidazole}\rangle\!-NCH_2SO_3^-$ | 4-$R^a$ |
| (—) | $-CH_2\overset{+}{N}{=}\!\langle\text{triazole}\rangle\!-NCH_3$ | 4-$R^a$ |
| K | $-CH_2\overset{+}{N}{=}\!\langle\text{triazole}\rangle$ | 3-$R^a$ |

TABLE I-continued

Structure: bicyclic β-lactam with R' (isopropyl-like CH(CH3)), H, H, R substituents; C=O, N, A, COOM; where R' is F or OH, R is H or Me and A is:

Aryl groups:
- Biphenyl with numbering 1,2,3,4 (R^a)_4, 10, 7-R^a, and N—R^b amide
- Biphenyl with numbering 1,2,3,4 (R^a)_4, 10, 7-R^a, and C(=O)—N—R^b amide

| K | R^b |
|---|---|
| (−) | —CH$_2$CH$_2$N$^+$=pyridinium-CO$_2^-$ |
| (−) | —CH$_2$N$^+$=imidazolium—NCH$_2$CH$_2$OH, 4-R^a |
| (−) | —CH$_2$N$^+$=pyridinium-NH$_2$, 4-R^a |
| (−) | —CH$_2$N$^+$=pyridinium with CH$_2$S(O)CH$_3$ and NH$_2$, 4-R^a |
| (−) | —CH$_2$N$^+$=pyridinium with CH$_2$S(O)CH$_3$ and NH$_2$, 4-R^a |
| (−) | —CH$_2$N$^+$=pyridinium-CH$_2$OH, 4-R^a |
| (−) | —CH$_2$N$^+$=pyridinium with CH$_2$OH and NH$_2$, 4-R^a |
| (−) | —OCH$_2$CH$_2$N$^+$=pyridinium-NH$_2$, 4-R^a |
| (−) | —SCH$_2$CH$_2$N$^+$=pyridinium-NH$_2$, 4-R^a |
| (−) | —SO$_2$CH$_2$CH$_2$N$^+$=pyridinium-NH$_2$, 4-R^a |
| (−) | —CH$_2$OCH$_2$N$^+$=pyridinium-NH$_2$, 4-R^a |
| (−) | —CH$_2$SCH$_2$N$^+$=pyridinium-NH$_2$, 4-R^a |
| (−) | —CH$_2$S(O$_2$)CH$_2$N$^+$=pyridinium-NH$_2$, 4-R^a |
| (−) | —CH$_2$CH$_2$N$^+$=pyridinium-NH$_2$, 1-R^a |

TABLE I-continued

Structure: bicyclic β-lactam with R' (isopropyl-like substituent with H), R, and A substituent on ring bearing COOM; where R' is F or OH, R is H or Me and A is:

Aryl group options (two isomers shown): biphenyl-type system with positions 1,2,3,4,7,10 and (Rᵃ)₄ substituents, with N—Rᵇ amide variants.

| A group | Position |
|---|---|
| —C(O)NHCH₂CH₂CH₂—N⁺(pyridinium-2-NH₂) | 4-Rᵃ |
| —S(O)(OH)NCH₂CH₂—N⁺(pyridinium-2-NH₂) | 4-Rᵃ |
| —S—CH₂CH₂N⁺(N-methylimidazolium) | 7-Rᵃ |
| —C(O)NHCH₂CN₂—N⁺(N-methylimidazolium) | 3-Rᵃ |
| —CH₂S(O)₂CH₂N⁺(N-Me imidazolium) | Rᵇ |
| —CH₂S—(1-methylpyridinium-2-yl) | 3-Rᵃ |
| —CH=CH—(1-methylpyridinium-2-yl) | 3-Rᵃ |
| —NH—(2-pyridyl) | 3-Rᵃ |

Page 38 (right column):

| A group | Position |
|---|---|
| —CH₂C(O)NHCH₂—(1-methylpyridinium-2-yl) | Rᵇ |
| —CH₂C(O)NHCH₂CH₂—(1-methylpyridinium-4-yl) | Rᵇ |
| —CH₂S(O)₂CH₂CH₂—(1-methylpyridinium-2-yl) | Rᵇ |
| —CH₂—(1-methyl-2-amino-pyridinium-4-yl) | 3-Rᵃ |
| —CH₂—(1-carbamoylmethyl-pyridinium-4-yl) | 2-Rᵃ |
| —CH₂C(O)NHCH₂CH₂—(pyridine N-oxide-2-yl) (K) | Rᵇ |
| —CH₂S(O)₂CH₂—(pyridine N-oxide-4-yl) (K) | Rᵇ |
| —N⁺(CH₃)₂-pyrrolidinium | 3-Rᵃ |

TABLE I-continued

Structure: β-lactam fused bicyclic with R' (isopropyl-like with CH), R, A substituent, COOM group.

where R' is F or OH, R is H or Me and A is:

(Aryl-aryl system with positions 1-4, 7, 10, with (R$^a$)$_4$ substituents, N—R$^b$ amide, carbonyl — two tautomer/regiochemical options shown)

| M | R$^a$ | R$^a$ Position | R$^a$ or R$^b$ | Position |
|---|---|---|---|---|
| (−) | — | — | —CH$_2$—N$^+$(morpholine with CH$_3$) | 3-R$^a$ |
| (−) | — | — | —CH$_2$—N$^+$(CH$_3$)$_3$ | 4-R$^a$ |
| (−) | — | — | —CH$_2$—N$^+$ (quinuclidine) | 4-R$^a$ |
| K | — | — | —CH$_2$—N$^+$ (piperidine-CO$_2^-$) | 4-R$^a$ |
| K | — | — | —CH$_2$CH$_2$—N$^+$(morpholine N-oxide) | R$^b$ |
| (−) | — | — | —CH$_2$—N$^+$(piperazine N-oxide) | 3-R$^a$ |
| (−) | — | — | —C(O)NH—CH$_2$—(piperidine N$^+$(CH$_3$)$_2$) | 3-R$^a$ |
| (−) | CN | 7 | —CH$_2$N$^+$=CH—NCH$_3$ (imidazolium) | 3-R$^a$ |
| (−) | SOCH$_3$ | 7 | —CH$_2$N$^+$=CH—NCH$_3$ (imidazolium) | 3-R$^a$ |
| (−) | CO$_2$K | 7 | —CH$_2$N$^+$=CH—NCH$_3$ (imidazolium) | 3-R$^a$ |
| (−) | SO$_3$K | 7 | —CH$_2$N$^+$(pyridine-NH$_2$) | 3-R$^a$ |
| (−) | tetrazole-NK | 7 | —CH$_2$N$^+$(pyridine-NH$_2$) | 4-R$^a$ |
| (−) | SO$_2$CH$_3$ | 7 | —CH$_2$CH$_2$N$^+$(pyridine-NH$_2$) | R$^b$ |
| (−) | CN | 7 | —CH$_2$CH$_2$N$^+$=CH—NCH$_3$ (imidazolium) | R$^b$ |
| (−) | CONH$_2$ | 7 | —CH$_2$N$^+$=CH—NMe (imidazolium) | 3-R$^a$ |
| (−) | CONH$_2$ | 7 | —CH$_2$—N$^+$=CH—NMe (imidazolium) | 4-R$^a$ |
| (−) | N$^+$(CH$_3$)$_2$ pyrrolidinium | 7 | —CH$_2$CH$_2$CO$_2$Na | R$^b$ |
| Na | CN | 7 | —CH$_2$—N (imidazole) | 3-R$^a$ |
| (−) | SO$_3$K | 3 | —CH$_2$CH$_2$N$^+$(CH$_3$)(pyrrolidine) | R$^b$ |

TABLE I-continued

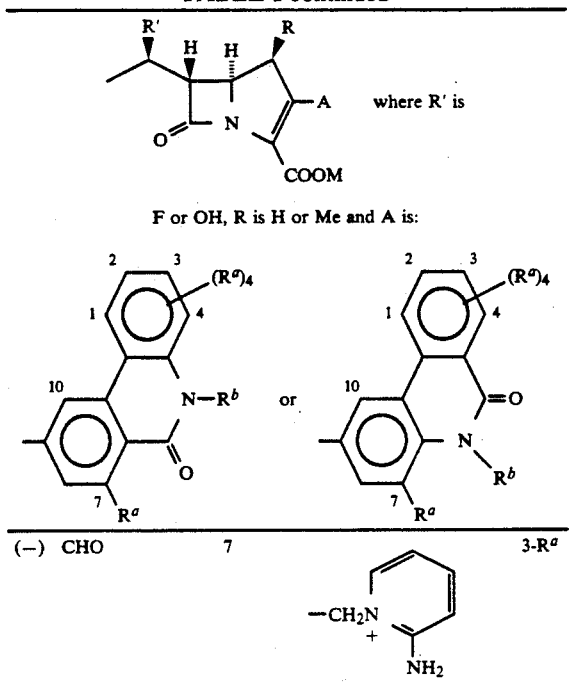

The carbapenem compounds of the present invention are useful per se and in their pharmaceutically acceptable salt and ester forms in the treatment of bacterial infections in animal and human subjects. The term "pharmaceutically acceptable ester or salt" refers to those salt and ester forms of the compounds of the present invention which would be apparent to the pharmaceutical chemist, i.e., those which are non-toxic and which would favorably affect the pharmacokinetic properties of said compounds, their palatability, absorption, distribution, metabolism and excretion. Other factors, more practical in nature, which are also important in the selection, are cost of the raw materials, ease of crystallization, yield, stability, hygroscopicity, and flowability of the resulting bulk drug. Conveniently, pharmaceutical compositions may be prepared from the active ingredients in combination with pharmaceutically acceptable carriers. Thus, the present invention is also concerned with pharmaceutical compositions and methods of treating bacterial infections utilizing as an active ingredient the novel carbapenem compounds of the present invention.

The pharmaceutically acceptable salts referred to above may take the form —COOM. The M may be an alkali metal cation such as sodium or potassium. Other pharmaceutically acceptable cations for M may be calcium, magnesium, zinc, ammonium, or alkylammonium cations such as tetramethylammonium, tetrabutylammonium, choline, triethylhydroammonium, meglumine, triethanolhydroammonium, etc.

The pharmaceutically acceptable salts referred to above may also include non-toxic acid addition salts. Thus, the Formula I compounds can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalene-sulfonate, nicotinate, oxalate, pamoate, pectinate, persulfate, 3-phenylpropionate, picrate, pivalate, propionate, succinate, tartrate, thiocyanate, tosylate, and undecanoate.

The pharmaceutical acceptable esters of the novel carbapenem compounds of the present invention are such as would be readily apparent to a medicinal chemist, and include, for example, those described in detail in U.S. Pat. No. 4,309,438, Column 9, line 61 to Column 12, line 51, which is incorporated herein by reference. Included within such pharmaceutically acceptable esters are those which are hydrolyzed under physiological conditions, such as pivaloyloxymethyl, acetoxymethyl, phthalidyl, indanyl and methoxymethyl, and those described in detail in U.S. Pat. No. 4,479,947, which is incorporated herein by reference.

The novel carbapenem compounds of the present invention may take the form COOM, where M is a readily removable carboxyl protecting group. Such conventional blocking groups consist of known ester groups which are used to protectively block the carboxyl group during the synthesis procedures described above. These conventional blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with a transition metal catalyst and a nucleophile, and catalytic hydrogenation. Broadly, such ester protecting groups include alkyl, substituted alkyl, benzyl, substituted benezyl, aryl, substituted aryl, allyl, substituted allyl and triorganosilyl. Examples of specific such ester protecting groups include benzhydryl, p-nitrobenzyl, 2-naphthylmethyl, allyl, 2-chloroallyl, benzyl, 2,2,2-trichloroethyl, trimethylsilyl, t-butyldimethylsilyl, t-butyldiphenylsilyl, 2-(trimethylsilyl)ethyl, phenacyl, p-methoxybenzyl, acetonyl, o-nitrobenzyl, p-methoxyphenyl, 4-pyridylmethyl and t-butyl.

The compounds of the present invention are valuable antibacterial agents active against various Gram-positive and to a lesser extent Gram-negative bacteria and accordingly find utility in human and veterinary medicine. The antibacterials of the invention are not limited to utility as medicaments; they may be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy or inhibit the growth of harmful bacteria on medical and dental equipment and as bactericides in industrial applications, for example in waterbased paints and in the white water of paper mills to inhibit the growth of harmful bacteria.

The compounds of this invention may be used in any of a variety of pharmaceutical preparations. They may be employed in capsule, powder form, in liquid solution, or in suspension. They may be administered by a variety of means; those of principal interest include: topically or parenterally by injection (intravenously or intramuscularly).

Compositions for injection, a preferred route of delivery, may be prepared in unit dosage form in ampules, or in multidose containers. The compositions may take such forms as suspensions, solutions, or emulsions in oily or aqueous vehicles, and may contain formulatory agents. Alternatively, the active ingredient may be in powder form for reconstitution, at the time of delivery, with a suitable vehicle, such as sterile water. Topical applications may be formulated in hydrophobic or hydrophilic bases as ointments, creams, lotions, paints, or powders.

The dosage to be administered depends to a large extent upon the condition and size of the subject being treated as well as the route and frequency of administration, the parenteral route by injection being preferred for generalized infections. Such matters, however, are left to the routine discretion of the therapist according to principles of treatment well known in the anti-bacterial art. Another factor influencing the precise dosage regimen, apart from the nature of the infection and peculiar identity of the individual being treated, is the molecular weight of the chosen species of this invention.

The compositions for human delivery per unit dosage, whether liquid or solid, may contain from 0.1% to 99% of active material, the preferred range being from about 10-60%. The composition will generally contain from about 15 mg to about 1500 mg of the active ingredient; however, in general, it is preferable to employ a dosage amount in the range of from about 250 mg to 1000 mg. In parenteral administration, the unit dosage is usually the pure compound I in sterile water solution or in the form of a soluble powder intended for solution.

The preferred method of administration of the Formula I antibacterial compounds is parenteral by i.v. infusion, i.v. bolus, or i.m. injection.

For adults, 5-50 mg of Formula I antibacterial compounds per kg of body weight given 2, 3, or 4 times per day is preferred. Preferred dosage is 250 mg to 1000 mg of the Formula I antibacterial given two (b.i.d.) three (t.i.d.) or four (q.i.d.) times per day. More specifically, for mild infections a dose of 250 mg t.i.d. or q.i.d. is recommended. For moderate infections against highly susceptible gram positive organisms a dose of 500 mg t.i.d. or q.i.d. is recommended. For severe, life-threatening infections against organisms at the upper limits of sensitivity to the antibiotic, a dose of 1000 mg t.i.d. or q.i.d. is recommended.

For children, a dose of 5-25 mg/kg of body weight given 2, 3, or 4 times per day is preferred; a dose of 10 mg/kg t.i.d. or q.i.d. is usually recommended.

Antibacterial compounds of Formula I are of the broad class known as carbapenems or 1-carbadethiapenems. Naturally occuring carbapenems are susceptible to attack by a renal enzyme known as dehydropeptidase (DHP). This attack or degradation may reduce the efficacy of the carbapenem antibacterial agent. The compounds of the present invention, on the other hand, are significantly less subject to such attack, and therefore may not require the use of a DHP inhibitor. However, such use is optional and contemplated to be part of the present invention. Inhibitors of DHP and their use with carbapenem antibacterial agents are disclosed in the prior art [see European Patent Applications No. 79102616.4 filed Jul. 24, 1979 (Patent No. 0 007 614); and No. 82107174.3, filed Aug. 9, 1982 (Publication No. 0 072 014)].

The compounds of the present invention may, where DHP inhibition is desired or necessary, be combined or used with the appropriate DHP inhibitor as described in the aforesaid patents and published application. Thus, to the extent that the cited European patent applications 1.) define the procedure for determining DHP susceptibility of the present carbapenems and 2.) disclose suitable inhibitors, combination compositions and methods of treatment, they are incorporated herein by reference. A preferred weight ratio of Formula I compound: DHP inhibitor in the combination compositions is about 1:1. A preferred DHP inhibitor is 7-(L-2-amino-2-carboxyethylthio)-2-(2,2-dimethylcyclopropanecarboxamide)-2-heptenoic acid or a useful salt thereof.

The second phenanthridone ring of formula I is not numbered in this text and claims as convention dictates. In the examples, conventional numbering of this ring is employed per the formula:

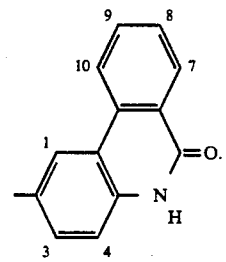

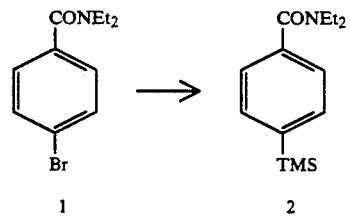

Chlorotrimethylsilane (10.4 mL, 81.9 mmol, 3.0 eq) was added to a stirred solution of 1 (7.0 g, 27.3 mmol) in dry THF (103 mL) at $-78°$ C. under $N_2$. Tert-butyllithium (23.1 mL, 30 mmol, 1.1 eq) was added dropwise at $-78°$ C. over 45 minutes. The reaction mixture was warmed to $0°$ C. with an ice bath and then quenched with saturated ammonium chloride solution (25 mL). After removal of THF in vacuo the reaction mixture was poured into ether (400 mL) and washed with water, saturated sodium bicarbonate solution (2×50 mL), water, and brine. The ethereal layer was dried ($MgSO_4$), filtered, and evaporated in vacuo. Purification using flash chromatography (20% EtOAc/hex) afforded 5.7 g (87%) of aryl silane 2, a white solid.

$^1$H-NMR for 2 [400 MHz, $CDCl_3$, rotamers]: δ0.24 (s, 9H), 1.08 (broad s, 3H), 1.21 (broad s, 3H), 3.23 (broad s, 2H), 3.51 (broad s, 2H), 7.30 (d, J=8.1 Hz, 2H), 7.50 (d, J=8.1 Hz, 2H).

IR($CHCl_3$): 3010, 1615 $cm^{-1}$.

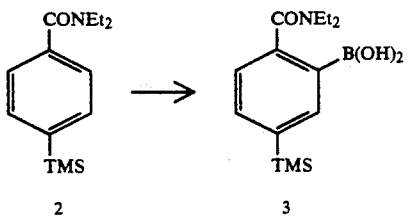

To a stirred solution of N,N,N',N'-tetramethylethylenediamine (2.7 mL, 17.6 mmol, 1.1 eq) in anhydrous THF (100 mL) at −78° C. under N₂ was added dropwise sec-butyllithium (13.0 mL, 16.8 mmol, 1.05 eq). After 15 minutes the yellow mixture was treated with a solution of 2 (4.0 g, 16.0 mmol) in dry THF (40 mL), and the resultant red mixture was stirred for 1 hour at −78° C. Trimethylborate (2.0 mL, 17.6 mmol, 1.1 eq) was added dropwise. The reaction flask was warmed to 0° C. with an ice bath and then stirred for 5 minutes. The green reaction mixture was quenched with 8% HCl solution (60 mL), stirred for 10 minutes, and the organic solvent concentrated in vacuo. The mixture was poured into ether and the ethereal layer was washed with water (2×), brine, dried (MgSO₄), filtered, and evaporated in vacuo. Purification using flash chromatography (5:3:1 EtOAc/acetone/H₂O) provided 3.77 g (80%) of boronic acid 3, a white foam.

¹H-NMR for 3 [200 MHz, CDCl₃, rotamers]: δ0.27 (s, 9H), 0.88 to 1.16 (m, 6H), 3.27 to 3.36 (m, 4H), 7.28 (d, J=6.4 Hz, 1H), 7.52 (d, J=7.6 Hz, 1H), 8.15 (s, 1H). IR(CHCl₃): 2960, 1615, 1601 cm⁻¹.

EXAMPLE 3

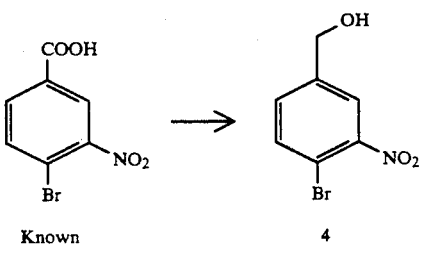

To a stirred solution of known bromo-nitrobenzoic acid (5.0 g, 20.3 mmol) in dry THF (40.6 mL) under N₂ at room temperature was added dropwise the borane-tetrahydrofuran complex (40.6 mL, 40.6 mmol, 2.0 eq). After stirring at reflux for 1 hour the reaction mixture was quenched with dropwise addition of triethylamine (1 mL) in methanol (50 mL) at 0° C. The solvent was then removed in vacuo to give crude 4. Purification using flash chromatography (30% EtOAc/hex) provided 4.5 g (96%) of 4, an off-white solid.

¹H-NMR for 4 [400 MHz, CDCl₃]: δ1.86 (t, J=5.8 Hz, 1H), 4.74 (d, J=5.8 Hz, 2H), 7.41 (dd, J=8.3, 2.1 Hz, 1H), 7.70 (d, J=8.3 Hz, 1H), 7.85 (s, 1H).

IR(CHCl₃): 3605, 3500 to 3200, 3010, 2880, 1605, 1535, 1355 cm⁻¹.

EXAMPLE 4

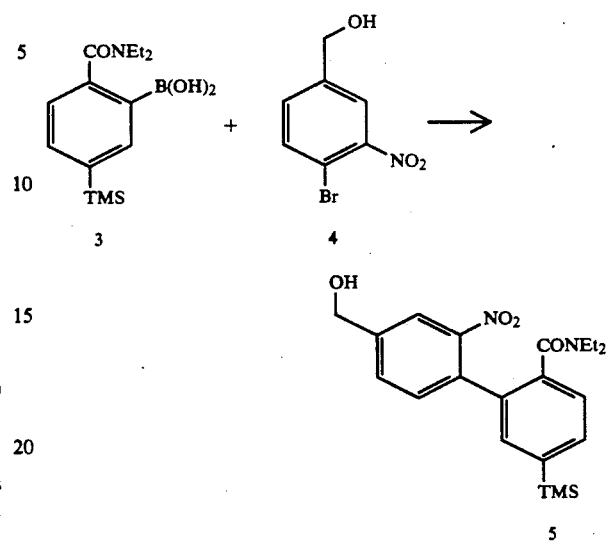

Aqueous sodium carbonate (8.7 mL, 17.4 mmol, 2.0 eq) was added to a stirred solution of 3 (2.0 g, 8.7 mmol) and tetrakis(triphenylphosphine) palladium (0) (502.8 mg, 5.0 mol %) in toluene (33.5 mL). The resulting two-phase mixture was stirred for 10 minutes under N₂ at room temperature. A solution of 4 (2.8 g, 9.6 mmol, 1.1 eq) dissolved in absolute ethanol (9.6 mL) was added, and the heterogeneous mixture was stirred for 3 hours at reflux under N₂. The cooled reaction mixture was poured into ether (175 mL) and washed with water (1×), saturated sodium carbonate solution (2×25 mL), water (1×), and brine. The organic layer was dried (MgSO₄), filtered, and evaporated in vacuo. Purification using flash chromatography (60% EtOAc/hex) provided 2.9 g (83%) of the biphenyl compound 5, a yellow foam.

¹H-NMR for 5 [400 MHz, CDCl₃, rotamers]: δ0.24 (s, 9H), 0.87 (t, J=7.1 Hz, 3H), 0.94 (t, J=7.1 Hz, 3H), 2.40 (broad s, 1H), 2.72 to 3.65 (broad, 4H), 4.76 (s, 2H), 7.30 to 7.32 (m, 2H), 7.51 to 7.56 (m, 3H), 7.93 (s, 1H).

IR(CHCl₃): 3360, 3520 to 3300, 2990, 1620, 1605, 1530 cm⁻¹.

EXAMPLE 5

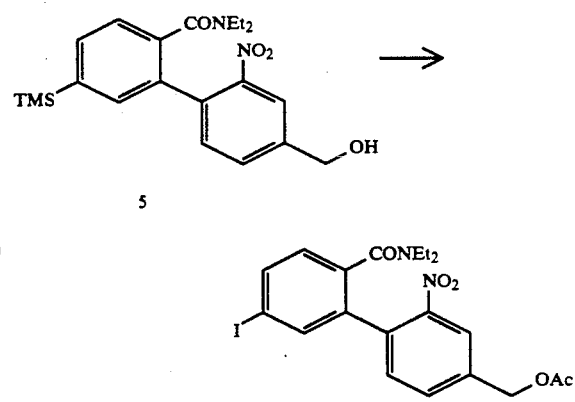

Acetic anhydride (6.8 mL, 72.4 mmol, 10.0 eq) was added to a stirred solution of 5 (2.9 g, 7.24 mmol) in dry pyridine (36 mL). The reaction mixture was stirred for 25 minutes at room temperature under $N_2$. The solvent was removed in vacuo and the residual oil azeotroped from toluene. The crude acetate was redissolved in dry dichloromethane (20 mL), and a 1.0M solution of iodine monochloride in dichloromethane (33 mL, 33.3 mmol, 4.6 eq) was added dropwise over 1 hour using an addition funnel. The reaction mixture was then poured into ether (250 mL) and the organic layer was washed with saturated sodium thiosulfate solution (3×30 mL), water (1×), saturated sodium bicarbonate solution (1×30 mL), water (1×), and brine. The organic layer was dried (MgSO$_4$), filtered, and evaporated in vacuo to afford 3.6 g (quantitative yield) of 6, a yellow oil.

$^1$H-NMR for 6 [400 MHz, CDCl$_3$, rotamers]: δ0.81 (t, J=7.1 Hz, 3H), 0.98 (t, J=7.1 Hz, 3H), 2.14 (s, 3H), 2.78 to 3.65 (broad, 4H), 5.17 (s, 2H), 7.08 (d, J=8.1 Hz, 1H), 7.49 to 7.61 (m, 3H), 7.76 (d, J=8.0 Hz, 1H), 7.97 (s, 1H).

IR(CHCl$_3$): 3010, 1745, 1610, 1530 cm$^{-1}$.

EXAMPLE 6

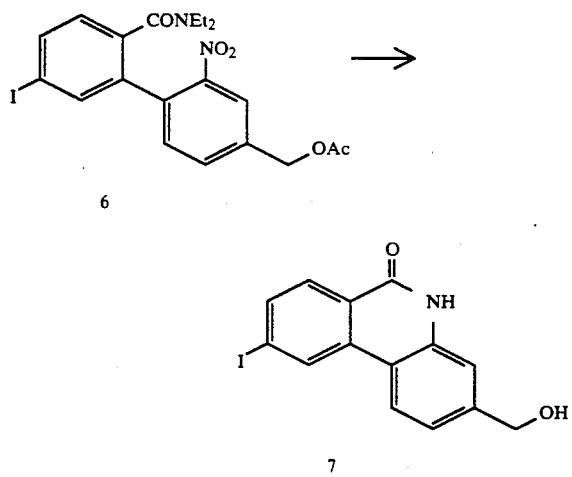

A solution of 25% sodium methoxide in methanol (0.53 mL, 2.4 mmol, 1.1 eq) was added to a stirred solution of 6 (1.1 g, 2.2 mmol) in dry methanol (11.0 mL). The reaction mixture was stirred for 10 minutes at room temperature under $N_2$. Acetic acid (6.0 mL) and dry tetrahydrofuran (11.0 mL) were then added. Iron powder (371.9 mg, 6.7 mmol, 3.0 eq) was added next, and the reaction mixture was stirred at reflux until a white solid had separated (approximately 15 minutes). The reaction mixture was cooled, poured into ice water (250 mL), and the solid filtered. The crude cyclized product was redissolved in hot ethanol (250 mL), filtered through a hot-sintered glass funnel, and the solvent removed in vacuo. Recrystallization from ethanol provided 501 mg (64%) of the cyclized amide 7, a white fluffy solid.

$^1$H-NMR for 7 [400 MHz, D$_6$ DMSO]: δ4.57 (s, 2H), 5.36 (t, J=5.7 Hz, 1H), 7.16 (d, J=8.2 Hz, 1H), 7.33 (s, 1H), 7.93 (d, J=8.4 Hz, 1H), 8.00 (d, J=8.4 Hz, 1H), 8.35 (d, J=8.4 Hz, 1H), 8.85 (s,1H), 11.74 (s,1H).

IR (KBr): 1670, 1601 cm$^{-1}$.

EXAMPLE 7

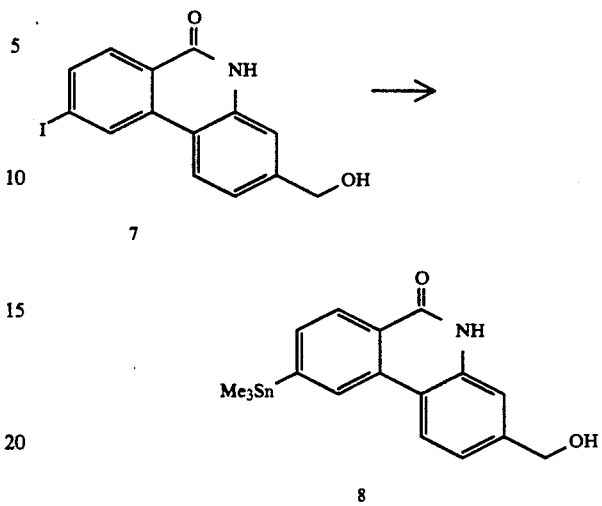

To a suspension of 7 (457 mg, 1.3 mmol) in toluene (45 mL) under $N_2$ was added hexamethylditin (0.28 mL, 1.43 mmol, 1.1 eq), tetrakis (triphenylphosphine) palladium (0) (75 mg, 5.0 mol %), and triphenylphosphine (10.2 mg, 3.0 mol %). After bubbling $N_2$ through the reaction mixture for 15 minutes, the reaction was heated to reflux for 1 hour under $N_2$. The reaction mixture was cooled, poured into ethyl acetate (175 mL), and washed with saturated sodium bicarbonate solution (2×25 mL), water (2×), and brine. The organic layer was dried (MgSO$_4$), filtered, and evaporated in vacuo. Recrystallization from acetone/hexane provided 469 mg (93%) of stannane 8, a white powder.

$^1$H-NMR for 8 [400 MHz, D$_6$ DMSO]: δ0.37 (s,9H), 4.56 (s, 2H), 5.34 (t, J=5.7 Hz, 1H), 7.18 (d, J=8.3 Hz, 1H), 7.33 (s, 1H), 7.72 (d, J=7.7 Hz, 1H), 8.21 (d, J=7.7 Hz, 1H), 8.39 (d, J=8.4 Hz, 1H), 8.55 (s, 1H), 11.63 (s, 1H).

IR(KBr): 1650, 1601, 1540 cm$^{-1}$.

EXAMPLE 8

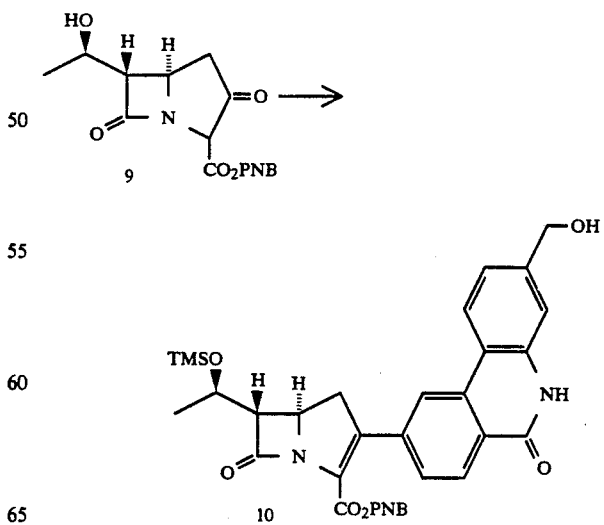

To a stirred solution of the bicyclic β-keto ester 9 (288.1 mg, 0.83 mmol) in dry THF (4.1 mL) at −78° C.

under N₂ was added diisopropylamine (129.0 μL, 0.91 mmol, 1.1 eq). The resultant yellow mixture was stirred for 10 minutes before trifluoromethanesulfonic anhydride (153.0 μL, 0.91 mmol, 1.1 eq) was added. After 15 minutes triethylamine (127.0 μL, 0.91 mmol, 1.1 eq), followed by the trimethylsilyl trifluoromethanesulfonate (176.0 μL, 0.91 mmol, 1.1 eq), was added and the reaction mixture was stirred for 20 minutes.

The reaction mixture was then treated sequentially with anhydrous N-methyl-2-pyrrolidinone (4.1 mL), the Pd$_2$(dba)$_3$.CHCl$_3$ catalyst (17.2 mg, 1.6×10$^{-2}$ mmol, 2.0 mol %), tris (2,4,6-trimethoxyphenyl) phosphine (35.2 mg, 1.6×10$^{-2}$ mmol, 8.0 mol %), the aryl-stannane 8 (214.0 mg, 0.55 mmol, 0.66 eq), and zinc chloride (0.55 mL, 0.55 mmol, 0.66 eq). The low temperature bath was then removed and the reaction vessel was placed in a warm water bath to quickly reach ambient temperature. The resulting wine-red solution was stirred for 40 minutes at ambient temperature.

The reaction was then poured into ether (250 mL) and washed with water (3×) and brine. The organic layer was dried (MgSO$_4$), decolorized briefly with Norite, filtered, and evaporated in vacuo. Purification using flash chromatography (100% EtOAc) provided 246 mg (71%) of the coupled product 10, a yellow foam.

$^1$H-NMR for 10 [400 MHz, CDCl$_3$]: δ0.15 (s, 9H), 1.30 (d, J=6.0 Hz, 3H), 2.73 (broad t, J=5.7 Hz, 1H), 3.26 to 3.34 (complex m, 2H), 3.42 (½ ABX, J$_{AB}$=18.3 Hz, J$_{AX}$=8.7 Hz, 1H), 4.24 to 4.30 (m, 1H), 4.35 (dt, J=9.5, 2.7 Hz, 1H), 4.75 (d, J=5.8 Hz, 2H), 5.21 (ABq, J=13.3 Hz, Δv$_{AB}$=73.8 Hz, 2H), 7.04 (d, J=8.4 Hz, 1H), 7.26 (s, 1H), 7.31 (d, J=8.4 Hz, 2H), 7.44 (d, J=8.1 Hz, 1H), 7.74 (d, J=8.4 Hz, 1H), 7.91 (d, J=8.4 Hz, 2H), 8.04 (s, 1H), 8.43 (d, J=8.1 Hz, 1H), 10.85 (s, 1H).

IR (CHCl$_3$): 3400, 3010, 2980, 1780, 1725, 1665, 1610, 1520 cm$^{-1}$. U.V. (CH$_3$CN): λ=315 nm, ε=18,000.

EXAMPLE 9

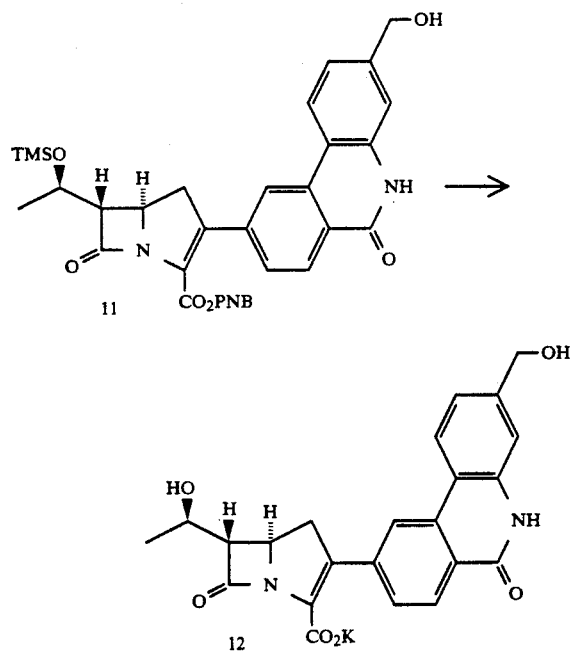

Acetic acid (6.3 μL, 0.11 mmol, 1.0 eq) was added to a stirred solution of 11 (68.8 mg, 0.11 mmol) in 1.3:1.3:1.0 THF/EtOH/H$_2$O, and the reaction mixture was stirred for 1.75 hours at 40° C. Potassium bicarbonate (23.1 mg, 0.23 mmol, 2.1 eq) was then added. The 10% Pd/C catalyst (6.9 mg, 10% wt) was added next, and the reaction mixture was hydrogenated under a H$_2$ balloon at ambient temperature for 1 hour. The mixture was then filtered through a pad of celite using water as the eluant, and the THF and EtOH solvent from the filtrate were removed in vacuo. The remaining water was then frozen and lyophilized at 0° C. Crude 12 was redissolved in a minimal amount of H$_2$O/CH$_3$CN and purified using Analtech reverse phase prep-plates (6:1 H$_2$O/CH$_3$CN) to provide 16.6 mg (36%) of carbapenem 12, a light-yellow solid.

$^1$H-NMR for 12 [400 MHz, 2:1 D$_2$O/CD$_3$CN]: δ1.69 (d, J=6.3 Hz, 3H), 3.56 (½ ABX, J$_{AB}$=16.6 Hz, J$_{AX}$=10.2 Hz, 1H), 3.87 to 3.95 (complex m, 2H), 4.59 to 4.64 (m, 1H), 4.73 (dt, J=9.3, 2.6 Hz, 1H), 5.07 (s, 2H), 7.65 (s,1H), 7.68 (d, J=8.7 Hz, 1H), 8.01 (d, J=8.1 Hz, 1H), 8.52 to 8.59 (m, 3H).

IR(KBr): 1755, 1660, 1615 cm$^{-1}$.

U.V. (MOPS Buffer): λ$_{o1}$=309 nm, ε$_{o1}$=16,000; λ$_{o2}$=326 nm, ε$_{o2}$=15,900; λ$_{ext1}$=309 nm, ε$_{ext1}$=10,600; λ$_{ext2}$=337 nm, ε$_{ext2}$=9,600; λ$_{ext3}$=349 nm, ε$_{ext3}$=8,300.

EXAMPLE 10

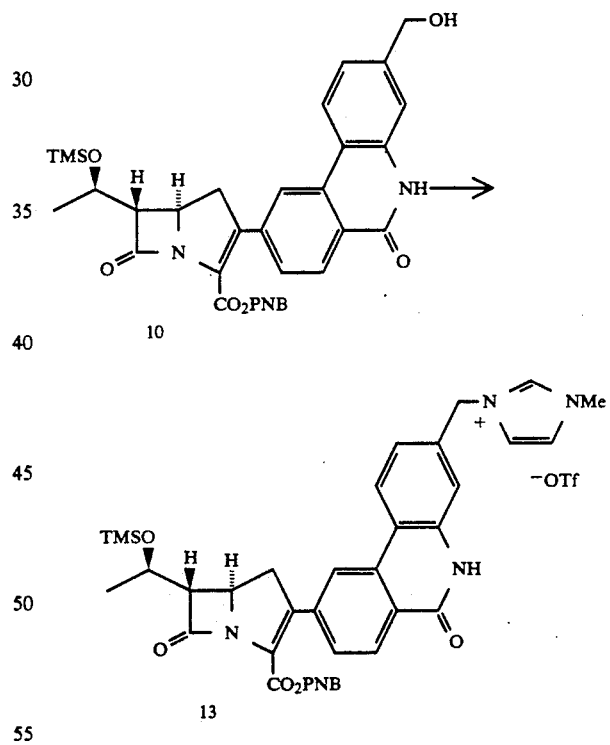

N-methylimidazole (44.3 μL, 0.55 mmol, 2.6 eq) was added to a stirred solution of 10 (133.5 mg, 0.21 mmol) in anhydrous dichloromethane (2.1 mL) at −78° C. Trifluoromethane sulfonic anhydride (43.2 μL, 0.26 mmol, 1.2 eq) was added next, and the reaction mixture was warmed to −50° C. and stirred for 20 minutes. The reaction was then poured into dichloromethane (50 mL) and washed with water (3×). The organic layer was dried (Na$_2$SO$_4$), filtered, and concentrated in vacuo. The residue was redissolved in a minimal amount of dichloromethane (1 mL). Excess diethyl ether was added to precipitate the quaternary salt, which was filtered, to provide 112 mg (62.5%) of 13, a yellow solid.

$^1$H-NMR for 13 [400 MHz, CDCl$_3$]: δ0.14 (s, 9H), 1.29 (d, J=6.2 Hz, 3H), 3.24 to 3.48 (complex m, 3H), 4.00 (s, 3H), 4.20 to 4.39 (complex m, 2H), 5.20 (ABq, J=13.4 Hz, Δυ$_{AB}$=74.1 Hz, 2H), 5.38 (s, 2H), 7.1 (d, J=8.4 Hz, 1H), 7.30 to 7.32 (m, 3H), 7.42 to 7.43 (m, 3H), 7.64 (d, J=8.4 Hz, 1H), 7.86 to 7.89 (m, 3H), 8.27 (d, J=8.2 Hz, 1H), 9.41 (s, 1H), 9.60 (s, 1H). IR (CHCl$_3$): 3150, 3025, 2960, 1775, 1725, 1670, 1615, 1520 cm$^{-1}$.

U.V. (CH$_3$CN): λ=316 nm, ε=15,370.

EXAMPLE 11

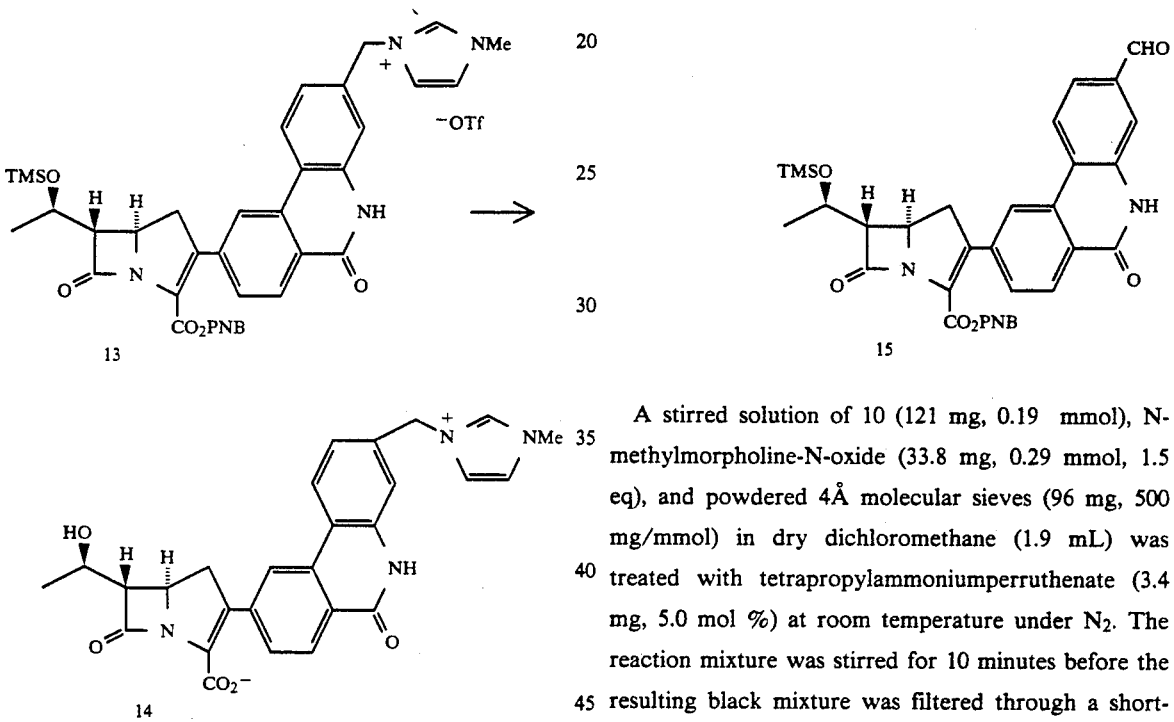

The quaternary salt 13 (53.0 mg, 0.063 mmol) was deprotected according to the general procedure described for the deprotection of compound 11 to the carbapenem 12. Crude 14 was purified using Analtech reverse phase prep-plates (2:1 H$_2$O/CH$_3$CN) to provide 15.7 mg (51%) of the quaternary carbapenem 14, a yellow solid.

$^1$H-NMR for 14 [400 MHz, 2:1 D$_2$O/CD$_3$CN]: δ1.68 (d, J=6.3 Hz, 3H), 3.57 (½ ABX, J$_{AB}$=16.3 Hz, J$_{AX}$=9.7 Hz, 1H), 3.87 to 3.93 (complex m, 2H), 4.24 (s, 3H), 4.59 to 4.63 (m, 1H), 4.75 (dt, J=9.7, 2.6 Hz, 1H), 5.79 (s, 2H), 7.66 to 7.68 (m, 2H), 7.83 (s, 1H), 7.88 (s, 1H), 8.03 (d, J=8.4 Hz, 1H), 8.60 (d, J=8.4 Hz, 1H), 8.65 (d, J=8.8 Hz, 1H), 8.73 (s, 1H), 9.18 (s, 1H).

IR (KBr): 1755, 1660, 1605 cm$^{-1}$

U.V. (MOPS Buffer): λ$_{01}$=311 nm, ε$_{01}$=13,230; λ$_{02}$=316 nm, ε$_{02}$=13,218; λ$_{ext1}$=309 nm, ε$_{ext1}$=8,345; λ$_{ext2}$=332 nm, ε$_{ext2}$=7,782; λ$_{ext3}$=348 nm, ε$_{ext3}$=7,400.

EXAMPLE 12

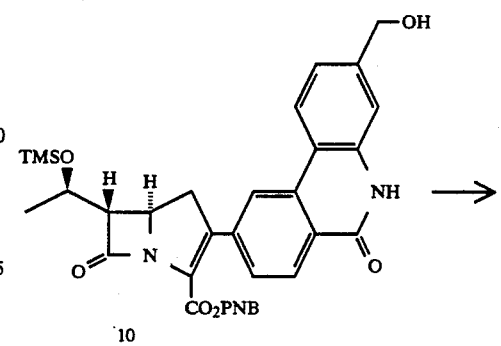

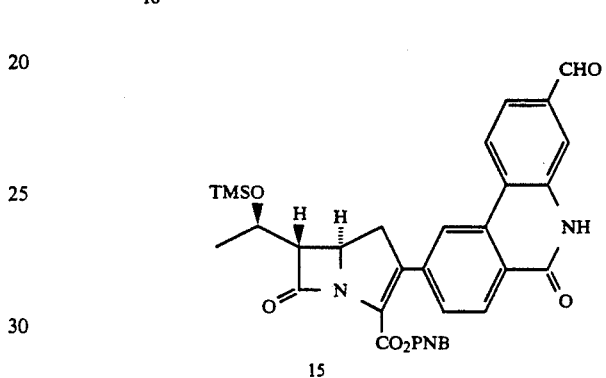

A stirred solution of 10 (121 mg, 0.19 mmol), N-methylmorpholine-N-oxide (33.8 mg, 0.29 mmol, 1.5 eq), and powdered 4Å molecular sieves (96 mg, 500 mg/mmol) in dry dichloromethane (1.9 mL) was treated with tetrapropylammoniumperruthenate (3.4 mg, 5.0 mol %) at room temperature under N$_2$. The reaction mixture was stirred for 10 minutes before the resulting black mixture was filtered through a short-column of silica gel using 75% EtOAc/hex as an eluant. The filtrate was evaporated in vacuo to afford 67 mg (56%) of aldehyde 15, a yellow oil.

$^1$H-NMR for 15 [400 MHz, CDCl$_3$]: δ0.15 (s, 9H), 1.31 (d, J=6.2 Hz, 3H), 3.31 to 3.38 (complex m, 2H), 3.45 (½ ABX, J$_{AB}$=18.5 Hz, J$_{AX}$=8.9 Hz, 1H), 4.27 to 4.31 (m, 1H), 4.39 (dt, J=9.5, 2.8 Hz, 1H), 5.25 (ABq, J=13.5 Hz, Δυ$_{AB}$=68.7 Hz, 2H), 7.39 (d, J=8.7 Hz, 2H), 7.57 (d, J=8.3 Hz, 1H), 7.69 (d, J=8.3 Hz, 1H), 7.79 (s, 1H), 8.00 (d, J=8.7 Hz, 2H), 8.11 (d, J=8.3 Hz, 1H), 8.26 (s, 1H), 8.52 (d, J=8.2 Hz, 1H), 10.05 (s, 1H), 11.53 (s, 1H).

IR (CHCl$_3$): 3020, 2960, 1780, 1730, 1705, 1670, 1610, 1520 cm$^{-1}$.

U.V. (CH$_3$CN): λ=301 nm, ε=28,230.

EXAMPLE 13

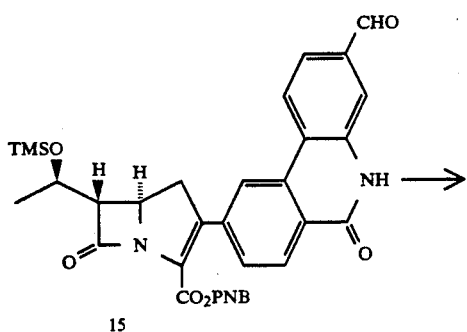

15

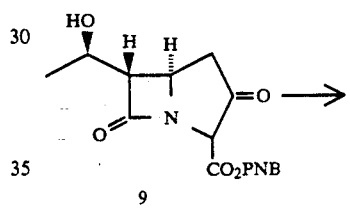

16

Anhydrous 1M HCl in ether (47.0 μL, 4.7×10$^{-2}$ mmol, 0.50 eq) was added to a stirred solution of 15 (58.7 mg, 9.4×10$^{-2}$ mmol) in 2:1 THF/H$_2$O at 0° C. and the reaction mixture was stirred for 10 minutes at 0° C. Aqueous sodium bicarbonate solution (0.15 mL, 0.15 mmol, 1.6 eq) was then added and the ice bath was removed. After adding 10% Pd/C (5.8 mg, 10% wt) the reaction mixture was hydrogenated under a H$_2$ balloon at ambient temperature for 1 hour. The mixture was then filtered through a pad of celite using water as the eluant. The THF from the filtrate was removed in vacuo and the remaining water was frozen and lyophilized at 0° C. Crude 15 was redissolved in a minimal amount of H$_2$O/CH$_3$CN and purified using Analtech reverse phase prep-plates eluted with 7:1 H$_2$O/CH$_3$CN. Carbapenem 16 was isolated as a yellowish solid in 37% yield (15.3 mg).

$^1$H-NMR for 16 [400 MHz, 2:1 D$_2$O/CD$_3$CN]: δ1.71 (d, J=6.3 Hz, 3H), 3.59 (½ ABX, J$_{AB}$=16.5 Hz, J$_{AX}$=9.9 Hz, 1H), 3.90 to 3.96 (complex m, 2H), 4.62 to 4.66 (m, 1H), 4.75 (dt, J=9.7, 2.7 Hz, 1H), 8.13 (d, J=8.4 Hz, 1H), 8.19 (s, 1H), 8.21 (d, J=8.3 Hz, 1H), 8.64 (d, J=8.4 Hz, 1H), 8.71 (s, 1H), 8.78 (d, J=8.3 Hz, 1H), 10.39 (s, 1H).

IR (KBr): 3420, 1755, 1690, 1660, 1615 cm$^{-1}$.

UV (MOPS Buffer): λ$_0$=305 nm, ε$_0$=19,600; λ$_{ext1}$=314 nm, ε$_{ext1}$=10,900; λ$_{ext2}$=367 nm, ε$_{ext2}$=4,970.

EXAMPLE 14

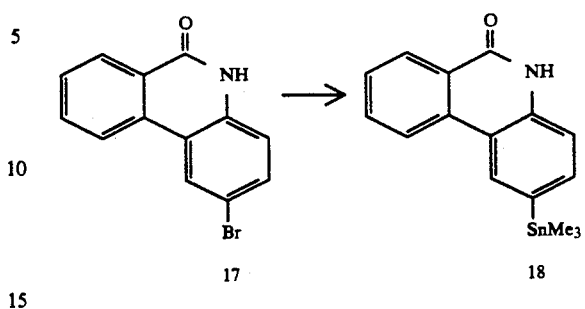

From 17 (0.5 g, 1.82 mmol), using the general stannylation procedure described for compound 8 was provided 498 mg (76%) of stannane 18, a white solid.

$^1$H-NMR for 18 [300 MHz, CDCl$_3$]: δ0.36 (s, 9H), 7.41 (d, J=7.8 Hz, 1H), 7.57 to 7.64 (m, 2H), 7.80 (t, J=7.4 Hz, 1H), 8.31 (s, 1H) 8.33 (d, J=8.2 Hz, 1H), 8.59 (d, J=7.1 Hz, 1H), 11.23 (s, 1H).

IR (CHCl$_3$): 3400, 3010, 1665, 1610 cm$^{-1}$.

EXAMPLE 15

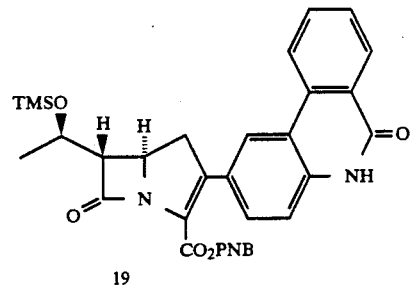

Following the general coupling procedure described for the synthesis of compound 10, the bicyclic β-keto ester 9 (160.5 mg, 0.46 mmol) was coupled to the aryl stannane 18 (150 mg, 0.42 mmol, 0.91 eq) to provide 169 mg (67%) of 19, a yellowish solid.

$^1$H-NMR for 19 [300 MHz, CDCl$_3$]: δ0.15 (s, 9H), 1.31 (d, J=6.3 Hz, 3H), 3.27 to 3.38 (complex m, 3H), 4.25 to 4.34 (complex m, 2H), 5.28 (ABq, J=13.7 Hz, Δυ$_{AB}$=53.3 Hz, 2H), 7.31 (d, J=8.4 Hz, 1H), 7.49 (m, 3H), 7.62 (t, J=7.1 Hz, 1H), 7.76 (t, J=7.1 Hz, 1H), 8.08 (d, J=8.7 Hz, 2H), 8.15 (d, J=8.2 Hz, 1H), 8.31 (s, 1H), 8.54 (d, J=7.6 Hz, 1H), 11.40 (s, 1H).

IR (CHCl$_3$): 3010, 2960, 1780, 1725, 1665, 1610, 1520 cm$^{-1}$.

UV (CH$_3$CN): λ=328 nm, ε=14,800.

EXAMPLE 16

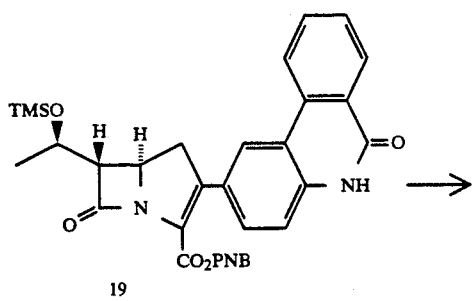

From 19 (169 mg, 0.28 mmol) in 1:1:1 THF/CH₃CN/H₂O, using the general deprotection procedure described for compound 12, was provided 83 mg (68%) of 20, a yellowish solid.

$^1$H-NMR for 20 [300 MHz, 2:1 D$_2$O/CD$_3$CN]: δ1.68(d, J=6.4 Hz, 3H), 3.54 (½ ABX, J$_{AB}$=16.9 Hz, J$_{AX}$=9.8 Hz, 1H), 3.82 to 3.87 (complex m, 2H), 4.58 to 4.69 (complex m, 2H), 7.71 (d, J=8.5 Hz, 1H), 7.98 (d, J=8.5 Hz, 1H), 8.07 (t, J=7.2 Hz, 1H), 8.29 (t, J=7.2 Hz, 1H), 8.68 (s, 1H), 8.73 (d, J=8.1 Hz, 1H), 8.78 (d, J=8.2 Hz, 1H).

IR (KBr): 1755, 1670, 1630, 1605, 1550 cm$^{-1}$.

U.V. (MOPS Buffer): λ$_0$=323 nm, ε$_0$=17,000; λ$_{ext1}$=316 nm, ε$_{ext1}$=9,400; λ$_{ext2}$=331 nm, ε$_{ext2}$=7,900; λ$_{ext3}$=350 nm, ε$_{ext3}$=8,600.

EXAMPLE 17

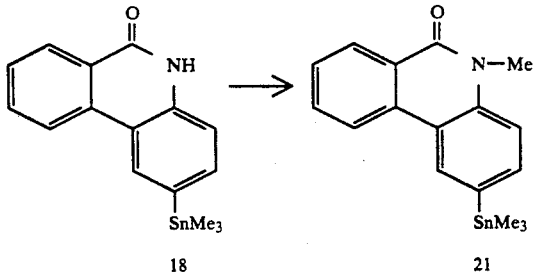

To a suspension of sodium hydride (16.7 mg, 0.42 mmol, 1.0 eq. 60% in mineral oil) in anhydrous DMF (4.2 mL) and dry benzene (0.42 mL) was added 18 (150 mg, 0.42 mmol) at 0° C. After the evolution of H$_2$ gas had subsided the resultant yellow mixture was stirred at 100° C. for 30 minutes. The reaction mixture was then cooled to 0° C. and iodomethane (39.2 μL, 0.63 mmol, 1.5 eq) in anhydrous DMF (2.1 mL) was added. After stirring for 3.5 h at 100° C. the resultant brown mixture was quenched with dropwise addition of saturated ammonium chloride solution (2 mL) at 0° C. The reaction mixture was then poured into ethyl acetate (75 mL) and washed with water (1×), saturated sodium bicarbonate solution (1×25 mL), water (2×), and brine. The organic layer was dried (MgSO$_4$), filtered, and evaporated in vacuo. Purification using flash chromatography (20% EtOAc/hex) provided 52.0 mg (33%) of stannane 21, a white solid.

$^1$H-NMR for 21 [300 MHz, CDCl$_3$]: δ0.37 (s, 9H), 3.79 (s, 3H), 7.37 (d, J=8.1 Hz), 7.56 (t, J=7.1 Hz, 1H), 7.63 (d, J=8.2 Hz, 1H), 7.75 (t, J=7.2 Hz, 1H), 8.32 (d, J=7.9 Hz, 1H), 8.36 (s, 1H), 8.54 (d, J=7.7 Hz, 1H).

IR (CHCl$_3$): 3010, 2920, 1645, 1600, 1575 cm$^{-1}$.

EXAMPLE 18

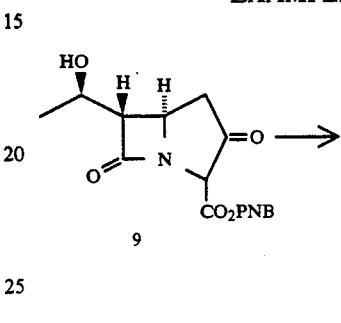

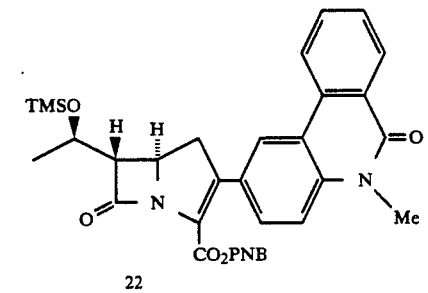

Following the general coupling procedure described for compound 10, the bicyclic β-keto ester 9 (58.4 mg, 0.167 mmol) was coupled to the aryl stannane 21 (52.0 mg, 0.14 mmol, 0.84 eq) to provide 56 mg (65%) of 22, a yellow oil.

$^1$H-NMR for 22 [300 MHz, CDCl$_3$]: δ0.15 (s, 9H), 1.31 (d, J=6.3 Hz, 3H), 3.27 to 3.30 (m, 1H), 3.34 to 3.39 (complex m, 2H), 3.79 (s, 3H), 4.23 to 4.35 (complex m, 2H), 5.30 (ABq, J=13.7 Hz, Δυ$_{AB}$=55.8 Hz, 2H), 7.36 (d, J=8.8 Hz, 1H), 7.52 to 7.60 (m, 4H), 7.72 (t, J=7.2 Hz, 1H), 8.10 (d, J=8.7 Hz, 2H), 8.14 (d, J=8.1 Hz, 1H), 8.38 (s, 1H), 8.52 (d, J=7.9 Hz, 1H).

IR (CHCl$_3$): 3020, 2970, 1775, 1725, 1650, 1610, 1520 cm$^{-1}$.

U.V.(CH$_3$CN): λ=333 nm, ε=11,700.

EXAMPLE 19

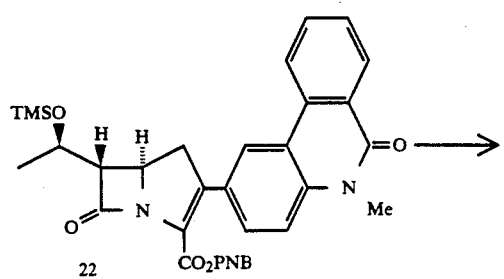

-continued

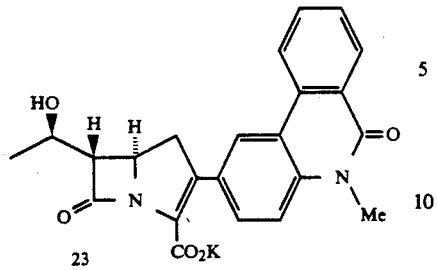

From 22 (56 mg, 0.092 mmol), using the general deprotection procedure described for compound 12, was provided 12.9 mg (32%) of carbapenem 23, a white solid.

$^1$H-NMR for 23 [300 MHz, D$_2$O]: δ1.47(d, J=6.6 Hz, 3H), 3.18 to 3.26 (m, 1H), 3.46 to 3.64 (complex m, 2H), 3.53 (s, 3H), 4.39 to 4.49 (complex m, 2H), 7.27 (d, J=8.9 Hz, 1H), 7.52 (d, J=7.8 Hz, 1H), 7.59 (t, J=7.9 Hz, 1H), 7.74 (t, J=7.4 Hz, 1H), 7.88 (s, 1H), 7.95 (d, J=8.2 Hz, 1H), 8.12 (d, J=8.1 Hz, 1H).

IR (KBr): 2980, 1740, 1640, 1605, 1575 cm$^{-1}$.

U.V. (MOPS Buffer): λ$_o$=320 nm, ε$_o$=12,000; λ$_{ext1}$=317 nm, ε$_{ext1}$=6,700; λ$_{ext2}$=352 nm, ε$_{ext2}$=5,100.

EXAMPLE 20

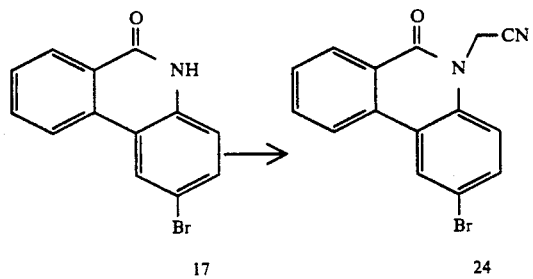

To a suspension of sodium hydride (73 mg, 1.82 mmol, 1.0 eq, 60% in mineral oil) in anhydrous DMF (18.2 mL) was added 17 (500 mg, 1.82 mmol) at 0° C. After the evolution of H$_2$ gas had subsided the resultant yellow mixture was stirred at 100° C. for 30 minutes. The reaction mixture was then cooled to 0° C. and bromoacetonitrile (0.14 mL, 2.0 mmol, 1.1 eq) in dry DMF (9.1 mL) was added. After stirring for 1 hour at 100° C. the resultant black mixture was quenched with dropwise addition of saturated ammonium chloride solution (5 mL) at 0° C. The reaction mixture was then poured into ethyl acetate (175 mL) and washed with water (1×), saturated sodium bicarbonate solution (1×50 mL), water (2×), and brine. The organic layer was dried (MgSO$_4$), filtered, and evaporated in vacuo. Recrystallization from ethyl acetate afforded 352 mg (62%) of the N-cyanomethyl compound 24, white crystalline needles.

$^1$H-NMR for 24 [300 MHz, D$_6$DMSO]: δ5.53 (s, 2H), 7.68 (d, J=9.2 Hz, 1H), 7.75 (t, J=7.7 Hz, 1H), 7.88 (d, J=8.9 Hz, 1H), 7.93 (t, J=8.1 Hz, 1H), 8.38 (d, J=7.8 Hz, 1H), 7.66 (d, J=8.5 Hz, 1H), 8.77 (s, 1H).

IR (KBr): 3000, 2960, 2250, 1660, 1605 cm$^{-1}$.

EXAMPLE 21

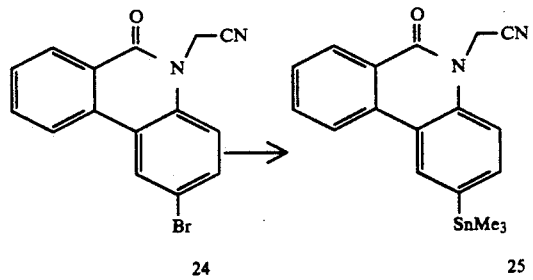

From 24 (382 mg, 0.48 mmol), using the general stannylation procedure described for compound 8, was provided 379 mg (78%) of stannane 25, a white solid.

$^1$H-NMR for 25 [300 MHz, CDCl$_3$]: δ0.38 (s, 9H), 5.33 (s, 2H), 7.35 (d, J=8.2 Hz, 1H), 7.57 (t, J=8.2 Hz, 1H), 7.70 (d, J=8.2 Hz, 1H), 7.80 (t, J=8.4 Hz, 1H), 8.31 (d, J=7.8 Hz, 1H), 8.38 (s, 1H), 8.49 (d, J=6.9 Hz, 1H).

IR (CHCl$_3$): 3010, 2990, 2980, 2920, 2260, 1660, 1615, 1601, 1580 cm$^{-1}$.

EXAMPLE 22

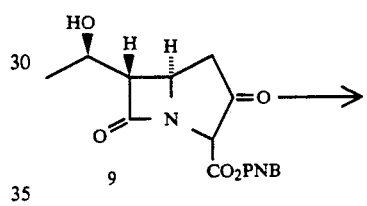

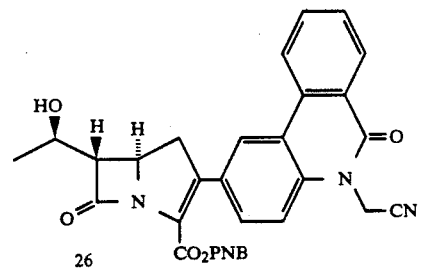

To a stirred solution of the bicyclic β-keto ester 9 (376.0 mg, 1.08 mmol) in dry THF (5.4 mL) at −78° C. under N$_2$ was added diisopropylamine (0.17 mL, 1.19 mmol, 1.1 eq). The resultant yellow mixture was stirred for 10 minutes before trifluoromethane sulfonic anhydride (0.20 mL, 1.19 mmol, 1.1 eq) was added. After 15 minutes the reaction mixture was treated sequentially with anhydrous N-methyl-2-pyrrolidinone (5.4 mL), the Pd$_2$(dba)$_3$•CHCl$_3$ catalyst (22.4 mg, 2.2×10$^{-2}$ mmol, 2.0 mol %), tris (2,4,6-trimethoxyphenyl)phosphine (46.0 mg, 8.6×10$^{-2}$ mmol, 8.0 mol %) the aryl stannane 25 (357.2 mg, 0.90 mmol, 0.83 eq), and zinc chloride (0.6 mL, 0.90 mmol, 0.83 eq). The low temperature bath was then removed and the reaction vessel was placed in a warm water bath to quickly reach ambient temperature. The resulting wine-red solution was stirred for 40 minutes at ambient temperature.

The reaction was then poured into ether (250 mL) and washed with water (3×) and brine. The organic layer was dried (MgSO$_4$), decolorized briefly with Norite, filtered, and evaporated in vacuo. Purification using flash chromatography (80%) EtOAc/hex) provided 201.9 mg (71%) of the coupled product 26, a yellow solid.

1H-NMR for 26 [300 MHz, CDCl3]: δ1.40 (d, J=6.3 Hz, 3H), 3.29 to 3.46 (complex m, 3H), 4.28 to 4.42 (complex m, 2H), 5.29 (ABq, J=13.4 Hz, Δv$_{AB}$=59.3 Hz, 2H), 5.33 (s, 2H), 7.34 (d, J=8.7 Hz, 1H), 7.49 (d, J=8.5 Hz, 2H), 7.57 to 7.63 (m, 2H), 7.76 (t, J=7.6 Hz, 1H), 8.07 (d, J=8.6 Hz, 2H), 8.12 (d, J=8.2 Hz, 1H), 8.39 (s, 1H), 8.45 (d, J=8.0 Hz, 1H).

IR (CHCl3): 3600, 3200, 2980, 1780, 1730, 1665, 1605, 1520 cm$^{-1}$.

U.V. (CH3CN): λ=325 nm, ε=10,000.

EXAMPLE 23

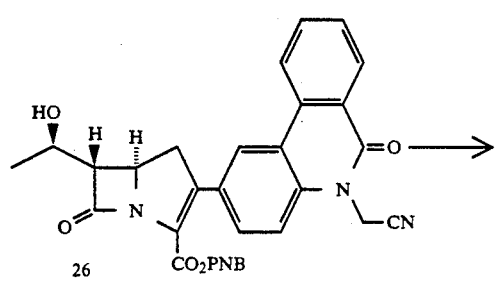

26

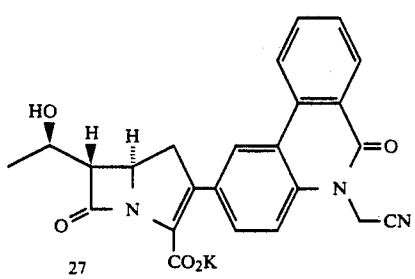

27

To a stirred solution of 26 (201 mg, 0.356 mmol) and potassium bicarbonate (39.2 mg, 0.392 mmol, 1.1 eq) in 2:1 acetone/H2O was added 10% Pd/C catalyst (20.1 mg, 10% wt), and the reaction mixture was hydrogenated under an H2 balloon at ambient temperature for 1.6 hours. The mixture was then filtered through a pad of celite using water as the eluant, and the acetone solvent from the filtrate was removed in vacuo. The remaining water was then frozen and lyophilized at 0° C. Crude 27 was redissolved in a minimal amount of H2O/CH3CN and purified using Analtech reverse phase prep-plates (3:1 H2O/CH3CN) to provide 43.6 mg (26%) of 27, a white solid.

1H-NMR for 27 [300 MHz, 2:1 D2O/CD3CN]: δ1.51 (d, J=6.3 Hz, 3H), 3.36 (½ ABX, J$_{AB}$=15.6 Hz, J$_{AX}$=8.9 Hz, 1H), 3.63 to 3.71 (complex m, 2H), 4.43 to 4.57 (complex m, 2H), 5.54 (s, 2H), 7.66 (d, J=9.3 Hz, 1H), 7.67 to 7.83 (m, 2H), 8.01 (t, J=8.8 Hz, 1H), 8.17 to 8.44 (m, 3H).

IR (KBr): 2980, 1755, 1650, 1601, 1570 cm$^{-1}$.

UV (MOPS Buffer): λ$_o$=316 nm, ε$_o$=13,600; λ$_{ext1}$=312 nm, ε$_{ext1}$=8,100; λ$_{ext2}$=349 nm, ε$_{ext2}$=5,800.

EXAMPLE 24

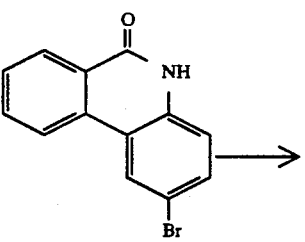

17

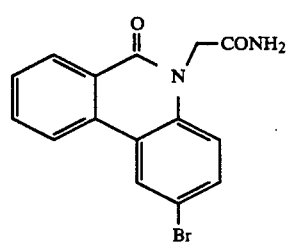

28

From 17 (350 mg, 1.28 mmol) and iodoacetamide (362 mg, 1.92 mmol, 1.5 eq) as the alkylating agent, using the general procedure described for compound 24 was provided 357 mg (84%) of the N-acetamide 28, a white solid.

1H-NMR for 28 [300 MHz, D6DMSO]: δ4.97 (s, 2H), 7.26 (d, J=9.2 Hz, 1H), 7.31 (s, 1H), 7.68 to 7.75 (m, 3H), 7.88 (t, J=7.2 Hz, 1H), 8.36 (d, J=7.8 Hz, 1H), 8.62 (d, J=8.1 Hz, 1H), 8.69 (s, 1H).

IR (KBr): 3200, 1685, 1650, 1610 cm$^{-1}$.

EXAMPLE 25

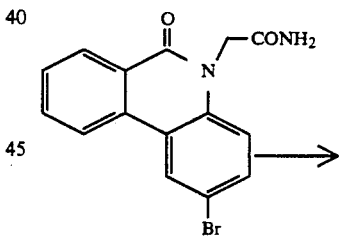

28

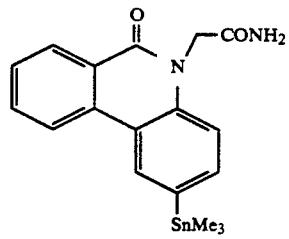

29

From 28 (280.7 mg, 0.85 mmol) in anhydrous DMF (8.5 mL), using the general stannylation procedure described for compound 8, was provided 69 mg (19%) of stannane 29, a yellowish solid.

1H-NMR for 29 [300 MHz, CDCl3]: δ0.36 (s, 9H), 5.02 (s, 2H), 5.39 (broad s, 1H), 6.31 (broad s, 1H), 7.52

(d, J=8.2 Hz, 1H), 7.60 (t, J=7.6 Hz, 1H), 7.65 (d, J=8.2 Hz, 1H), 7.80 (t, J=8.0 Hz, 1H), 8.35 (d, J=8.2 Hz, 1H), 8.39 (s, 1H), 8.52 (d, J=8.2 Hz, 1H).

IR (CHCl₃): 3490, 3410, 3010, 2915, 1690, 1640, 1605, 1570 cm⁻¹.

EXAMPLE 26

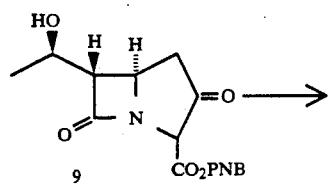

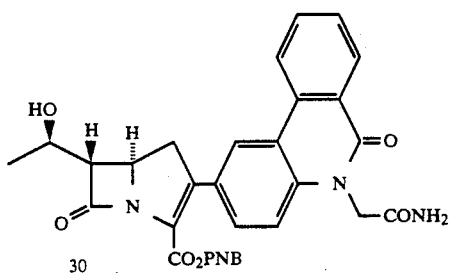

Following the general coupling procedure described for compound 10, the bicyclic β-keto ester 9 (54.0 mg, 0.15 mmol) was coupled to the aryl stannane 29 (45.5 mg, 0.13 mmol, 0.83 eq) to provide 11.7 mg (14%) of the coupled product 30, a yellowish solid.

¹H-NMR for 30 [300 MHz, CDCl₃]: δ0.15 (s, 9H), 1.31 (d, J=6.0 Hz, 3H), 3.25 to 3.36 (complex m, 3H), 4.22 to 4.34 (complex m, 2H), 4.99 (s, 2H), 5.28 (ABq, J=13.7 Hz, $\Delta\nu_{AB}$=53.3 Hz, 2H), 5.48 (broad s, 1H), 6.42 (broad s, 1H), 7.46 (d, J=8.7 Hz, 2H), 7.53 (s, 2H), 7.60 (t, J=7.5 Hz, 1H), 7.76 (t, J=7.4 Hz, 1H), 8.05 (d, J=8.2 Hz, 2H), 8.14 (d, J=8.5 Hz, 1H), 8.39 (s, 1H), 8.49 (d, J=7.8 Hz, 1H).

IR (CHCl₃): 3490, 3410, 3200, 2860, 1775, 1720, 1695, 1650, 1610, 1575, 1520 cm⁻¹.

U.V. (CH₃CN): $\lambda_1$=258 nm, $\epsilon_1$=25,400; $\lambda_2$=324, $\epsilon_2$=14,200.

EXAMPLE 27

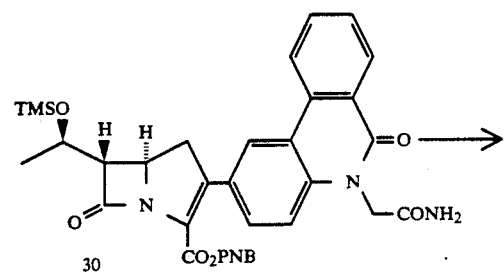

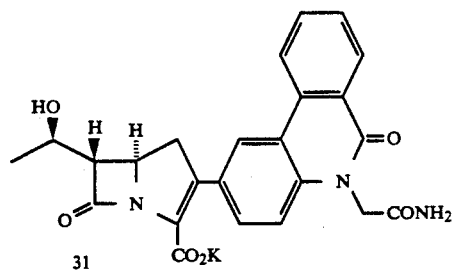

From 30 (11.1 mg, 0.017 mmol), using the general deprotection procedure described for compound 12, was provided 4.0 mg (49%) of carbapenem 31, a white solid.

¹H-NMR for 31 [300 MHz, 4:1 D₂O/CD₃CN]: δ1.50 (d, J=6.3 Hz, 3H), 3.34 (½ ABX, $J_{AB}$=16.2 Hz, $J_{AX}$=8.4 Hz, 1H), 3.68 to 3.71 (complex m, 2H), 4.42 to 4.56 (complex m, 2H), 5.20 (s, 2H), 7.42 (d, J=8.5 Hz, 1H), 7.73 (d, J=8.4 Hz, 1H), 7.81 (t, J=8.4 Hz, 1H), 8.02 (t, J=8.4 Hz, 1H), 8.42 to 8.45 (m, 3H).

IR (KBr): 2980, 1750, 1680, 1640, 1610, 1575 cm⁻¹.

U.V. (MOPS Buffer): $\lambda_o$=318 nm, $\epsilon_o$=12,000; $\lambda_{ext1}$=280 nm, $\epsilon_{ext1}$=6,900; $\lambda_{ext2}$=315 nm, $\epsilon_{ext2}$=7,500; $\lambda_{ext3}$=350 nm, $\epsilon_{ext3}$=5,700.

EXAMPLE 28

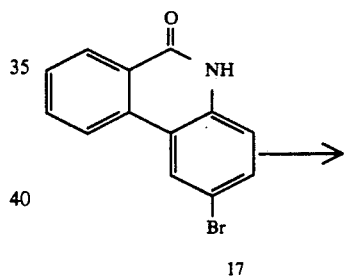

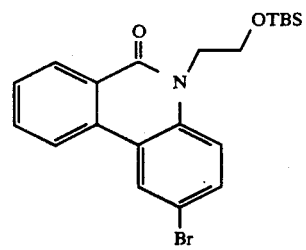

From 17 (2.0 g, 7.3 mmol) and 2-bromo(t-butyldimethylsilyl) ethanol (1.57 mL, 8.7 mmol, 1.2 eq) using the general alkylating procedure described for compound 24, was provided 2.1 g (69%) of bromide 32, a white crystalline solid.

¹H-NMR for 32 [300 MHz, CDCl₃]: δ0.10 (s, 9H), 0.80 (s, 6H), 4.00 (t, J=6.0 Hz, 2H), 4.47 (t, J=6.0 Hz, 2H), 7.55 to 7.61 (m, 3H), 7.75 (t, J=8.4 Hz, 1H), 8.17 (d, J=7.7 Hz, 1H), 8.32 (s, 1H), 8.51 (d, J=7.9 Hz, 1H).

IR (CHCl₃): 3010, 2980, 2930, 2860, 1645, 1605, 1580 cm⁻¹.

EXAMPLE 29

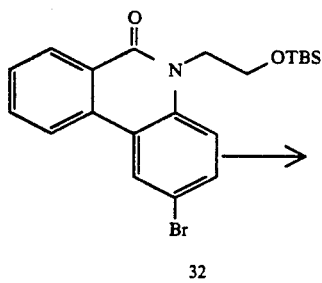

32

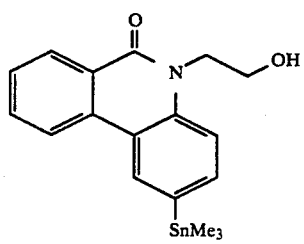

33

The bromide 32 (2.14 g, 5.1 mmol) was stannylated following the general stannylation procedure described for compound 8. The crude TBS-protected stannane was then redissolved in dry THF (51 mL), and tetrabutylammonium fluoride (7.6 mL, 7.6 mmol, 1.5 eq) was added at 0° C. The reaction mixture was then stirred for 1 h at room temperature, poured into ethyl acetate, and washed with water (1×), saturated ammonium chloride solution (1×), water (2×), and brine. The organic layer was dried (MgSO$_4$), filtered, and evaporated in vacuo. Purification using flash chromatography (40% EtOAc/hex) provided 1.34 g (65%) of stannane 33, a white solid.

$^1$H-NMR for 33 [300 MHz, CDCl$_3$]: δ0.36 (s, 9H), 2.86 (t, J=5.2 Hz, 1H), 4.07 to 4.12 (m, 2H), 4.62 (t, J=5.5 Hz, 2H), 7.43 (d, J=8.2 Hz, 1H), 7.56 to 7.64 (m, 2H), 7.78 (t, J=7.4 Hz, 1H), 8.34 (d, J=8.2 Hz, 1H), 8.40 (s, 1H), 8.51 (d, J=8.2 Hz, 1H).

IR (CHCl$_3$): 3540 to 3320, 3020, 1630, 1607, 1570 cm$^{-1}$.

EXAMPLE 30

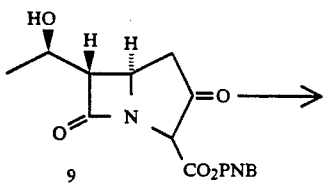

9

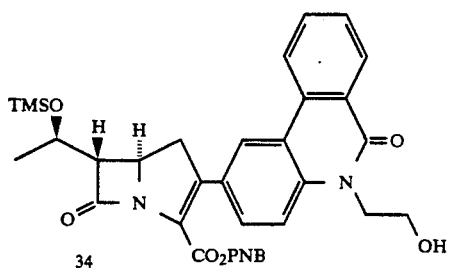

34

Following the general coupling procedure described for compound 10, the bicyclic β-keto ester 9 (506 mg, 1.45 mmol) was coupled to the aryl stannane 33 (509 mg, 1.21 mmol, 0.83 eq) to provide 621 mg (80%) of 34, a yellow foam.

$^1$H-NMR for 34 [300 MHz, CDCl$_3$]: δ0.15 (s, 9H), 1.30 (d, J=6.0 Hz, 3H), 2.86 (broad t, J=4,8 Hz, 1H), 3.27 to 3.37 (complex m, 3H), 4.06 (d, J=4.9 Hz, 2H), 4.23 to 4.34 (complex m, 2H), 4.58 (t, J=5.2 Hz, 2H), 5.29 (ABq, J=13.7 Hz, Δυ$_{AB}$=53.7 Hz, 2H), 7.42 to 7.59 (m, 5H), 7.70 (t, J=7.6 Hz, 1H), 8.08 (d, J=8.4 Hz, 2H), 8.12 (d, J=8.1 Hz, 1H), 8.39 (s, 1H), 8.46 (d, J=7.8 Hz, 1H).

IR (CHCl$_3$): 3600 to 3240, 3010, 2960, 1775, 1720, 1640, 1610, 1520 cm$^{-1}$.

U.V. (CH$_3$CN): λ=330 nm, ε=11,300.

EXAMPLE 31

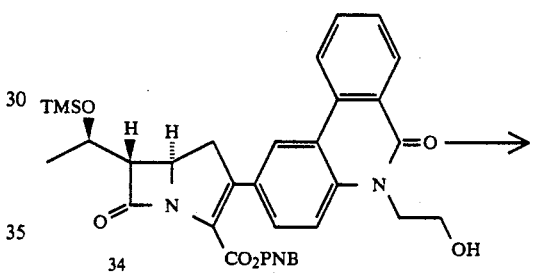

34

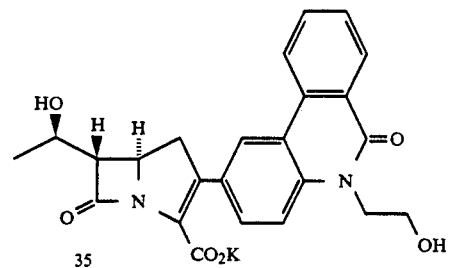

35

From 34 (18.9 mg, 2.9×10$^{-2}$ mmol), using the general deprotection procedure described for compound 12, was provided 5.4 mg (39%) of carbapenem 35, a yellow solid.

$^1$H-NMR for 35 [300 MHz, D$_2$O]: δ1.47 (d, J=6.3 Hz, 3H), 3.34 (½ ABX, J$_{AB}$=16.3 Hz, J$_{AX}$=9.3 Hz, 1H), 3.64 to 3.97 (complex m, 2H), 4.41 (broad t, J=5.7 Hz, 2H), 4.39 to 4.56 (complex m, 4H), 7.48 (d, J=8.8 Hz, 1H), 7.58 (d, J=8.2 Hz, 1H), 7.67 (t, J=7.4 Hz, 1H), 7.86 (t, J=7.3 Hz, 1H), 8.11 to 8.16 (m, 2H), 8.26 (d, J=8.2 Hz, 1H).

IR (KBr): 2980, 2920, 1750, 1640, 1610, 1580 cm$^{-1}$.

UV (MOPS Buffer): λ$_o$=324 nm, ε$_o$=8,680; λ$_{ext1}$=318 nm, ε$_{ext1}$=5,110; λ$_{ext2}$=351 nm, ε$_{ext2}$=4,090.

EXAMPLE 32

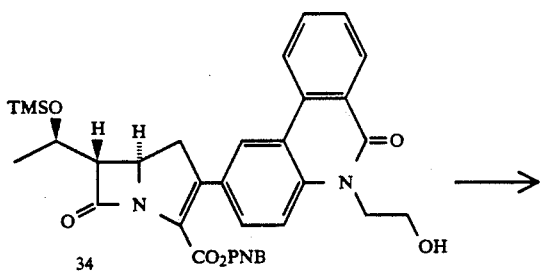

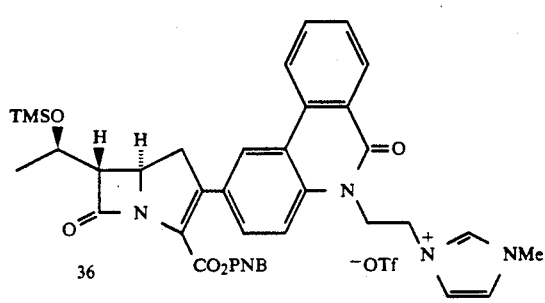

From 34 (150 mg, 0.23 mmol), using the general procedure described for the preparation of quaternary salt 13, was isolated 148 mg (74%) of the N-methylimidazole compound 36, a yellow solid.

$^1$H-NMR for 36 [300 MHz, $D_6$ Acetone]: δ0.17 (s, 9H) 1.29 (d, J=6.2 Hz, 3H), 3.39 to 3.52 (complex m, 2H), 3.69 (½ ABX, $J_{AB}$=15.7 Hz, $J_{AX}$=8.8 Hz, 1H), 4.00 (s, 3H), 4.31 to 4.41 (complex m, 2H), 4.87 (broad s, 2H), 4.96 (broad s, 2H), 5.38 (ABq, J=13.8 Hz, $\Delta\nu_{AB}$=47.3 Hz, 2H), 7.55 to 7.72 (m, 5H), 7.81 (m, 2H), 8.02 to 8.10 (m, 3H), 8.33 (d, J=8.7 Hz, 1H), 8.42 (t, J=7.9 Hz, 1H), 8.61 (d, J=8.6 Hz, 1H), 9.17 (s, 1H).

IR (CHCl$_3$): 3030, 2960, 1775, 1720, 1650, 1601, 1525 cm$^{-1}$.

U.V. (CH$_3$CN): λ=338 nm, ε=11,490.

EXAMPLE 33

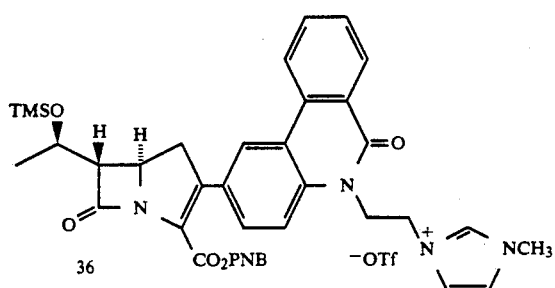

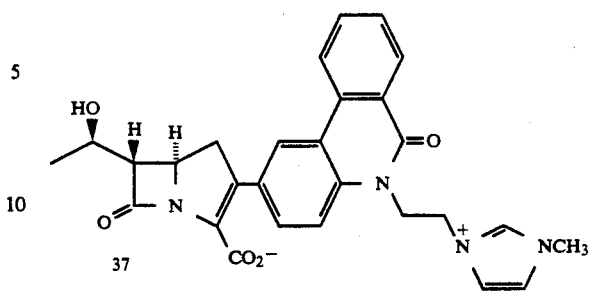

Acetic acid (21.7 μL, 0.38 mmol, 3.0 eq) was added to a stirred solution of 36 (108 mg, 0.126 mmol) in 2:1 THF/H$_2$O, and the reaction mixture was stirred for 5 hours at room temperature. Aqueous sodium bicarbonate solution was then added (0.52 mL, 0.52 mmol, 4.1 eq), followed by the 10% Pd/C catalyst (32.4 mg, 30% wt), and the reaction mixture was hydrogenated under a H$_2$ balloon at ambient temperature for 1.3 hour. Workup following the procedure described for carbapenem 12 afforded 15.5 mg (25%) of carbapenem 37, a yellow solid.

$^1$H-NMR for 37 [300 MHz, 2:1 D$_2$O/CD$_3$CN]: δ1.71 (d, J=6.3 Hz, 3H), 3.59 (½ ABX, $J_{AB}$=16.5 Hz, $J_{AX}$=9.6 Hz, 1H), 3.85 to 3.90 (complex m, 2H), 4.12 (s, 3H), 4.62 to 4.75 (complex m, 2H), 5.05 (broad t, J=5.2 Hz, 2H), 5.25 (broad t, J=5.3 Hz, 2H), 7.67 (s, 1H), 7.75 (s, 1H), 7.81 (d, J=8.7 Hz, 1H), 8.04 to 8.11 (m, 2H), 8.32 (t, J=7.1 Hz, 1H), 8.67 (d, J=8.1 Hz, 1H), 8.81 to 8.84 (m, 2H), 8.97 (s, 1H).

IR (KBr): 2960, 2920, 1750, 1640, 1605, 1575 cm$^{-1}$.

U.V. (MOPS Buffer): λ$_o$=319 nm, ε$_o$=12,000; λ$_{ext1}$=315 nm, ε$_{ext1}$=8,000; λ$_{ext2}$=349 nm, ε$_{ext2}$=6,000.

EXAMPLE 34

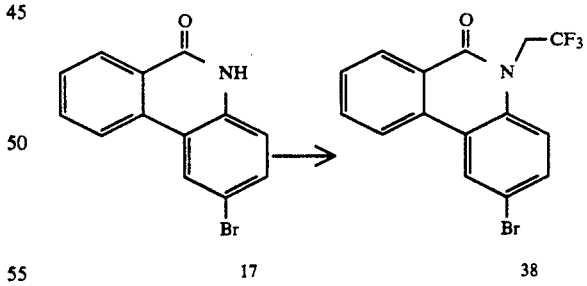

From 17 (500 mg, 1.82 mmol) and 2-bromo-1,1,1-trifluoroethane (1.9 mL, 20.9 mmol, 11.5 eq) using the general alkylating procedure described for compound 24, was provided 189 mg (29%) of bromide 38, a white solid.

$^1$H-NMR for 38 [300 MHz, CDCl$_3$]: δ5.05 (broad d, J=7.4 Hz, 2H), 7.26 (d, J=8.3 Hz, 1H), 7.59 to 7.64 (m, 2H), 7.73 (t, J=7.7 Hz, 1H), 8.16 (d, J=8.2 Hz, 1H), 8.34 (s, 1H), 8.50 (d, J=7.2 Hz, 1H).

IR (CHCl$_3$): 3200, 1670, 1610, 1580, 1560 cm$^{-1}$.

EXAMPLE 35

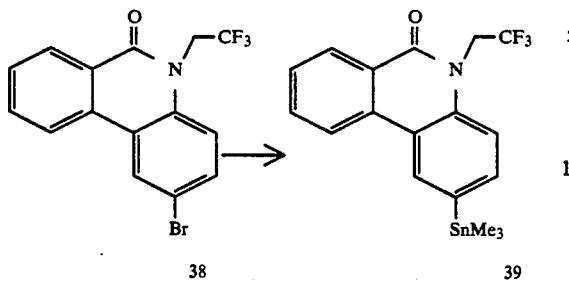

38    39

From 38 (189 mg, 0.53 mmol), using the general stannylaton procedure described for compound 8, was provided 171 mg (73%) of stannane 39, a white crystalline solid.

$^1$H-NMR for 39 [300 MHz, CDCl$_3$]: δ 0.28 (s, 9H), 5.09 (broad d, J=7.8 Hz, 2H), 7.38 (d, J=8.2 Hz, 1H), 7.57 (d, J=7.1 Hz, 1H), 7.62 (t, J=7.7 Hz, 1H), 7.79 (t, J=7.0 Hz, 1H), 8.32 (d, J=8.2 Hz, 1H), 8.38 (s, 1H), 8.53 (d, J=6.8 Hz, 1H).

IR (CHCl$_3$): 3010, 2980, 2910, 1660, 1605, 1590, 1575 cm$^{-1}$.

EXAMPLE 36

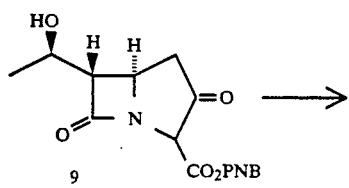

9

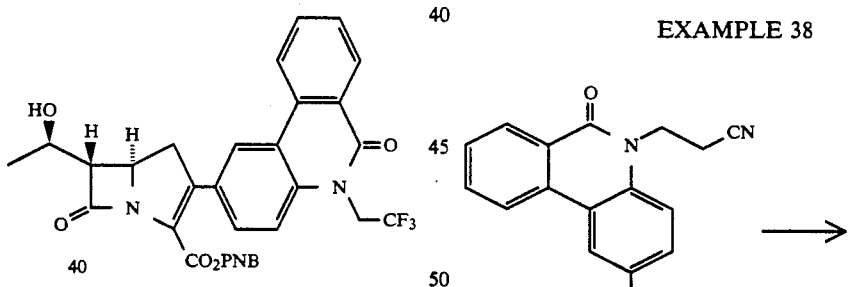

40

Following the coupling procedure described for compound 26, the bicyclic β-keto ester 9 (80 mg, 0.23 mmol) was coupled to the aryl stannane 39 (91.9 mg, 0.21 mmol, 0.91 eq) to provide 86.7 mg (68%) of carbapenem 40, a yellow solid.

$^1$H-NMR for 40 [300 MHz, CDCl$_3$]: δ 1.39 (d, J=6.3 Hz, 3H), 3.32 to 3.43 (complex m, 3H), 4.28 to 4.41 (complex m, 2H), 5.07 (broad d, J=7.7 Hz, 2H), 5.29 (ABq, J=13.5 Hz, Δv$_{AB}$=59.5 Hz, 2H), 7.35 (d, J=8.8 Hz, 1H), 7.47 to 7.52 (m, 3H), 7.58 (t, J=7.8 Hz, 1H), 7.73 (t, J=7.7 Hz, 1H), 8.06 (d, J=8.8 Hz, 2H), 8.11 (d, J=8.2 Hz, 1H), 8.38 (s, 1H), 8.49 (d, J=6.7 Hz, 1H).

IR (CHCl$_3$): 3010, 2970, 1775, 1720, 1670, 1610, 1520 cm$^{-1}$.

U.V. (CH$_3$CN): λ=324 nm, ε=14,600.

EXAMPLE 37

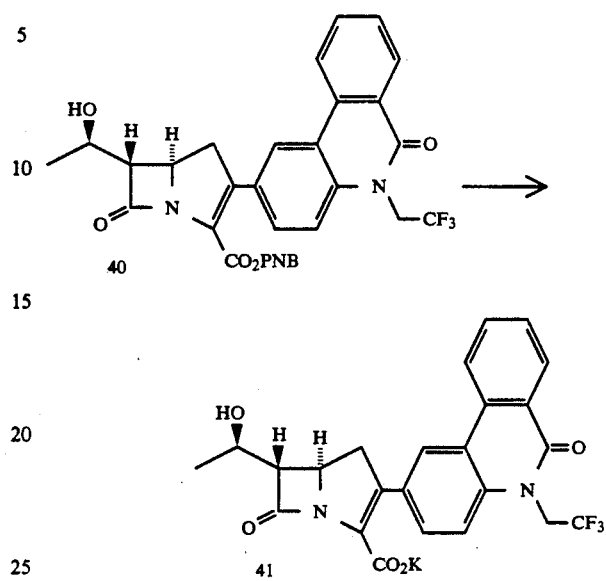

40

41

From 40 (54.7 mg, 0.09 mmol), using the deprotection procedure described for compound 27, was provided 30.4 mg (66%) of carbapenem 41, a white solid.

$^1$H-NMR for 41 [300 MHz, 2:1 D$_2$O/CD$_3$CN]: δ 1.73 (d, J=6.0 Hz, 3H), 3.62 (½ ABX, J$_{AB}$=16.2 Hz, J$_{AX}$=10.0 Hz, 1H), 3.87 to 3.93 (complex m, 2H), 4.64 to 4.75 (complex m, 2H), 5.69 (broad d, J=8.7 Hz, 2H), 8.05 to 8.19 (m, 3H), 8.39 (t, J=7.7 Hz, 1H), 8.85 to 8.95 (m, 3H).

IR (KBr): 2980, 1750, 1660, 1650, 1605, 1580 cm$^{-1}$.

U.V. (MOPS Buffer): λ$_o$=322 nm, ε$_o$=12,000, λ$_{ext1}$=315 nm, ε$_{ext1}$=6,300, λ$_{ext2}$=348 nm, ε$_{ext2}$=4,500.

EXAMPLE 38

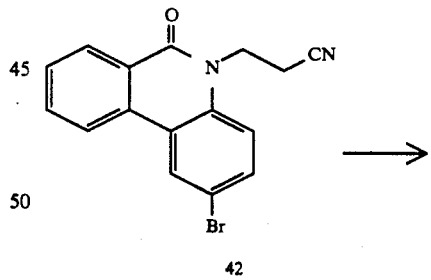

42

43

From 42 (54.7 mg, 0.17 mmol), using the general stannylation procedure described for compound 8, was provided 34.5 mg (50%) of stannane 43, a white foam.

¹H-NMR for 43 [300 MHz, CDCl₃]: δ0.37 (s, 9H), 2.88 (t, J=7.4 Hz, 2H), 4.68 (t, J=7.4 Hz, 2H), 7.38 (d, J=8.2 Hz, 1H), 7.58 (t, J=7.7 Hz, 1H), 7.67 (d, J=8.2 Hz, 1H), 7.78 (t, J=7.7 Hz, 1H), 8.33 (d, J=8.2 Hz, 1H), 8.40 (s, 1H), 8.50 (d, J=8.1 Hz, 1H).

IR (CHCl₃): 3010, 2920, 2260, 1640, 1610, 1580 cm⁻¹.

EXAMPLE 39

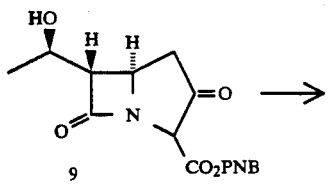

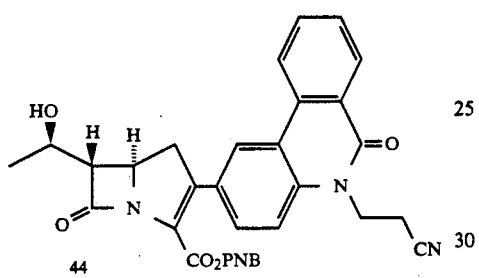

Following the coupling procedure described for compound 26, the bicyclic β-keto ester 9 (50.1 mg, 0.14 mmol) was coupled to the aryl stannane 43 (53.8 mg, 0.13 mmol, 0.91 eq) to provide 25.3 mg (33%) of 44, a white solid.

¹H-NMR for 44 [300 MHz, D₆ DMSO, Poorly resolved]: δ1.19 (d, J=6.3 Hz, 3H), 2.98 to 3.07 (broad s, 2H), 3.45 to 3.49 (complex m, 2H), 3.62 to 3.74 (m, 1H), 3.98 to 4.07 (m, 1H), 4.25 to 4.36 (m, 1H), 4.60 to 4.70 (broad s, 2H), 5.15 to 5.38, (m, 2H), 7.43 to 7.46 (m, 2H), 7.62 to 7.73 (m, 3H), 7.80 to 7.83 (broad s, 1H), 7.96 to 8.02 (m, 2H), 8.31 to 8.35 (m, 1H), 8.42 to 8.46 (m, 1H), 8.53 (s, 1H).

IR (KBr): 3110, 3060, 2960, 2250, 1780, 1715, 1630, 1605, 1575, 1515 cm⁻¹.

EXAMPLE 40

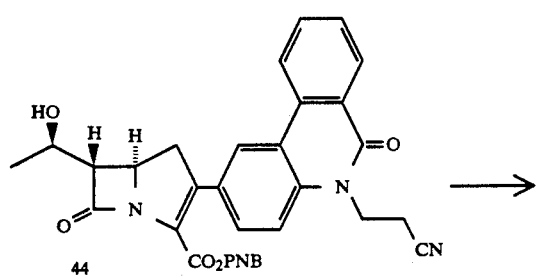

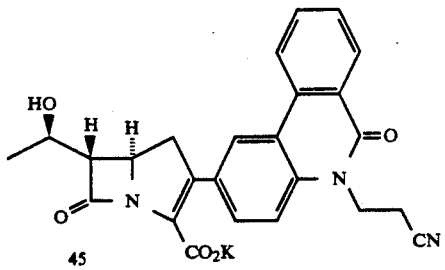

From 44 (17.8 mg, 3.1×10⁻² mmol), using the deprotection procedure described for compound 27, was provided 8.5 mg (57%) of carbapenem 45, a white solid.

¹H-NMR for 45 [300 MHz, 2:1 D₂O/CD₃CN]: δ1.74 (d, J=6.4 Hz, 3H), 3.47 (t, J=6.3 Hz, 2H), 3.63 (½ ABX, J$_{AB}$=16.7 Hz, J$_{AX}$=9.8 Hz, 1H), 3.87 to 4.00 (complex m, 2H), 4.64 to 4.78 (complex m, 2H), 5.16 (t, J=6.8 Hz, 2H), 8.04 (d, J=8.9 Hz, 1H), 8.12 to 8.17 (m, 2H), 8.37 (t, J=7.7 Hz, 1H), 8.84 to 8.92 (m, 3H).

IR (KBr): 2970, 2920, 2250, 1750, 1640, 1610, 1585 cm⁻¹.

U.V. (MOPS Buffer): λ$_o$=319 nm, ε$_o$=15,400; λ$_{ext1}$=316 nm, ε$_{ext1}$=9,200; λ$_{ext2}$=350 nm, ε$_{ext2}$=6,600.

EXAMPLE 41

Method A

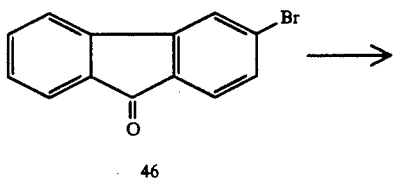

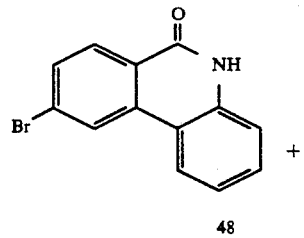

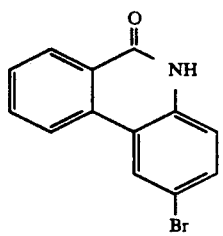

To a stirred solution of 46 (200 mg, 0.77 mmol) in concentrated sulfuric acid (12.9 mL) at 0° C. was added a solution of sodium azide (75.3 mg, 1.16 mmol, 1.5 eq) in water (1 mL). After stirring the resultant black mixture for 24 hours at room temperature, ice-water (10 mL) was added. The reaction mixture was then stirred for 15 minutes, poured into ethyl acetate (200 mL), and washed with saturated sodium bicarbonate solution (2×25 mL), water (2×), and brine. The organic layer was dried (MgSO4), filtered, and evaporated in vacuo to obtain a mixture of 1:1 inseparable bromo-phenanthridone isomers (48 and 17) in 74% yield (156 mg).

EXAMPLE 42

Method B

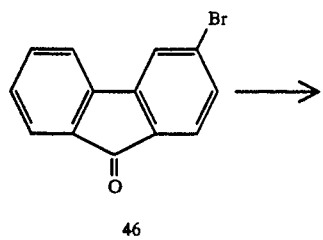

46

47

48

+

17

A suspension of 46 (200 mg, 0.77 mmol) and hydroxylamine hydrochloride (161 mg, 2.32 mmol, 3.0 eq) in anhydrous pyridine (7.7 mL) was sonicated to afford dissolution. The homogeneous mixture was then stirred at room temperature for 3.5 hour and poured into ether (100 mL). The ethereal layer was washed with water (1×), 1N HCl solution (4×15 mL), saturated sodium bicarbonate solution (2×15 mL), water (2×), and brine. The organic layer was dried (MgSO4), filtered, and evaporated in vacuo to afford 200 mg (95%) of the hydroxylamine isomers 47, a white solid. [The hydroxylamine isomers 47 was not characterized and was taken to the next step].

A mixture of 47 (104 mg, 0.38 mmol) in an excess amount of polyphosphoric acid (9 g) was heated to 200° C. After 30 minutes the resultant black paste was dissolved in ice-water (50 mL) and extracted with ethyl acetate (3×50 mL). The combined organic layers were then washed with saturated sodium bicarbonate solution (3×25 mL), water (2×), and brine. The organic layer was dried (MgSO4), filtered, and evaporated in vacuo. The inseparable 1:1 mixture of the phenanthridone isomers (48 and 17) was isolated in 96% yield (100 mg) as a beige solid.

1H-NMR for 48/17 [300 MHz, D6 DMSO, mixture]: δ7.24 to 7.38 (m, 3H), 7.52 (t, J=6.9 Hz, 1H), 7.64 to 7.71 (m, 2H), 7.79 to 7.89 (m, 2H), 8.22 (d, J=8.5 Hz, 1H), 8.32 (d, J=7.4 Hz, 1H), 8.45 (d, J=7.8 Hz, 1H), 8.56 to 8.60 (m, 2H), 8.75 (s, 1H).

IR (KBr): 3020, 2880, 1685, 1610 cm$^{-1}$.

Fast atom bombardment mass spectrum: m/e 274, 276 (calculated MH+ for $C_{13}H_8BrNO$=274, 276).

EXAMPLE 43

48

17

49

18

From an inseparable mixture of compounds 48 and 17 (125 mg, 0.46 mmol), using the general stannylation procedure described for compound 8, was provided 136 mg (83%) of an inseparable 1:1 mixture of stannanes 49 and 18, a white foam.

1H-NMR for 49/18 [400 MHz, CDCl3, mixture ]: δ0.36 (s, 9H), 0.40 (s, 9H), 7.29 to 7.32 (m, 3H), 7.47 (t, J=7.7 Hz, 1H), 7.56 to 7.62 (m, 2H), 7.74 (d, J=8.5 Hz, 1H), 7.80 (t, J=7.7 Hz, 1H), 8.33 (d, J=8.3 Hz, 1H), 8.31 (s, 1H), 8.35 (d, J=8.8 Hz, 1H), 8.42 (s, 1H), 8.48 (d, J=7.7 Hz, 1H), 8.55 (d, J=8.2 Hz, 1H), 10.12 (broad s, 1H), 10.23 (broad s, 1H).

IR (CHCl$_3$, mixture): 3270, 3010, 2915, 1660, 1601, 1555 cm$^{-1}$.

EXAMPLE 44

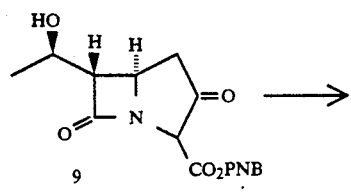

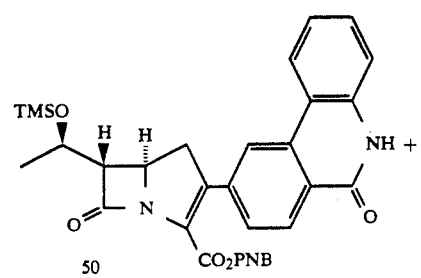

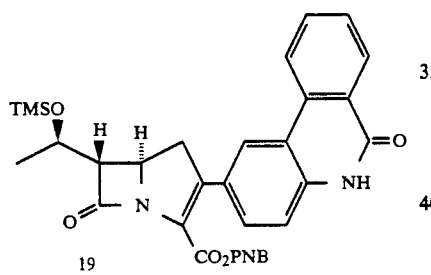

Following the general coupling procedure described for the synthesis of compound 10, the bicyclic β-keto ester 9 (162.4 mg, 0.47 mmol, 1.1 eq) was coupled to a mixture of the aryl stannanes 49 and 18 (152 mg, 0.42 mmol, 1.1 eq), to provide 172 mg (68%) of a 1.2:1.0 inseparable mixture of compounds 50 and 19, respectively, as a yellow foam.

$^1$H-NMR for 50/19 [300 MHz, CDCl$_3$, mixture]: δ0.15 (s, 18H), 1.31 (d, J=6.3 Hz,6H), 3.27 to 3.48 (complex m, 6H), 4.25 to 4.38 (complex m, 4H), 5.22 (ABq, J=13.6 Hz, Δυ$_{AB}$=50.5 Hz, 2H), 5.28 (ABq, J=13.7 Hz, Δυ$_{AB}$=53.4 Hz, 2H), 7.23 (t, 7.6 Hz, 1H), 7.32 to 7.39 (m, 4H), 7.45 to 7.54 (m, 5H), 7.62 (t, J=7.5).Hz, 1H), 7.76 (t, J=7.7 Hz, 1H), 7.95 to 8.05 (m, 3H), 8.06 (d, J=8.6 Hz, 2H), 8.14 (d, J=8.2 Hz, 1H), 8.20 (s, 1H), 8.30 (s, 1H), 8.50 (d, J=8.3 Hz, 1H), 8.56 (d, J=7.7 Hz, 1H), 11.12 (s, 1H), 11.54 (s, 1H).

IR (CHCl$_3$): 3400, 3040, 3010, 2960, 1775, 1725, 1665, 1610, 1520 cm$^{-1}$.

EXAMPLE 45

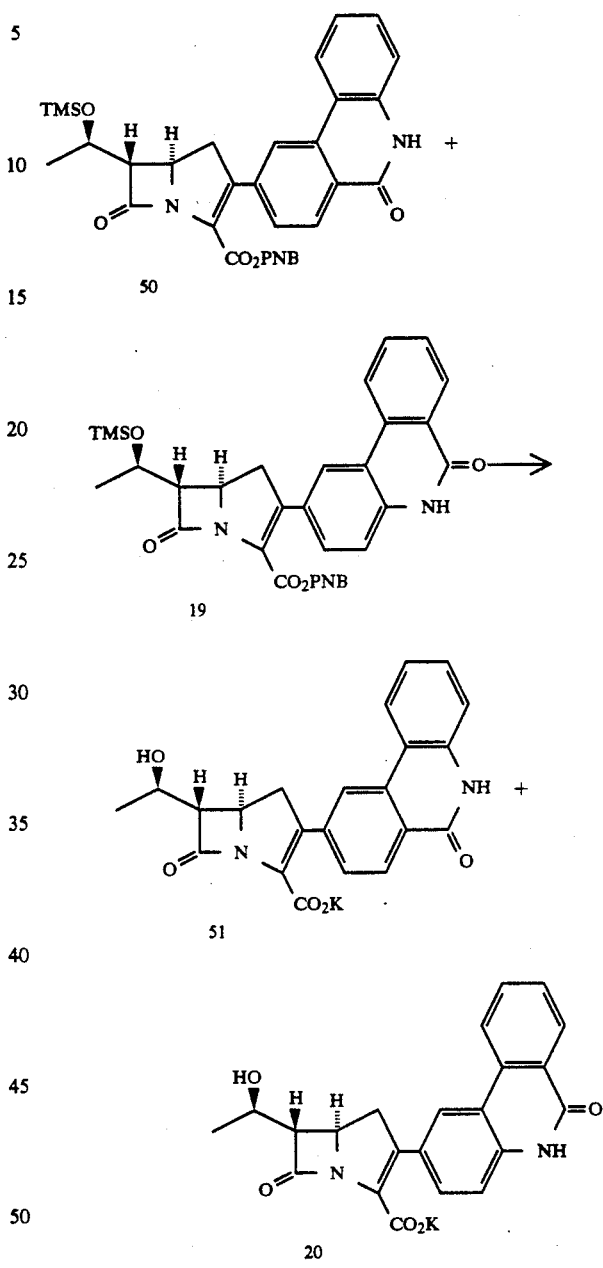

From an inseparable mixture of compounds 50 and 19 (80 mg, 0.13 mmol), using the general deprotection procedure described for compound 12, was provided 7.4 mg (13%) of carbapenem 51, a yellow solid, isolated via reverse phase prep-plate chromatography (6:1 H$_2$O/CH$_3$CN). The carbapenem 20 was also isolated in 32% yield (18.3 mg).

$^1$H-NMR for 51 [400 MHz, 2:1 D$_2$O/CD$_3$CN]; δ1.68 (d, J=6.3 Hz, 3H), 3.56 (½ ABX, J$_{AB}$=16.7 Hz, J$_{AX}$=9.7 Hz, 1H), 3.86 to 3.95 (complex m, 2H), 4.59 to 4.63 (m, 1H), 4.69 to 4.74 (m, 1H), 7.75 to 7.78 (m, 2H), 7.93 (t, J=7.9 Hz, 1H), 8.05 (d, J=8.1 Hz, 1H), 8.62 to 8.68 (m, 3H).

IR (KBr): 2970, 1750, 1660, 1650, 1610 cm$^{-1}$.

U.V. (MOPS Buffer): $\lambda_o=322$ nm, $\epsilon_o=13,300$, $\lambda_{ext1}=307$ nm, $\epsilon_{ext1}=8,840$; $\lambda_{ext2}=330$ nm, $\epsilon_{ext2}=7,970$; $\lambda_{ext3}=347$ nm, $\epsilon_{ext3}=7,100$.

EXAMPLE 46

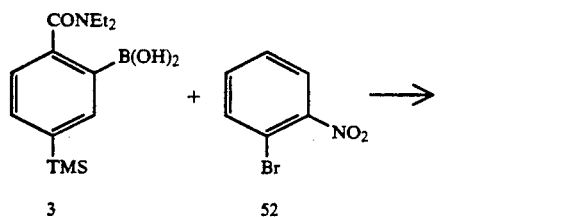

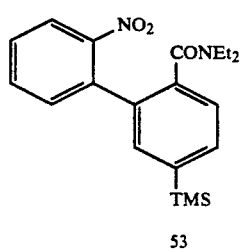

Following the Suzuki coupling procedure described for compound 5, boronic acid 3 (779.3 mg, 2.7 mmol) was coupled to aryl bromide 52 (590.5 mg, 2.9 mmol, 1.1 eq) providing 812.5 mg (82.5%) of biphenyl 53, a yellow foam.

$^1$H-NMR for 53 [400 MHz, CDCl$_3$, rotamers]: $\delta$0.24 (s, 9H), 0.80(t, J=7.1 Hz, 3H), 0.91(t, J=7.1 Hz, 3H), 2.80 to 3.67 (broad, 4H), 7.30 to 7.33 (m, 2H), 7.46 (t, J=8.1 Hz, 1H), 7.52 to 7.58 (m, 3H), 7.90 (d, J=8.8 Hz, 1H).

IR (CHCl$_3$): 3000, 2980, 1610, 1580, 1525 cm$^{-1}$.

EXAMPLE 47

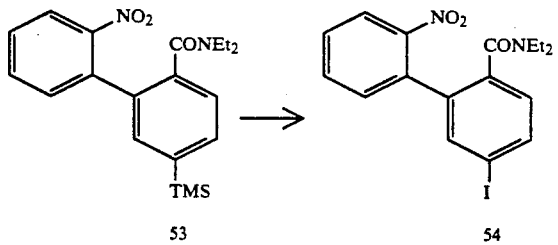

Iodine monochloride in dichloromethane (10.9 mL, 10.9 mmol, 5.0 eq) was added dropwise over 0.5 hour to a stirred solution of 53 (812.5 mg, 2.19 mmol) in dry dichloromethane (10.9 mL). The reaction mixture was then poured in ether (200 mL) and washed with saturated sodium thiosulfate solution (2×25 mL), water, saturated bicarbonate solution (2×25 mL), water and brine. The etheral layer was then dried (MgSO$_4$), filtered, and evaporated in vacuo. Purification using flash column chromatography (30% EtOAc/hex) afforded 887.7 mg (95.4%) of 54, a yellow foam.

$^1$H-NMR for 54 [400 MHz, CDCl$_3$, rotamers]: $\delta$0.75 (t, J=7.0 Hz, 3H), 0.93 (t, J=7.0 Hz, 3H), 2.82 to 3.60 (broad, 4H), 7.07 (d, J=8.1 Hz, 1H), 7.46 to 7.51 (m, 2H), 7.56 to 7.60 (m, 2H), 7.73 (d, J=8.1 Hz, 1H), 7.97 (d, J=8.1 Hz, 1H).

IR (CHCl$_3$): 3000, 2980, 1620, 1580, 1525 cm$^{-1}$.

EXAMPLE 48

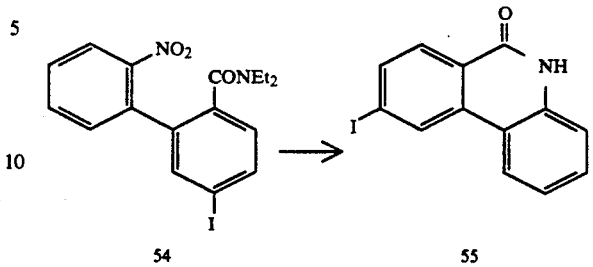

To a stirred solution of 54 (158.0 mg, 0.37 mmol) in 3:2:2 AcOH/EtOH/THF (7.0 mL) was added iron powder (103.8 mg, 1.86 mmol, 5.0 eq), and the reaction mixture was stirred at reflux until a white solid had separated (30 minutes). The reaction mixture was poured into ethyl acetate (200 mL) and washed with saturated sodium bicarbonate solution (1×25 mL), water, and brine. The organic layer was dried (MgSO$_4$) filtered and evaporated in vacuo. Chloroform (~10 mL) was added and the product was filtered to afford 119.0 mg (99.5%) of 55, a white solid.

$^1$H-NMR for 55 [400 MHz, D$_6$ DMSO]: $\delta$7.24 (t, J=7.7 Hz, 1H), 7.34 (d, J=8.1 Hz, 1H), 7.50 (t, J=7.6 Hz, 1H), 8.42 (d, J=8.1 Hz, 1H), 8.89 (s, 1H).

IR(KBr): 3010, 2990, 2870, 1665, 1600, 1585 cm$^{-1}$.

EXAMPLE 49

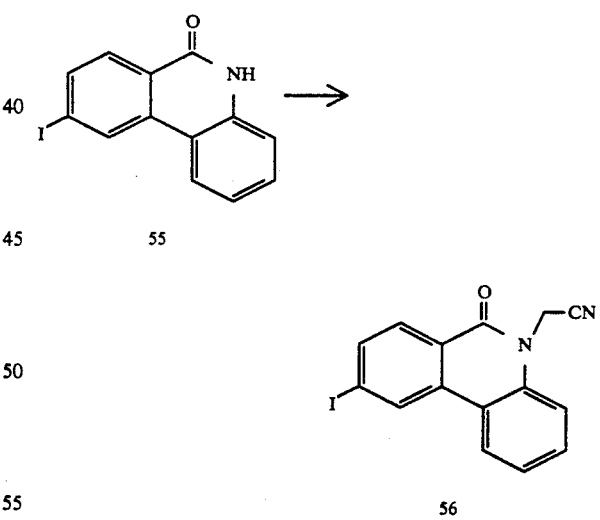

From 55 (143.0 mg, 0.44 mmol) and bromoacetonitrile (34.1 μL, 0.49 mmol, 1.1 eq), using the general alkylating procedure described for compound 24, was provided 124.1 mg (77.4%) of the N-cyanomethyl compound 56, a beige solid.

$^1$H-NMR for 56 [400 MHz, D$_6$ DMSO]: $\delta$5.50 (s, 2H), 7.42 (t, J=7.1 Hz, 1H), 7.66 to 7.72 (m, 2H), 8.01 (d, J=8.5 Hz, 1H), 8.06 (d, J=8.4 Hz, 1H), 8.59 (d, J=8.1 Hz, 1H), 8.94 (s, 1H).

IR(KBr): 3060, 2990, 2950, 1660, 1595 cm$^{-1}$.

EXAMPLE 50

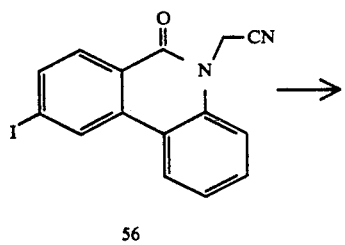

56

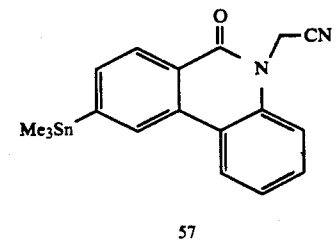

57

From 56 (120.0 mg, 0.33 mmol), using the general stannylation procedure described for compound 8, was provided 94.5 (70%) of stannane 57, a white solid.

$^1$H-NMR for 56 [400 MHz, CDCl$_3$]: δ0.39 (s, 9H), 5.34 (s, 2H), 7.36 to 7.41 (m, 2H), 7.59 (t, J=7.8 Hz, 1H), 7.72 (d, J=7.7 Hz, 1H), 8.34 to 8.41 (m, 3H).

IR (CHCl$_3$): 3030, 3010, 2980, 1660, 1610, 1595, 1580 cm$^{-1}$.

EXAMPLE 51

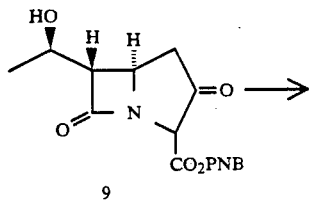

9

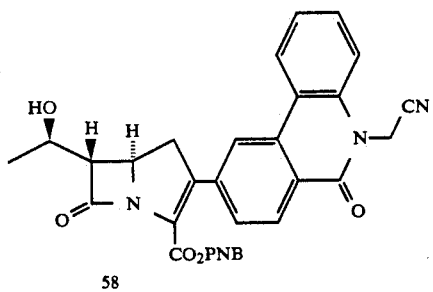

58

To a stirred solution of the bicyclic β-keto ester 9 (73.8 mg, 0.21 mmol) in dry THF (1.06 ml) at −78° C. under N$_2$ was added diisopropylamine (32.7 μl, 0.23 mmol, 1.1 eq). The resultant yellow mixture was stirred for 10 minutes before trifluoromethanesulfonic anhydride (39.2 μl, 0.23 mmol, 1.1 eq) was added. After 20 minutes the reaction mixture was treated sequentially with anhydrous N-methylpyrrolidinone (1.06 mL), the Pd$_2$(dba)$_3$•CHCl$_3$ catalyst (4.4 mg, 4.2×10$^{-3}$ mmol, 2.0 mol %), the aryl stannane 57 (56.1 mg, 0.14 mmol, 0.66 eq), and zinc chloride (0.14 mL, 0.14 mmol, 0.66 eq). The low temperature bath was then removed and the reaction vessel was placed in a warm water bath to quickly reach ambient temperature. The resulting tea-color solution was stirred for 50 minutes at ambient temperature.

The reaction was then poured into ether (100 mL) and washed with water (3×) and brine. The organic layer was dried (MgSO$_4$), filtered, and evaporated in vacuo. Purification using flash chromatography (70%, EtOAc/hex) provided 49.4 mg (61.9%) of the coupled product 58, a white solid.

$^1$H-NMR [400 MHz, D$_6$DMSO]: δ1.18 (d, J=6.2 Hz, 3H), 3.24 to 3.31 (m, 1H), 3.47 to 3.49 (m, 1H), 3.70 (½ABX, J$_{AB}$=18.4 Hz, J$_{AX}$=8.4 Hz, 1H), 4.00 to 4.05 (m, 1H), 4.31 (t, J=8.3 Hz, 1H), 5.24 (AB$_q$, J=14.5 Hz, Δυ$_{AB}$=44.7 Hz, 2H), 5.50 (s, 2H), 7.39 (d, J=8.4 Hz, 3H), 7.61 (d, J=8.1 Hz, 1H), 7.67 (d, J=3.9 Hz, 2H), 7.93 (d, J=8.6 Hz, 2H), 8.23 (d, J=8.4 Hz, 1H), 8.45 (d, J=7.8 Hz, 1H), 8.51 (s, 1H).

IR (KBr): 2920, 2855, 1775, 1720, 1660, 1605, 1518 cm$^{-1}$.

U.V. (CH$_3$CN): λ=309 nm, ε=6,317.

EXAMPLE 52

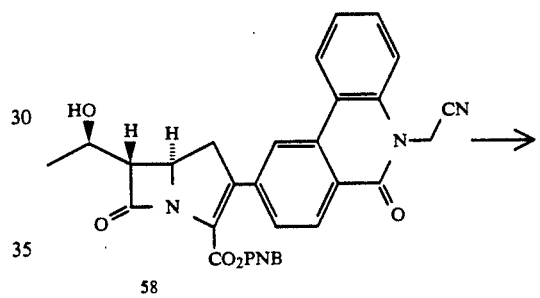

58

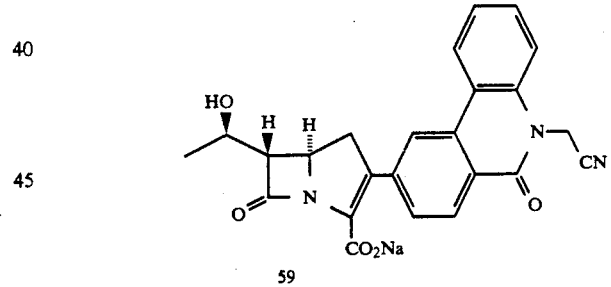

59

From 58 (55.4 mg, 9.8×10$^{-2}$ mmol) and 1.0M aqueous sodium bicarbonate solution (0.11 mL, 0.11 mmol, 1.2 eq), using the deprotection procedure described for compound 27, was provided 17.5 mg (39.5%) of carbapenem 59, a white solid.

$^1$H-NMR [400 MHz, 2:1 D$_2$O/CD$_3$CN]: δ1.62 (d, J=6.5 Hz, 3H), 3.50 (½ABX, J$_{AB}$=16.5 Hz, J$_{AX}$=9.8 Hz, 1H), 3.81 to 3.89 (complex m, 2H), 4.53 to 4.57 (m, 1H), 4.65 (t, J=9.1 Hz, 1H), 5.74 (s, 2H), 7.81 (t, J=7.6 Hz, 1H), 7.90 (d, J=8.1 Hz, 1H), 7.98 (d, J=8.4 Hz, 1H), 8.03 (t, J=7.5 Hz, 1H), 8.59 (d, J=8.4 Hz, 1H), 8.65 (s, 1H), 8.71 (d, J=8.1 Hz, 1H).

IR(KBr): 2970, 1750, 1645, 1610, 1585 cm$^{-1}$.

U.V. (MOPS Buffer): λ$_o$=328 nm, ε$_o$=16,500; λ$_{ext1}$=331 nm, ε$_{ext1}$=10,000; λ$_{ext2}$=345 nm, ε$_{ext2}$=9,590.

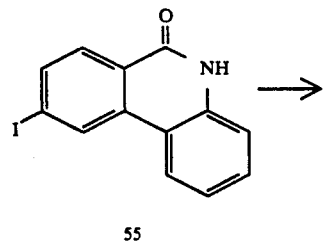

55

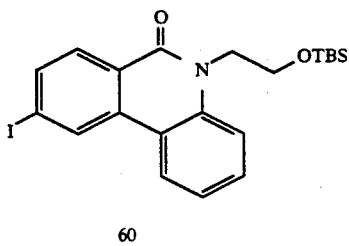

60

From 55 (200 mg, 0.62 mmol) and 2-bromo(t-butyldimethylsilyl)ethanol (0.23 mL, 1.24 mmol, 2.0 eq), using the general alkylating procedure described for compound 24, was provided 121.6 mg (40.7%) of 60, a white solid.

1H NMR for 60 [400 MHz,CDCl3]: δ −0.08 (s, 6H), 0.79 (s, 9H), 3.99 (t, J=6.2 Hz, 2H), 4.49(t, J=6.2 Hz, 2H), 7.27 (t, J=7.6 Hz, 1H), 7.50 (t, J=7.8 Hz, 1H), 7.64 (d, J=8.7 Hz, 1H), 7.85 (d, J=8.4 Hz, 1H), 8.14 (d, J=8.1 Hz, 1H), 8.19 (d, J=8.6 Hz, 1H), 8.59 (s, 1H).

IR(CHCl3): 3000, 2950, 2930, 2860, 2360, 1640, 1605, 1590, 1575.

EXAMPLE 54

60

61

Iodide 60 (112.2 mg, 0.234 mmol) was stannylated following the general stannylation procedure described for compound 8. The crude TBS-protected stannane was then redissolved in dry THF (4.7 mL), and tetrabutylammonium fluoride (0.26 mL, 0.26 mmol, 1.1 eq) was added at 0° C. The reaction mixture was then stirred for 15 minutes at 0° C., poured into ethyl acetate, and washed with water (1×), saturated ammonium chloride solution (1×), water (2×), and brine. The organic layer was dried (MgSO4), filtered, and evaporated in vacuo. Purification using flash chromatography (45% EtOAc/hex) provided 76.8 mg (85%) of stannane 61, a white solid.

1H-NMR for 61 [400 MHz,CDCl3]: δ0.39 (s, 9H), 2.98 (t, J=4.9 Hz, 1H), 4.10(t, J=5.3 Hz, 2H), 4.63 (t, J=5.5 Hz, 2H), 7.33 (t, J=6.9 Hz, 1H), 7.45 (d, J=7.6 Hz, 1H), 7.51 (d, J=7.8 Hz, 1H), 7.71 (d, J=7.7 Hz, 1H), 8.36 (d, J=8.2 Hz, 1H), 8.39 (s, 1H), 8.42 (d, J=7.9 Hz, 1H).

IR(CHCl3): 3560 to 3200, 3000, 2920, 1630, 1605, 1580 cm−1.

EXAMPLE 55

9

62

To a stirred solution of the bicyclic β-keto ester 9 (158.3 mg, 0.45 mmol) in dry THF (2.3 mL) at −78° C. under N2 was added diisopropylamine (70.0 μL, 0.50 mmol, 1.1 eq). The resultant yellow mixture was stirred for 10 minutes before trifluoromethanesulfonic anhydride (84.1 μL, 0.50 mmol, 1.1 eq) was added. After 15 minutes triethylamine (69.7 μL, 0.50 mmol, 1.1 eq), followed by the trimethylsilyl trifluoromethanesulfonate (96.6 μL, 0.50 mmol, 1.1 eq), was added and the reaction mixture was stirred for 20 minutes.

The reaction mixture was then treated sequentially with anhydrous N-methylpyrrolidinone (2.3 mL), the Pd2(dba)3•CHCl3 catalyst (9.4 mg, 9.1×10−3 mmol, 2.0 mol %), the aryl stannane 61 (117.0 mg, 0.30 mmol, 0.66 eq), and zinc chloride (0.30 mL, 0.30 mmol, 0.66 eq). The low temperature bath was then removed and the reaction vessel was placed in a warm water bath to quickly reach ambient temperature. The solution was stirred for 30 minutes at ambient temperature.

The reaction was then poured into ether (150 mL) and washed with water (3×) and brine. The organic layer was dried (MgSO4), filtered and evaporated in vacuo. Purification using flash chromatography (60% EtOAc/hex) provided 88.6 mg (45.5%) of the coupled product 62, a yellow oil.

1H-NMR for 62 [400 MHz, CDCl3]δ0.14 (s, 9H), 1.30 (d, J=6.2 Hz, 3H), 2.86 (t, J=4.8 Hz, 1H), 3.28 to 3.33 (complex m, 2H), 3.41 (½ABX, JAB=18.5 Hz, JAX=8.8 Hz, 1H), 4.08 (complex m, 2H), 4.24 to 4.28 (m, 1H), 4.34 (t, J=9.4 Hz, 1H), 4.61 (t, J=5.1 Hz, 2H), 5.20 (ABq, JAB=13.5 Hz, ΔυAB=66.7 Hz, 2H), 7.22 to 7.28 (m, 3H), 7.43 to 7.47 (m, 2H), 7.50 (d, J=7.1 Hz, 1H), 7.89 (d, J=8.8 Hz, 2H), 8.03 (d, J=7.5 Hz, 1H), 8.16 (s, 1H), 7.44 (d, J=8.3 Hz, 1H).

IR(CHCl₃): 3680 to 3200, 3010, 2960, 1780, 1730, 1640, 1610, 1585, 1525 cm⁻¹.
U.V. (CH₃CN): λ=314 nm, ε=16,210

EXAMPLE 56

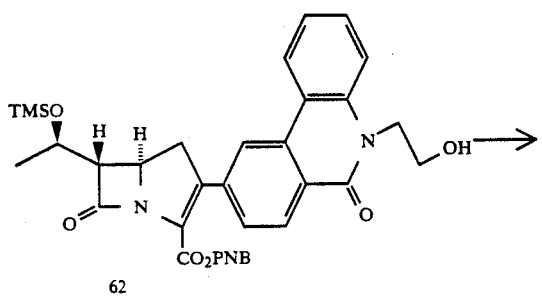

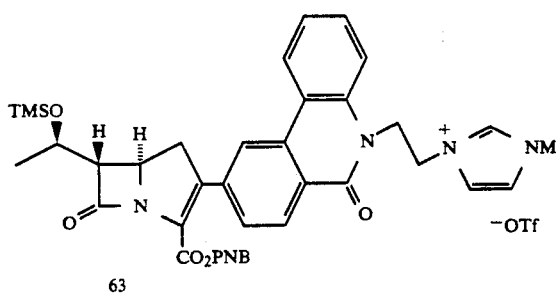

From 62 (88.6 mg, 0.14 mmol), using the general procedure described for the preparation of quarternary salt 13, was isolated 71 mg (60%) of the N-methylimidazolium compound 63, a yellow foam.

¹H-NMR for 63 [400 MHz, CDCl₃]: δ0.14 (s, 9H), 1.30 (d, J=6.2 Hz, 3H), 3.40 to 3.48 (complex m, 2H), 3.55 (½ABX, J$_{AB}$=18.4 Hz, J$_{AX}$=8.7 Hz, 1H), 3.91 (s, 3H), 4.34 to 4.44 (complex m, 2H), 4.62 (t, J=6.8 Hz, 2H), 4.80 (t, J=6.6 Hz, 2H), 5.23 (AB$_q$, J=13.5 Hz, Δν$_{AB}$=70.6 Hz, 2H), 7.35 (d, J=8.7 Hz, 1H), 7.45 (d, J=8.5 Hz, 2H), 7.69 to 7.75 (m, 2H), 7.86 (t, J=7.8 Hz, 1H), 7.96 (d, J=8.8 Hz, 1H), 8.01 (d, J=8.7 Hz, 2H), 8.08 (d, J=7.7 Hz, 1H), 8.18 (s, 1H), 8.28 (d, J=7.0 Hz, 1H), 8.45 (d, J=8.0 Hz, 1H), 8.5 (s, 1H).

IR(CHCl₃): 3030, 3010, 2880, 1780, 1730, 1630, 1610, 1580, 1520 cm⁻¹.
U.V. (CH₃CN) λ=340 nm, ε=9,500.

EXAMPLE 57

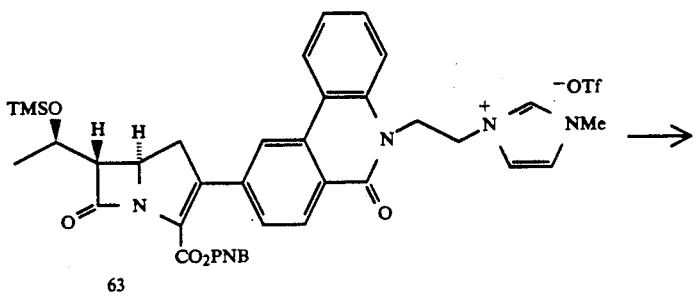

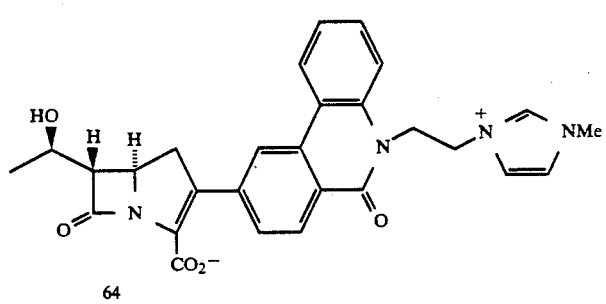

Acetic acid (11.5 μL, 0.20 mmol. 3.0 eq) was added to a stirred solution of 63 (57.3 mg, 6.7×10⁻² mmol) in 1.3:1.3:1.0 THF/EtOH/H₂O, and the reaction mixture was stirred for 1 hour at room temperature. Hydrochloric acid in ether (67.0 μL, 6.7×10⁻² mmol, 1.0 eq) was then added at 0° C., and the reaction mixture was stirred for 40 minutes at 0° C. Aqueous sodium bicarbonate solution (301 μL, 0.301 mmol, 4.5 eq) was added at 0° C., followed by 10% Pd/C catalyst (17.0 mg, 30% wt), and the reaction mixture was hydrogenated under a H₂ balloon at ambient temperature for 40 minutes. Work-up following the procedure described for carbapenem 12 provided crude 64, which was purified twice using Analtech brand reverse phase prep-plates (2:1 H₂O/CH₃CN) affording 3.5 mg (10.5%) of carbapenem 64, a yellow solid.

¹H-NMR for 64 [400 MHz, 2:1 D₂O/CD₃CN]:δ1.76 (d, J=6.4 Hz, 3H), 3.65 (½ABX, J$_{AB}$=16.5 Hz, J$_{AX}$=8.8 Hz, 1H), 3.94 to 3.96 (m, 1H), 4.01 (½ABX, J$_{AB}$=16.7 Hz, J$_{AX}$=8.6 Hz, 1H), 4.20 (s, 3H), 4.67 to 4.71 (m, 1H), 4.77 to 4.80 (m, 1H), 5.10 (t, J=5.7 Hz, 2H), 5.31 (t, J=5.7 Hz, 2H), 7.76 (s, 1H), 7.81 (s, 1H), 7.92 to 7.95 (m, 2H), 8.08 to 8.13 (m, 3H), 8.65 (d, J=8.5 Hz, 1H), 8.85 (s, 1H), 8.91 (d, J=7.7 Hz, 1H).

IR(KBr): 1750, 1640, 1610, 1590, 1575 cm⁻¹.
U.V.(MOPS Buffer): λ$_o$=327 nm, ε$_o$=12,150; λ$_{ext}$=331 nm, ε$_{ext}$=7300.

What is claimed is:

1. A compound of the formula:

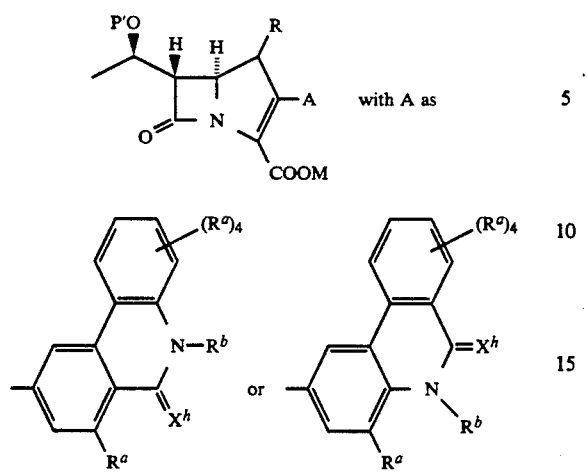 with A as

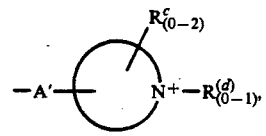

wherein:
R is H or CH$_3$;
P' is a removable protecting group for hydroxy;
X$^h$ is O or S;
R$^a$ are independently selected from the group consisting of hydrogen and the radicals set out below, provided that one but not more than one R$^a$ or R$^b$ is or contains a Type I substituent, the remaining non-hydrogen substituents being selected from Type II, and in total not more than four R$^a$ and R$^b$ radicals are other than hydrogen:

I. a)

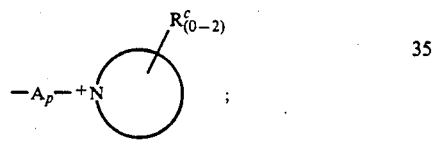

where
A is (CH$_2$)$_m$—Q—(CH$_2$)$_n$, where m is 0 to 6 and n is 1 to 6 and Q is a covalent bond, O, S, SO, SO$_2$, NH, —SO$_2$NH—, —NHSO$_2$—, —CONH—, —NH-CO—, —SO$_2$N(C$_1$-C$_4$alkyl)—, —N(C$_1$-C$_4$alkyl)-SO$_2$—, —CON(C$_1$-C$_4$alkyl)—, —N(C$_1$-C$_4$alkyl)-CO—, —CH=CH—, —CO—, —OC(O)—, —C(O)O— or N(C$_1$-C$_4$alkyl) and (CH$_2$)$_m$ is attached to the phenanthridonyl moiety;

is a 5- or 6-membered monocyclic heterocycle or an 8-, 9- or 10-membered bicyclic heterocycle, the heterocycle containing a first nitrogen in an aromatic 5- or 6-membered first ring, with attachment of the heterocycle to A by way of said first nitrogen and said first nitrogen is quaternary by virtue of the attachment and ring bonds, with the first ring containing 0 or 1 of either O or S, with the first ring containing 0 to 3 additional nitrogen atoms, with the first ring optionally fused to a 3- or 4-membered moiety to form the optional second ring, with the moiety containing at least one carbon atom, with the moiety containing 0 or 1 of either O or S, with the moiety containing 0 to 2 nitrogen atoms, and with the moiety being saturated or unsaturated and the second ring aromatic or non-aromatic;

R$^c$ is R$^a$ as defined under II below, hydrogen, or —NR$^y$R$^z$(where R$^y$ and R$^z$ are defined in II below), but independently selected from R$^a$ and from each other if more than one R$^c$ is present, and is attached to a carbon ring atom or a nitrogen heteroatom the valency of which is not satisfied by the ring bonds;
p is 0 or 1; b)

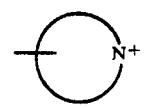

where

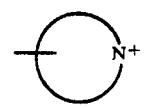

is a 5- or 6-membered monocyclic heterocycle or an 8-, 9- or 10-membered bicyclic heterocycle, the heterocycle containing a first nitrogen in an aromatic 5- or 6-membered first ring, with said first nitrogen quaternary by virtue of a substituent R$^d$ in addition to the ring bonds thereto, with said first nitrogen neutral in the absence of a substituent R$^d$, with attachment of the heterocycle to A' by way of a carbon atom of a ring, with the first ring containing 0 or 1 of either O or S, with the first ring containing 0 to 2 additional nitrogen atoms, with the first ring optionally fused to a 3- or 4-membered moiety to form the optional second ring, with the moiety containing at least one carbon atom, with the moiety containing 0 or 1 of either O or S, with the moiety containing 0 to 2 nitrogen atoms, and with the moiety being saturated or unsaturated and the second ring aromatic or non-aromatic;

R$^c$ is defined above;
R$^d$ is hydrogen, NH$_2$, O$^-$ or C$_1$-C$_4$alkyl (where the alkyl group is optionally mono-substituted with R$^q$ as defined under IIc below);
A' is (CH$_2$)$_m$—Q—(CH$_2$)$_n$, where m is 0 to 6 and n is 0 to 6, Q is given above, and when m and n are 0 then Q is not a covalent bond;
c) —A$_p$—N$^+$R$^y$(R$^w$)$_{(0-1)}$(R$^z$) where
R$^y$ and R$^z$ are as defined under II below,
R$^y$ and R$^z$ may further be together a C$_2$-C$_4$ alkylidene radical to form a ring (optionally mono-substituted with R$^q$ as defined below) interrupted by N(O)R$^e$ or N$^+$(R$^e$)$_2$ (where R$^e$ is hydrogen, C$_1$-C$_4$alkyl, or C$_1$-C$_4$alkyl substituted with R$^q$ defined below),
R$^w$ is hydrogen, C$_{1-4}$ alkyl, O$^-$, NH$_2$ or absent in which case the nitrogen is neutral,
R$^w$, R$^y$ and R$^z$ may further together form a C$_5$-C$_{10}$ tertiary alkylidene radical which with N$^+$ forms a bicyclic ring, where the tertiary alkylidene radical is optionally mono-substituted with R$^q$ as defined below and where the tertiary carbon of the tertiary alkylidene radical is optionally replaced with nitrogen, N$^+$R$^e$ (where R$^e$ is defined above), or N$^+$—O$^-$, p is 0 or 1, and
A is as defined above; d)

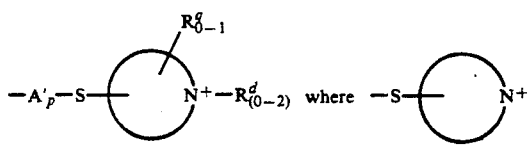

is a 5- or 6-membered monocyclic heterocycle or an 8-, 9- or 10-membered bicyclic heterocycle, the heterocycle containing a first nitrogen in a first ring, with the first ring saturated or unsaturated and non-aromatic, with the first nitrogen quaternary by virtue of one or two substituents $R^d$ in addition to the ring bonds thereto, with the first nitrogen alternatively neutral by virtue of zero or one substituents $R^d$ in addition to the ring bonds thereto, with attachment of the heterocycle to A' by way of a carbon atom or non-quaternary nitrogen atom of a ring, with the first ring containing in addition to carbon and the first nitrogen 0 to 1 of a member selected from the group consisting of the non-quaternary nitrogen of attachment, O, S, S(O), $S(O)_2$ and $NR^e$ where $R^e$ is defined above, with the first ring optionally fused to a 2-, 3- or 4-membered moiety to form the optional second ring, with the moiety optionally containing in addition to carbon the non-quaternary nitrogen of attachment, and with the moiety saturated or unsaturated and the second ring non-aromatic;

$R^d$ is defined above and where more than one $R^d$ is present on a nitrogen, at least one $R^d$ is hydrogen or $C_1$-$C_4$alkyl;

A' is defined above; and p is defined above;

$R^q$ is defined below;

with the Type I, $R^a$ or $R^b$ substituent balanced with the anionic form of Z where:

Z is selected from the group consisting of alkylsulfonyloxy, substituted alkylsulfonyloxy, arylsulfonyloxy, substituted arylsulfonyloxy, fluorosulfonyloxy, and halogen;

II.
a) a trifluoromethyl group: —$CF_3$;
b) a halogen atom: —Br, —Cl, —F, or —I;
c) $C_1$-$C_4$ alkoxy radical: —$OC_{1-4}$ alkyl, wherein the alkyl is optionally mono-substituted by $R^q$, where $R^q$ is a member selected from the group consisting of —OH, OP', —$OCH_3$, —CN, —$C(O)NH_2$, —$OC(O)NH_2$, CHO, —$OC(O)N(CH_3)_2$, —$SO_2NH_2$, —$SO_2N(CH_3)_2$, —$SOCH_3$, —$SO_2CH_3$, —F, —$CF_3$, —$COOM^a$ (where $M^a$ is hydrogen, alkali metal, methyl or phenyl), tetrazolyl (where the point of attachment is the carbon atom of the tetrazole ring and one of the nitrogen atoms is monosubstituted by $M^a$ as defined above) and —$SO_3M^b$ (where $M^b$ is hydrogen or an alkali metal or M);

d) a hydroxy group: —OH or OP';
e) a carbonyloxy radical: —O(C=O)$R^s$, where $R^s$ is $C_{1-4}$ alkyl or phenyl, each of which is optionally mono-substituted by $R^q$ as defined above;

f) a carbamoyloxy radical: —O(C=O)N($R^y$)$R^z$ where $R^y$ and $R^z$ are independently H, $C_{1-4}$ alkyl (optionally mono-substituted by $R^q$ as defined above), together a 3- to 5-membered alkylidene radical to form a ring (optionally substituted with $R^q$ as defined above) or together a 2- to 4-membered alkylidene radical, interrupted by —O—, —S—, —S(O)— or —$S(O)_2$—, to form a ring (where the ring is optionally mono-substituted with Rq as defined above);

g) a sulfur radical: —$S(O)_n$—$R^s$ where n=0-2, and $R^s$ is defined above;

h) a sulfamoyl group: —$SO_2N(R^y)R^z$ where $R^y$ and $R^z$ are as defined above;

i) azido: $N_3$;

j) a formamido group: —N($R^t$)(C=O)H, where $R^t$ is H or $C_{1-4}$ alkyl, and the alkyl thereof is optionally mono-substituted by $R^q$ as defined above;

k) a ($C_1$-$C_4$ alkyl)carbonylamino radical: —N($R^t$)(C=O)$C_{1-4}$ alkyl, where $R^t$ is as defined above, and the alkyl group is also optionally mono-substituted by $R^q$ as defined above;

l) a ($C_1$-$C_4$ alkoxy) carbonylamino radical: —N($R^t$)(C=O)O$C_{1-4}$ alkyl, where $R^t$ is as defined above, and the alkyl group is also optionally mono-substituted by $R^q$ as defined above;

m) a ureido group: —N($R^t$)(C=O)N($R^y$)$R^z$ where $R^t$, $R^y$ and $R^z$ are as defined above;

n) a sulfonamido group: —N($R^t$)$SO_2R^s$, where $R^s$ and $R^t$ are as defined above;

o) a cyano group: —CN;

p) a formyl or acetalized formyl radical: —(C=O)H or —CH(OCH$_3$)$_2$;

q) ($C_1$-$C_4$ alkyl)carbonyl radical wherein the carbonyl is acetalized: —C(OCH$_3$)$_2C_{1-4}$ alkyl, where the alkyl is optionally mono-substituted by $R^q$ as defined above;

r) carbonyl radical: —(C=O)$R^s$, where $R^s$ is as defined above;

s) a hydroximinomethyl radical in which the oxygen or carbon atom is optionally substituted by a $C_1$-$C_4$ alkyl group: —(C=NO$R^z$)$R^y$ where $R^y$ and $R^z$ are as defined above, except they may not be joined together to form a ring;

t) a ($C_1$-$C_4$ alkoxy)carbonyl radical: —(C=O)O$C_{1-4}$ alkyl, where the alkyl is optionally mono-substituted by $R^q$ as defined above;

u) a carbamoyl radical: —(C=O)N($R^y$)$R^z$ where $R^y$ and $R^z$ are as defined above;

v) an N-hydroxycarbamoyl or N($C_1$-$C_4$ alkoxy)carbamoyl radical in which the nitrogen atom may be additionally substituted by a $C_1$-$C_4$ alkyl group: —(C=O)—N(O$R^y$)$R^z$ where $R^y$ and $R^z$ are as defined above, except they may not be joined together to form a ring;

w) a thiocarbamoyl group: —(C=S)N($R^y$)($R^z$) where $R^y$ and $R^z$ are as defined above;

x) carboxyl: —COO$M^b$, where $M^b$ is as defined above;

y) thiocyanate: —SCN;

z) trifluoromethylthio: —$SCF_3$;

aa) tetrazolyl, where the point of attachment is the carbon atom of the tetrazole ring and one of the nitrogen atoms is mono-substituted by hydrogen, an alkali metal or a $C_1$-$C_4$ alkyl optionally substituted by $R^q$ as defined above;

ab) an anionic function selected from the group consisting of: phosphono [P=O(O$M^b$)$_2$]; alkylphosphono {P=O(O$M^b$)—[O($C_1$-$C_4$ alkyl)]}; alkylphosphinyl [P=O(O$M^b$)—($C_1$-$C_4$alkyl)]; phosphoramido [P=O(O$M^b$)N($R^y$)$R^z$ and P=O(O$M^b$)NH$R^x$]; sulfino (SO$_2M^b$); sulfo (SO$_3M^b$);

acylsulfonamides selected from the structures CONM$^b$SO$_2$R$^x$, CONM$^b$SO$_2$N(R$^y$)R$^z$, SO$_2$NM$^b$CON(R$^y$)R$^z$; and SO$_2$NM$^b$CN, where R$^x$ is phenyl or heteroaryl, where heteroaryl is a monocyclic aromatic hydrocarbon group having 5 or 6 ring atoms, in which a carbon atom is the point of attachment, in which one of the carbon atoms has been replaced by a nitrogen atom, in which one additional carbon atom is optionally replaced by a heteroatom selected from O or S, and in which from 1 to 2 additional carbon atoms are optionally replaced by a nitrogen heteroatom, and where the phenyl and heteroaryl are optionally mono-substituted by R$^q$, as defined above; M$^b$ is as defined above; and R$^y$ and R$^z$ are as defined above;

ac) C$_5$–C$_7$ cycloalkyl group in which one of the carbon atoms in the ring is replaced by a heteroatom selected from O, S, NH or N(C$_1$–C$_4$ alkyl) and in which one additional carbon atom may be replaced by NH or N(C$_1$–C$_4$ alkyl), and in which at least one carbon atom adjacent to each nitrogen heteroatom has both of its attached hydrogen atoms replaced by one oxygen thus forming a carbonyl moiety and there are one or two carbonyl moieties present in the ring;

ad) C$_2$–C$_4$ alkenyl radical, optionally mono-substituted by one of the substituents a) to ac) above and phenyl which is optionally substituted by R$^q$ as defined above;

ae) C$_2$–C$_4$ alkynyl radical, optionally mono-substituted by one of the substituents a) to ac) above;

af) C$_1$–C$_4$ alkyl radical;

ag) C$_1$–C$_4$ alkyl mono-substituted by one of the substituents a)–ac) above;

ah) a 2-oxazolidinonyl moiety in which the point of attachment is the nitrogen atom of the oxazolidinone ring, the ring oxygen atom is optionally replaced by a heteroatom selected from —S— and NR$^t$ (where R$^t$ is as defined above) and one of the saturated carbon atoms of the oxazolidinone ring is optionally mono-substituted by one of the substituents a) to ag) above;

R$^b$ is —H, —OH, OP', —CF$_3$, —(C=O)R$^s$, —S(O)$_n$R$^s$ where n=0-2, —SO$_2$NR$^y$R$^z$, —(C=O)OC$_{1-4}$alkyl, —(C=O)N(R$^y$)R$^z$, —(C=O)N(OR$^y$)R$^z$, —(C=S)N(R$^y$)R$^z$, —NH$_2$, C$_{1-4}$ alkoxy optionally mono-substituted with R$^q$, R$^x$ as defined above, a Type I. b) or d) substituent as defined above, C$_{1-4}$ alkyl optionally mono-substituted on an alpha carbon or higher by one of the substituents Type I. a) or c) or Type II. a)–ae) as defined for R$^a$ above; and M is a removable protecting group for carboxy.

2. The compound of claim 1 where M is selected from the group consisting of alkyl, substituted alkyl, benzyl, substituted benzyl, aryl, substituted aryl, allyl, substituted allyl, and triorganosilyl.

3. The compound of claim 1 wherein M is selected from the group consisting of benzhydryl, p-nitrobenzyl, 2-naphthylmethyl, allyl, 2-chloroallyl, benzyl, 2,2,2-trichloroethyl, trimethylsilyl, t-butyldimethylsilyl, t-butyldiphenylsilyl, 2-(trimethylsilyl)ethyl, phenacyl, p-methoxybenzyl, acetonyl, o-nitrobenzyl, 4-pyridylmethyl and t-butyl.

4. The compound of claim 1 wherein P' is selected from the group consisting of trialkylsilyl, aryl(alkyl)alkoxysilyl, alkoxy(diaryl)silyl, (diaryl)alkylsilyl, alkyloxycarbonyl, substituted alkyloxycarbonyl, benzyloxycarbonyl, substituted benzyloxycarbonyl, allyloxycarbonyl and substituted allyloxycarbonyl.

5. The compound of claim 1 wherein P' is selected from the group consisting of t-butylmethoxyphenylsilyl, t-butoxydiphenylsilyl, trimethylsilyl, triethylsilyl, t-butyldimethylsilyl, o-nitrobenzyloxycarbonyl, p-nitrobenzyloxycarbonyl, benzyloxycarbonyl, t-butyloxycarbonyl, 2,2,2,-trichloroethyloxycarbonyl and allyloxycarbonyl.

6. A compound of the formula:

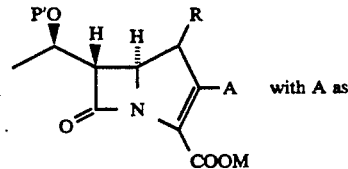

with A as

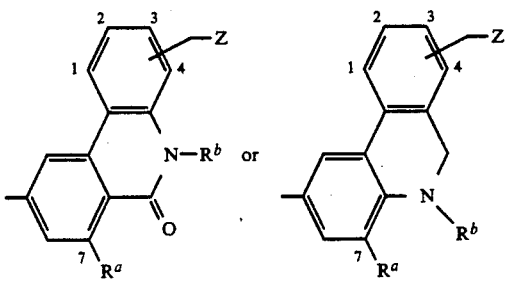

wherein

R is —H or —CH$_3$;

R$^a$ is selected from the group consisting of H, OP', Cl, Br, I, SCH$_3$, CN, CHO, SOCH$_3$, SO$_2$CH$_3$, CO$_2$M, CH$_2$OP' or CONH$_2$;

R$^b$ is H, OP', CH$_2$SCH$_3$, CH$_2$CN, CH$_2$CHO, CH$_2$SOCH$_3$, CH$_2$SO$_2$CH$_3$, CH$_2$CO$_2$M, CH$_2$OP', CH$_2$CH$_2$OP' or CH$_2$CONH$_2$;

P' is a removable protecting group for hydroxy;

M is a removable protecting group for carboxy; and

Z is selected from the group consisting of alkylsulfonyloxy, substituted alkylsulfonyloxy, arylsulfonyloxy, substituted arylsulfonyloxy, fluorosulfonyloxy, and halogen; and with the proviso that the —CH$_2$—Z moiety is in the 3-or 4-position of the phenanthridone as numbered above.

7. The compound of claim 6 where M is selected from the group consisting of alkyl, substituted alkyl, benzyl, substituted benzyl, aryl, substituted aryl, allyl, substituted allyl, and triorganosilyl.

8. The compound of claim 6 wherein M is selected from the group consisting of benzhydryl, p-nitrobenzyl, 2-naphthylmethyl, allyl, 2-chloroallyl, benzyl, 2,2,2-trichloroethyl, trimethylsilyl, t-butyldimethylsilyl, t-butyldiphenylsilyl, 2-(trimethylsilyl)ethyl, phenacyl, p-methoxybenzyl, acetonyl, o-nitrobenzyl 4-pyridylmethyl and t-butyl.

9. The compound of claim 6 wherein P' is selected from the group consisting of trialkylsilyl, aryl(alkyl)alkoxysilyl, alkoxy(diaryl)silyl, (diaryl)alkylsilyl, alkyloxycarbonyl, substituted alkyloxycarbonyl, benzyloxycarbonyl, substituted benzyloxycarbonyl, allyloxycarbonyl and substituted allyloxycarbonyl.

10. The compound of claim 6 wherein P' is selected from the group consisting of t-butylmethoxyphenylsilyl, t-butoxydiphenylsilyl, trimethylsilyl, triethylsilyl, t-butyldimethylsilyl, o-nitrobenzyloxycarbonyl, p-nitrobenzyloxycarbonyl, benzyloxycarbonyl, t-butyloxycarbonyl, 2,2,2-trichloroethyloxycarbonyl and allyloxycarbonyl.

11. The compound of claim 6 wherein Z is selected from the group consisting of methanesulfonyloxy, trifluoromethanesulfonyloxy, fluorosulfonyloxy, p-toluenesulfonyloxy, 2,4,6-triisopropylbenzenesulfonyloxy, p-bromobenzenesulfonyloxy, p-nitrobenzenesulfonyloxy, bromo and iodo.

* * * * *